(12) United States Patent
Huntington et al.

(10) Patent No.: US 11,399,823 B2
(45) Date of Patent: Aug. 2, 2022

(54) METHOD AND APPARATUS FOR LOADING SUTURE

(71) Applicant: Maruho Medical, Inc., Reno, NV (US)

(72) Inventors: Andrew J. Huntington, Reno, NV (US); Brett A. Snyder, Reno, NV (US); Matthew Byrnes Newell, Reno, NV (US); Micah Bruvold Black, Reno, NV (US)

(73) Assignee: Maruho Medical, Inc., Reno, NV (US)

( * ) Notice: Subject to any disclaimer, the term of this patent is extended or adjusted under 35 U.S.C. 154(b) by 8 days.

(21) Appl. No.: 16/734,406

(22) Filed: Jan. 6, 2020

(65) Prior Publication Data

US 2021/0204935 A1    Jul. 8, 2021

(51) Int. Cl.
*A61B 17/06* (2006.01)

(52) U.S. Cl.
CPC ..... *A61B 17/06066* (2013.01); *A61B 2017/0609* (2013.01)

(58) Field of Classification Search
CPC . A61B 17/34; A61B 1/70469; A61B 17/0625; A61B 17/06114; A61B 17/06066; A61B 2017/0609
See application file for complete search history.

(56) References Cited

U.S. PATENT DOCUMENTS

| | | | | |
|---|---|---|---|---|
| 3,901,244 A | * | 8/1975 | Schweizer | A61B 17/04 606/145 |
| 5,478,344 A | * | 12/1995 | Stone | A61B 17/0469 206/339 |
| 5,478,345 A | * | 12/1995 | Stone | A61B 17/0469 206/339 |
| 5,630,825 A | * | 5/1997 | de la Torre | A61B 17/0469 206/339 |
| 5,733,293 A | | 3/1998 | Scirica et al. | |
| 6,126,666 A | | 10/2000 | Trapp et al. | |
| 6,807,796 B1 | | 10/2004 | Dey et al. | |
| 7,615,059 B2 | * | 11/2009 | Watschke | A61B 17/0469 606/144 |
| 2010/0307934 A1 | | 12/2010 | Chowaniec et al. | |
| 2011/0071550 A1 | | 3/2011 | Diduch et al. | |
| 2014/0316443 A1 | | 10/2014 | Fanton et al. | |

FOREIGN PATENT DOCUMENTS

| | | |
|---|---|---|
| WO | WO 2019/191768 | 10/2019 |
| WO | WO 2021/141675 | 7/2021 |

* cited by examiner

*Primary Examiner* — Tuan V Nguyen
(74) *Attorney, Agent, or Firm* — Levine Bagade Han LLP

(57) ABSTRACT

A loader is disclosed that can load a suture and/or a shuttle into a suture device. The loader can have a suture and/or a shuttle that can be moved (e.g., via a loader control) from a non-loaded configuration to a loaded configuration without damaging the suture or the shuttle. The shuttle can be moved from a shuttle first position to a shuttle second position. When the shuttle is in the shuttle first position, a suture device can be positionable in a device space on the loader. When the suture device is positioned in the device space, the shuttle can be moved from the shuttle first position to the shuttle second position. When the shuttle is in the shuttle first position, the shuttle can be outside the suture device. When the shuttle is in the shuttle second position, the shuttle can be inside the suture device.

19 Claims, 27 Drawing Sheets

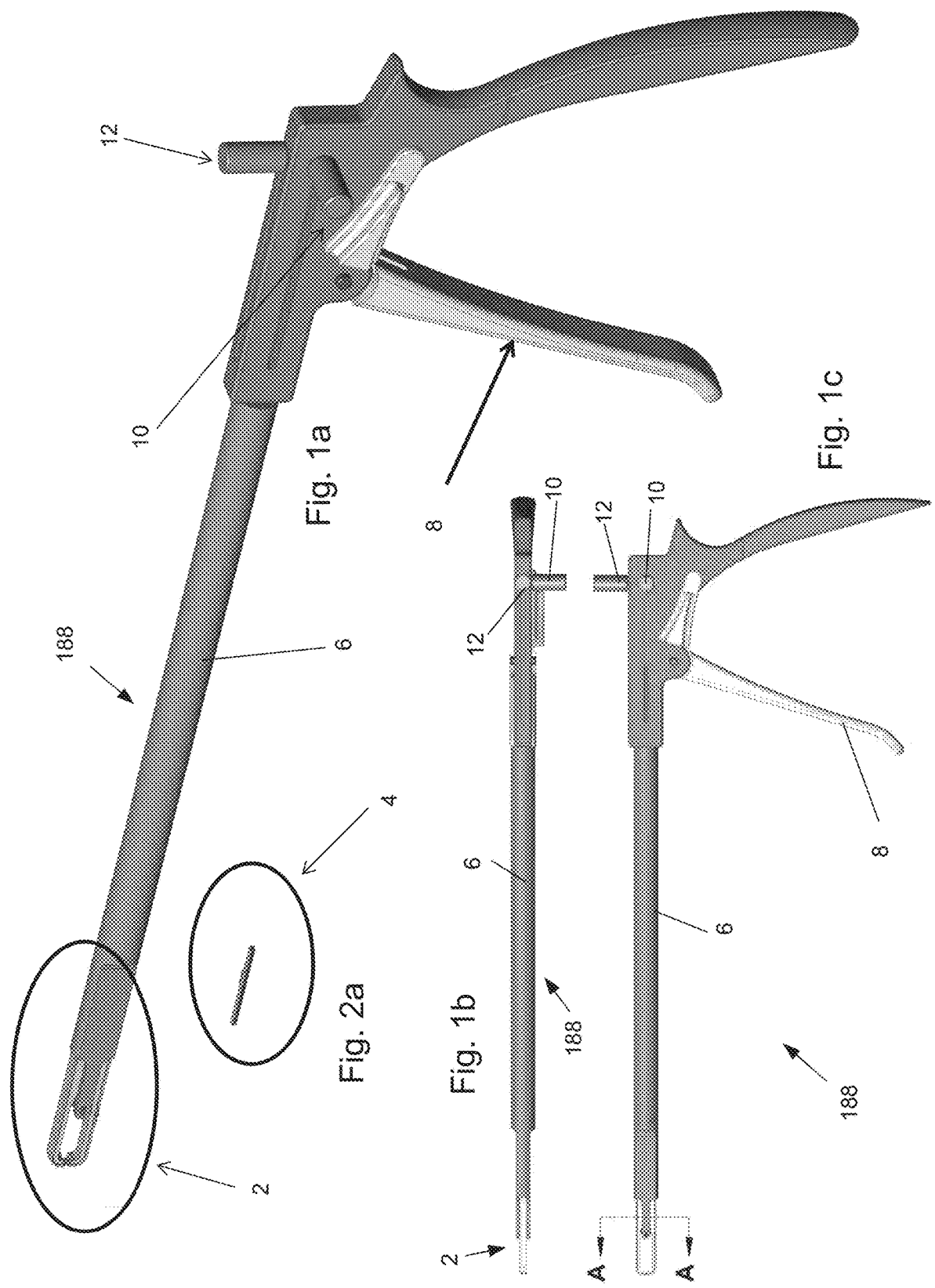

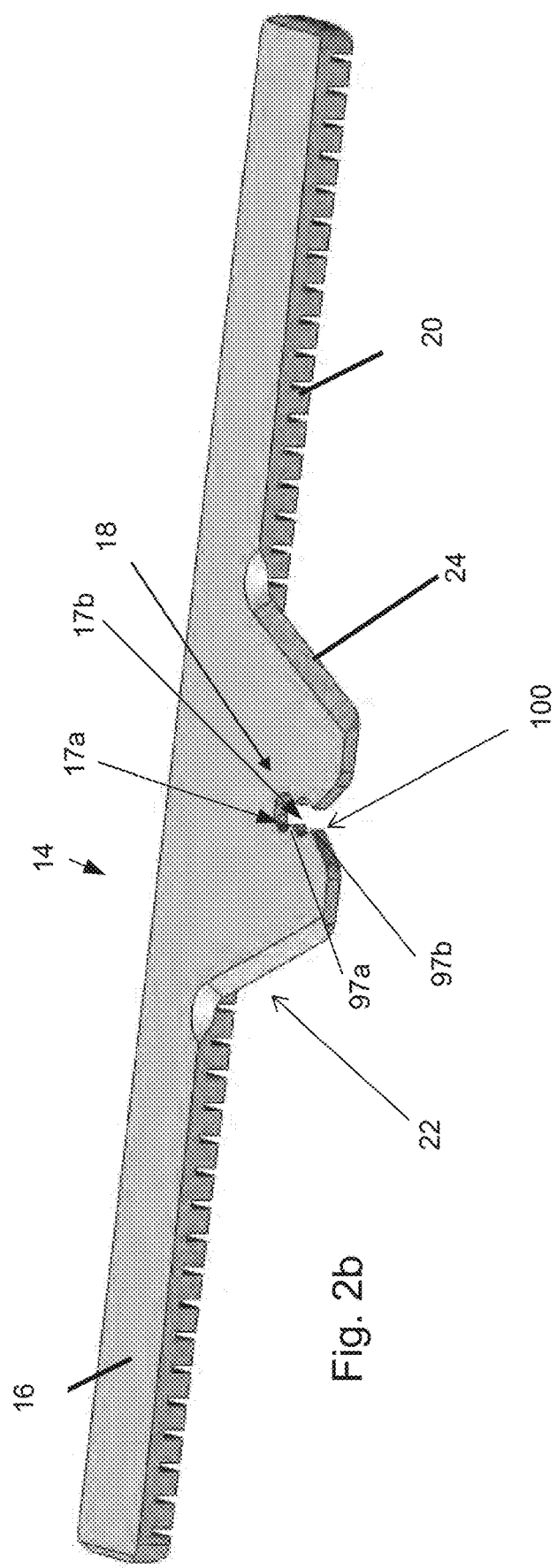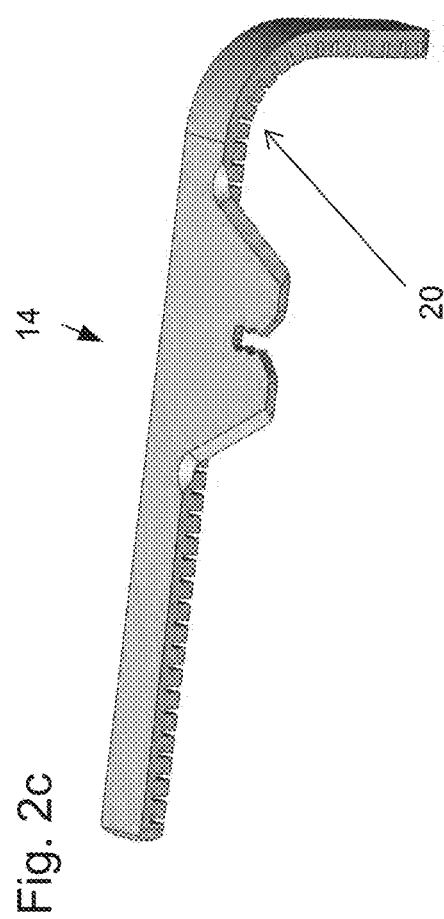

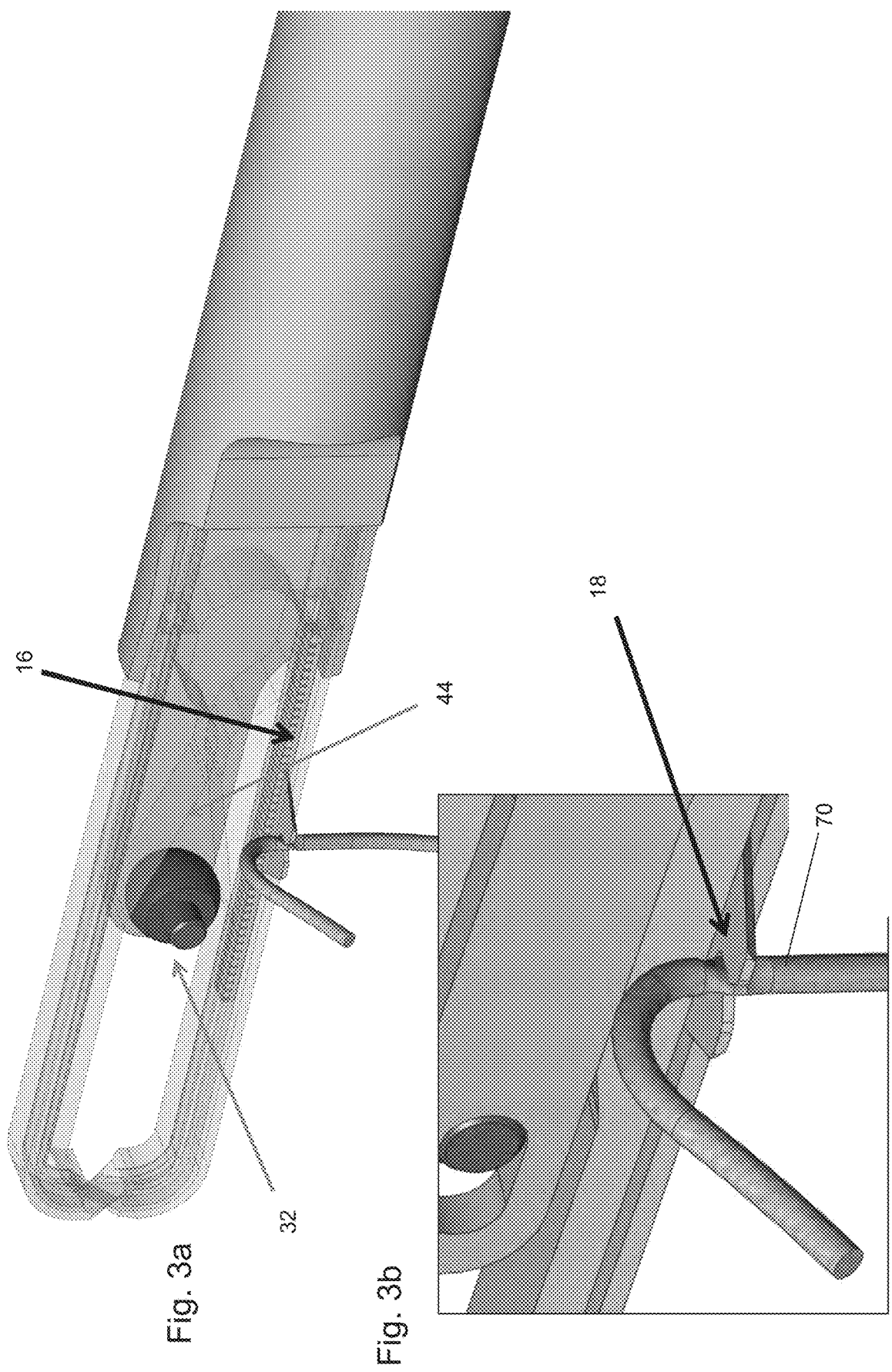

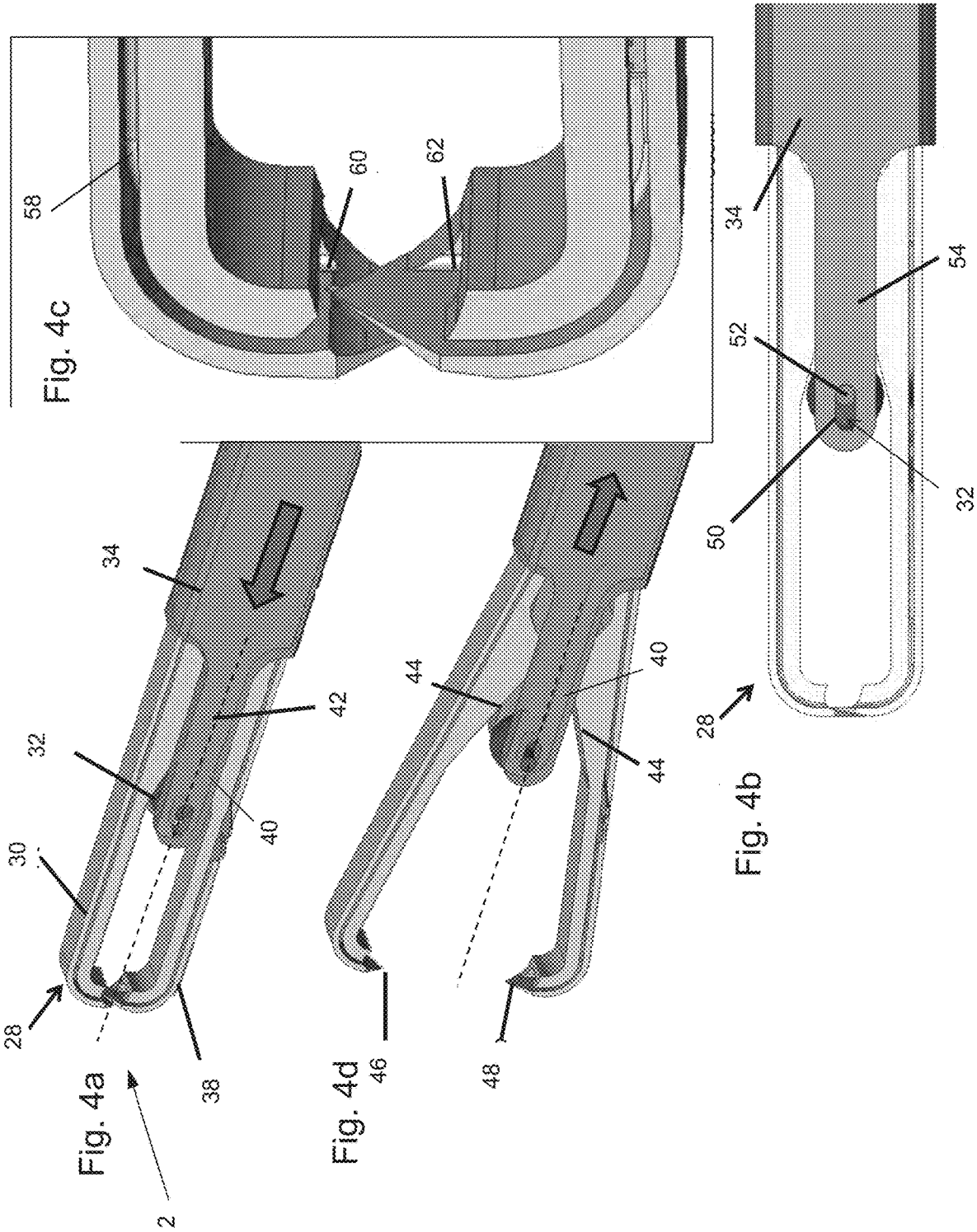

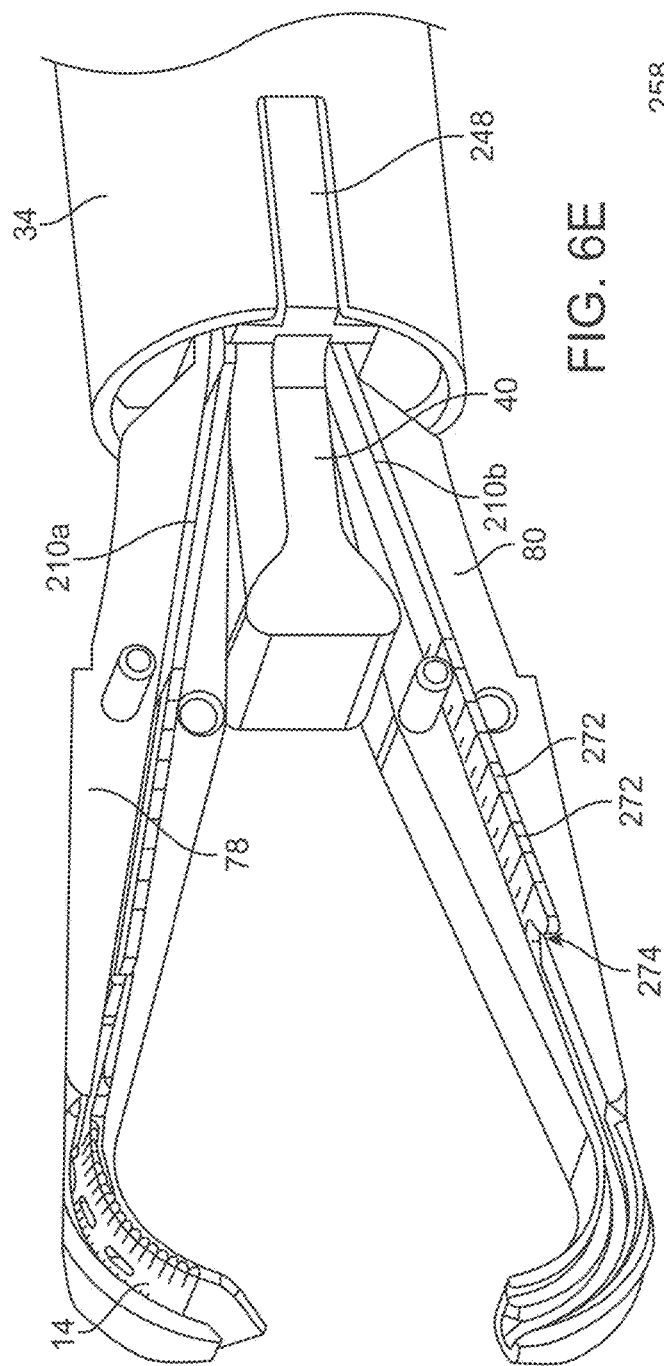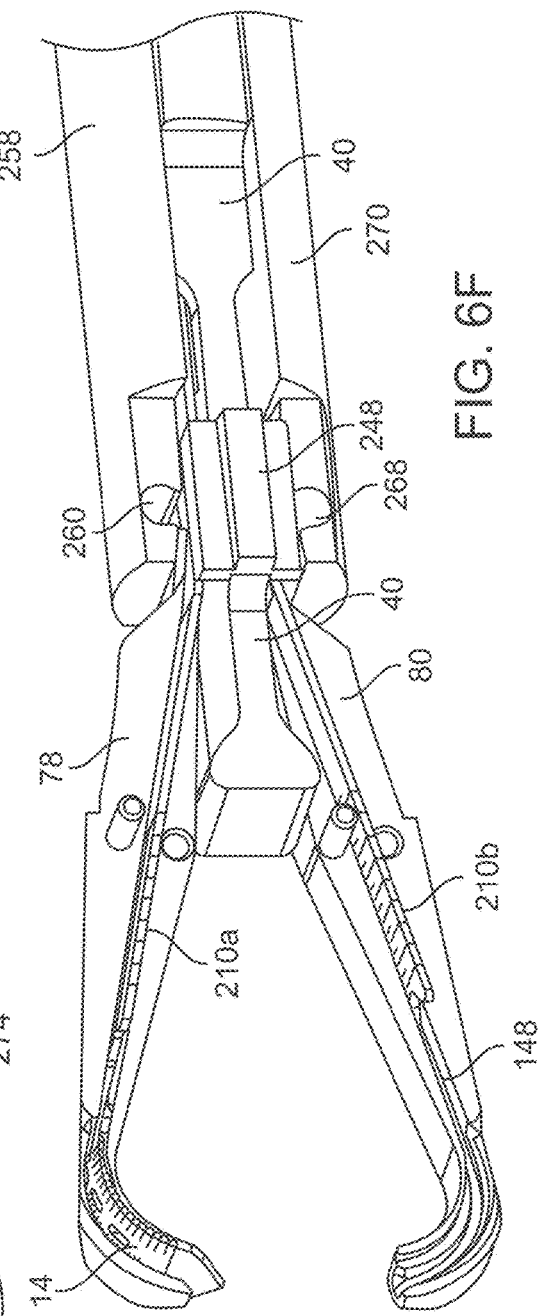

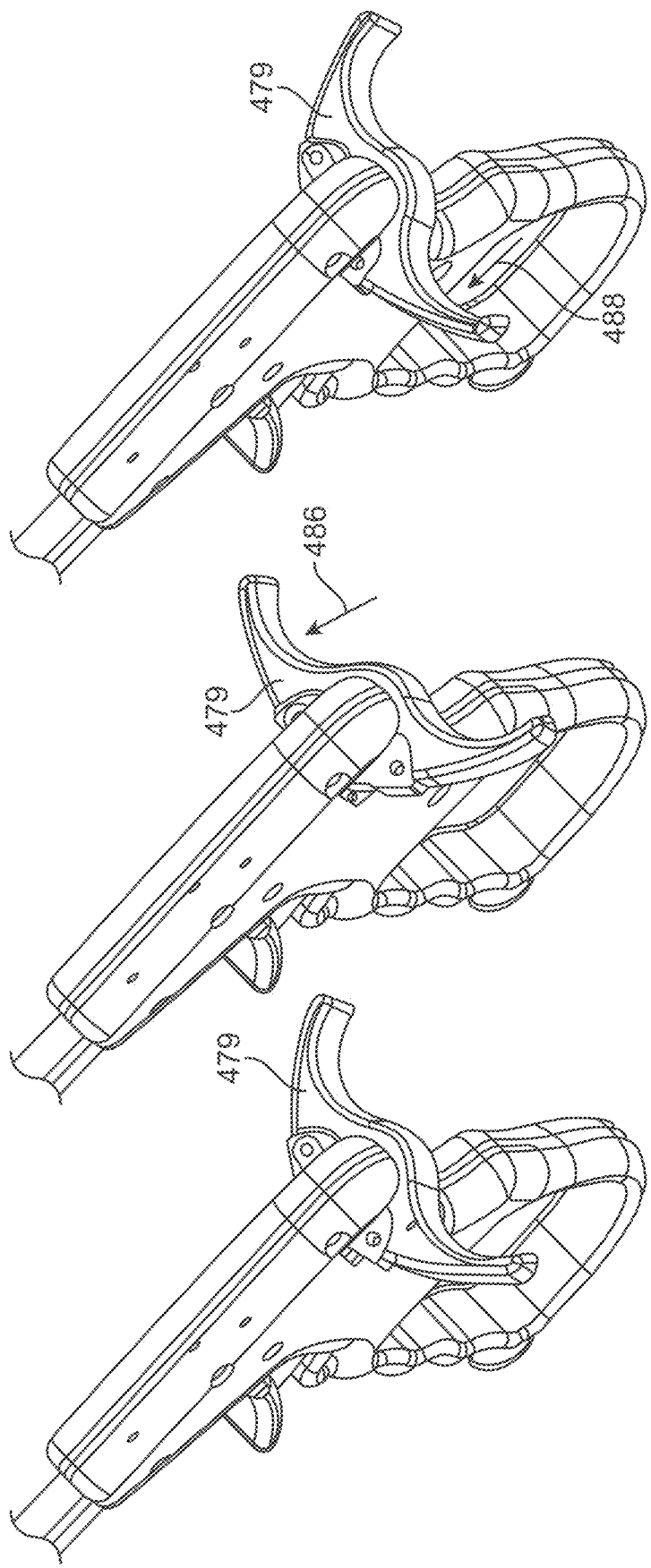

METHOD AND APPARATUS FOR LOADING SUTURE

BACKGROUND

1. Technical Field

The present disclosure relates to systems, methods, and devices for loading suture and/or shuttles into suture devices (also referred to as suture manipulating devices).

2. Description Of Related Art

Suture devices can pass suture and/or shuttles through tissue but may need to be loaded with suture and/or a shuttle before use.

A need still exists to load suture and/or shuttles into suture devices without damaging the suture and/or the shuttle during the loading process.

SUMMARY

This disclosure relates generally to suture devices and methods of loading the same.

Suture device loaders are disclosed. For example, a suture device loader is disclosed that can have a body. The body can have a device space. The suture device loader can have a shuttle. The shuttle can be moveable from a shuttle first position to a shuttle second position. When the shuttle is in the shuttle first position, a suture device can be positionable in the device space. When the suture device is positioned in the device space, the shuttle can be moveable from the shuttle first position to the shuttle second position. When the shuttle is in the shuttle first position, the shuttle can be outside the suture device. When the shuttle is in the shuttle second position, the shuttle can be inside the suture device.

Suture device loaders are disclosed. For example, a suture device loader is disclosed that can have a body. The body can have a device space. The suture device loader can have a suture. The suture can be moveable from a suture first position to a suture second position. When the suture is in the suture first position, a suture device is positionable in the device space. When the suture device is positioned in the device space, the suture can be moveable from the suture first position to the suture second position. More of the suture can be in the suture device when the suture is in the suture second position than when the suture is in the suture first position.

Methods of loading suture devices are disclosed. For example, a method of loading a suture device is disclosed that can include removably attaching the suture device to a loader. The loader can have a loader control, a suture, and a shuttle. The method can include loading, via the loader control, the shuttle and the suture into the suture device. Loading can comprise moving, via the loader control, the shuttle and the suture from a non-loaded configuration to a loaded configuration by moving the loader control from a loader control first position to a loader control second position. When the loader control is in the loader control first position, the shuttle and the suture can be in the non-loaded configuration. When the loader control is in the loader control second position, the shuttle and the suture can be in the loaded configuration.

BRIEF DESCRIPTION OF THE FIGURES

The drawings shown and described are exemplary embodiments and non-limiting. Like reference numerals indicate identical or functionally equivalent features throughout.

FIGS. 1a, 1b and 1c are perspective, top and side views, respectively, of a variation of the suture passing device.

FIGS. 2a and 2b are a distant and close-up view, respectively, of a variation of the shuttle in a straight configuration.

FIG. 2c is a close-up view of the variation of the shuttle from FIGS. 2a and 2b in a curved configuration.

FIG. 3a is a close-up, perspective, partial see-through view of the distal end of a variation of the suture passing device attached to a length of a suture.

FIG. 3b is a close-up view of a portion of FIG. 3a.

FIGS. 4a and 4b are close-up perspective and side views, respectively, of the distal end of a variation of the suture passing device in a closed configuration.

FIG. 4c is a close-up of the distal end of FIGS. 4a and 4b.

FIG. 4d is a close-up perspective view of the distal end of the device of FIG. 4a in a closed configuration.

FIGS. 6A through 6F are bottom and side perspective, partial see-through (the upper jaw is see-through), longitudinal cross-section, partial cut-away close-up, and partial cut-away views, respectively, of the distal end of a variation of the device with the jaws in an opened configuration with the shuttle and pushers in various positions, and with the compression cover not shown in FIG. 6F for illustrative purposes.

FIG. 26b does not show the pushers for illustrative purposes.

FIG. 13C illustrates a variation of a handle of the device.

FIG. 13D illustrates a variation of a handle of the device.

FIG. 13E illustrates a variation of a handle of the device.

DETAILED DESCRIPTION

Figure 5A:
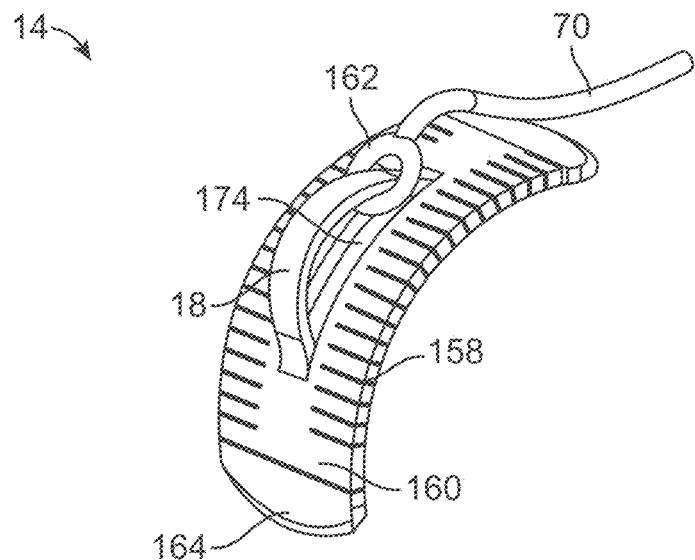
FIGS. 5A and 5B illustrate variations of the shuttle.

FIGS. 1a through 1c illustrate a suture passing device 188 that can be used to pass suture 70 through soft or hard tissue 74 with or without removing the device 188 or the suture 70 from the target site while creating one or more complete stitches.

The suture passing device 188 can have an ergonomic handle 104, a sliding tube actuator 6, and a distal end 2. The ergonomic handle 104 can be used to control the distal end 2. The ergonomic handle 104 can have a side knob 10. The ergonomic handle 104 can have a top knob 12. The top knob 12 and/or the side knob 10 can individually or in concert, advance and/or retract the upper 86 and/or lower pusher 76.

The sliding tube actuator 6 can have an outer compression cover 34 and an inner rod (not shown due to obstruction by the outer compression cover 34). The inner rod can be fixedly attached to the handle 104 and the proximal end of the jaw structure 28. The outer compression cover 34 can be radially outside of the inner rod. The outer compression cover 34 can be actuated by the handle 104, for example be distally and proximally translated with respect to the handle 104 when the trigger 8 is squeezed or released.

FIGS. 2a and 2b illustrate that the device 188 can have a sliding ribbon shuttle 14 or needle held within the device 188. The shuttle 14 can have an elongated shuttle rail 16. The shuttle rail 16 can have numerous slits 20 along one or both sides of the shuttle rail 16. The slits 20 can be positioned at regular or irregular length intervals along the rail 16.

The shuttle 14 can have a suture holder 18 extending laterally from the rail 16. The shuttle 14, for example the suture holder 18, can extend out of the lateral side slot 72 of the arm structure. The suture holder 18 can extend from the left and/or right side of the device 188. The distal end 2 of the device 188 can be reversible so the suture holder 18 can be switched from one side of the device 188 to the other side of the device 188. The suture holder 18 can have a generally flat, isosceles trapezoid configuration. The suture holder 18 can have a suture holding notch 100. The notch 100 can have an inner hole 17a, an outer hole 17b contiguous with the inner hole 17a, and a first cleat 97a positioned between the inner hole 17a and the outer hole 17b. The notch 100 can have a second cleat 97b on the side of the outer hole away from the inner hole. The notch 100 can be configured to secure to suture 70. For example, the suture 70 can be compressed and friction fit in the inner cleat 97a.

The suture holder 18 can have a front leading edge and a rear leading edge. The edges can be slanted at a right or non-right angle with respect to the longitudinal axis of the rail 16. One or both of the edges can be sharpened to be traumatic to tissue 74, for example to cut through soft tissue 74. The edges can cut through tissue 74, allowing the suture holder 18 to pull the suture 70 through the tissue 74 immediately behind the respective edge.

The shuttle 14 can be made from a flexible polymer, such as PEEK, a resilient metal such as Nitinol, any material disclosed herein or combinations thereof. The shuttle 14 can be made from a molded polymer. The shuttle 14 can be pre-curved, for example to reduce resistance when going around curves in the tracks.

FIG. 2c illustrates that the rail 16 can curve at the locations of the slits 20, and/or the rail 16 can be pre-curved.

FIGS. 3a and 3b illustrate that the suture passing device 188 can capture or releasably attach to the suture 70 in the inner and/or outer cleats 97a and/or 97b of the suture holder 18. The suture 70 can be loaded or held laterally of the jaw structure 28, out of plane with the rotation of the jaws. The device 188 can make multiple passes of the suture 70 through the tissue 74 without extracting or reloading the suture passing device 188. The jaw structure 28 can resiliently deform open at the proximal end of the jaw structure 28, having no hinge. The jaws can be opened and/or closed with no mechanical pivots or linkages in the jaw structure 28.

FIG. 4a illustrates that the suture passer device 188 can have a jaw structure 28 with a top jaw 30 and a bottom jaw 38. The entire jaw structure 28 can be an integral piece of material, such as a single molded, cast, or cut element of Nitinol, other resilient metal or polymer, any other material listed herein, or combinations thereof. The jaw structure 28 can be configured to be in an opened configuration (as shown in FIG. 4d) when in an unbiased configuration (i.e., when no external forces are applied).

The jaw structure 28 can have a jaw structure longitudinal axis 42. Each jaw can also have a respective jaw longitudinal axis along the jaw.

The inside channel of the compression cover 34 can be sized and shaped to fit over the jaw structure 28 with minimum clearance when the jaw structure 28 is in a closed configuration. When the compression cover is translated distally 138 with respect to the jaw structure 28, as shown by arrow, the compression cover 34 can press the top and bottom jaws 38 toward the jaw structure longitudinal axis 42. The jaw structure 28 can be fully compressed into a closed configuration, as shown in FIGS. 4a through 4c. In this way, when an actuation lever such as the trigger 8 is actuated, the channel or compression cover 34 can advance to cam closed the jaws. The jaws can pre-pierce the tissue and establish a continuous track for the shuttle to pass through the tissue.

The compression cover 34 can be attached to an opening ball 32 positioned between the first and second jaws.

FIG. 4b illustrates that the opening ball 32 can be rotatably or fixedly attached to a ball axle 52 passing laterally through the opening ball 32. The ball axle 52 can extend out from the lateral sides of the ball 32. The ball axle 52 can be slidably received by axle slots 50 formed through distal arms 54 or extensions 138 of the compression cover 34. When the jaw structure 28 is in a closed configuration, the ball axle 52 can abut and interference fit against the proximal end of the axle slot 50, for example to prevent overextension of the compression cover 34 over the jaw structure 28. When the jaw structure 28 is in an opened configuration, the ball axle 52 can abut and interference fit against the distal end 2 of the axle slot 50, for example to prevent overrotation of the jaws and/or pulling the ball 32 past the ramps 44 on the inside of the jaw structure 28.

FIG. 4c illustrates that the bottom track 66 can distally terminate in a bottom track port 62. The top track 64 can distally terminate at a top track port 60. The top track port 60 can align with and be adjacent to (as shown) or in contact with the bottom track port 62 when the jaw structure 28 is in a closed configuration with the first jaw tip 46 interdigitating with the second jaw tip 48. The tracks of the upper jaw 78 and bottom jaw 38 can form a continuous path when the jaw structure 28 is in a closed configuration. The first jaw tip 46 can interdigitate with and be adjacent or in contact with the second jaw tip 48 when the jaw structure 28 is in a closed configuration.

FIG. 4d illustrates that that compression cover 34 can be translated proximally 126, as shown by arrow, with respect to the jaw structure 28. The ball axle 52 can slide to the distal end 2 of the axle slot 50. The axle slot 50 can then pull the ball axle 52, and therefore the opening ball 32, proximally. The opening ball 32 can then press against the inside surface ramp 44 of the first jaw and/or second jaw. The first jaw tip 46 and/or second jaw tip 48 can then rotate away from the opposing jaw tip. The jaw structure 28 can then be in an opened configuration, as shown.

The proximal ends of the jaws can be rigid or flexible, for example to bend around the opening of the compression cover 34 when the jaws are in an opened configuration. The entire jaws or just the proximal ends of the jaws can be made from Nitinol, for example with the distal ends of the jaws made from stainless steel.

FIG. 5A illustrates that the suture holder 18 can be an arc integral with the shuttle spine 160. For example, the shuttle 14 can be made from a single panel of material (e.g., metal). The lateral sides of the suture holder 18 can be cut, and the longitudinal ends can remain integrated with the shuttle spine 160. The suture holder 18 can then be bent or otherwise deformed away from the plane of the shuttle spine 160, for example forming an arc away from the plane of the shuttle spine 160.

The suture 70 can have a suture loop 162 at the terminal end of the suture 70. The suture loop 162 can extend around and completely or partially circumscribe the suture holder 18. The remainder of the suture 70 can be integral with the suture loop 162, or can removably attached to the suture loop 162. The suture loop 162 can be circular or oval.

Figure 5B:
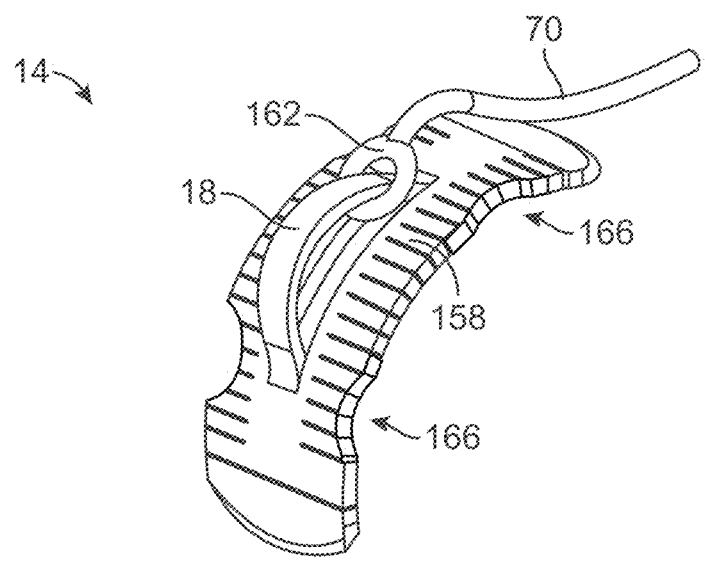
Figure 6A:
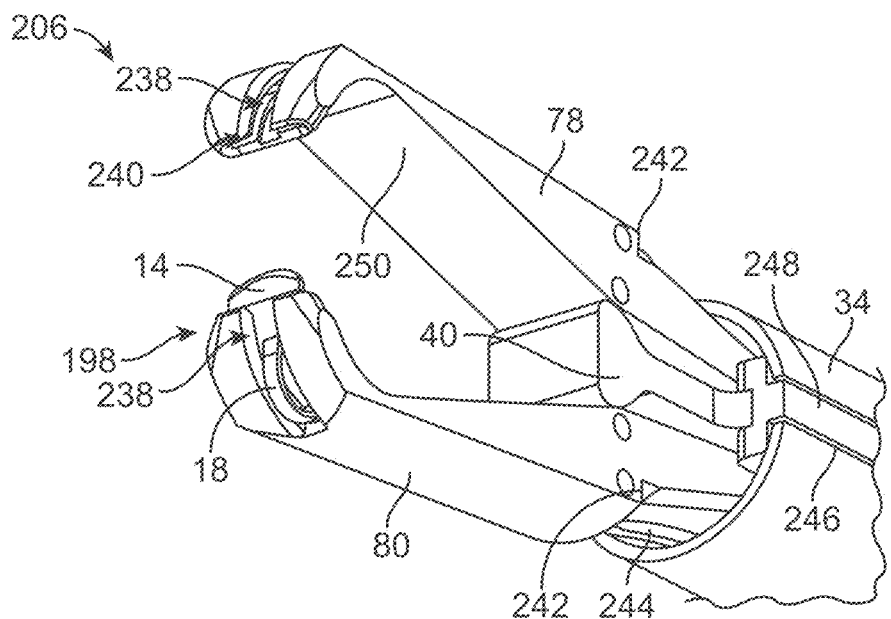
Figure 6B:
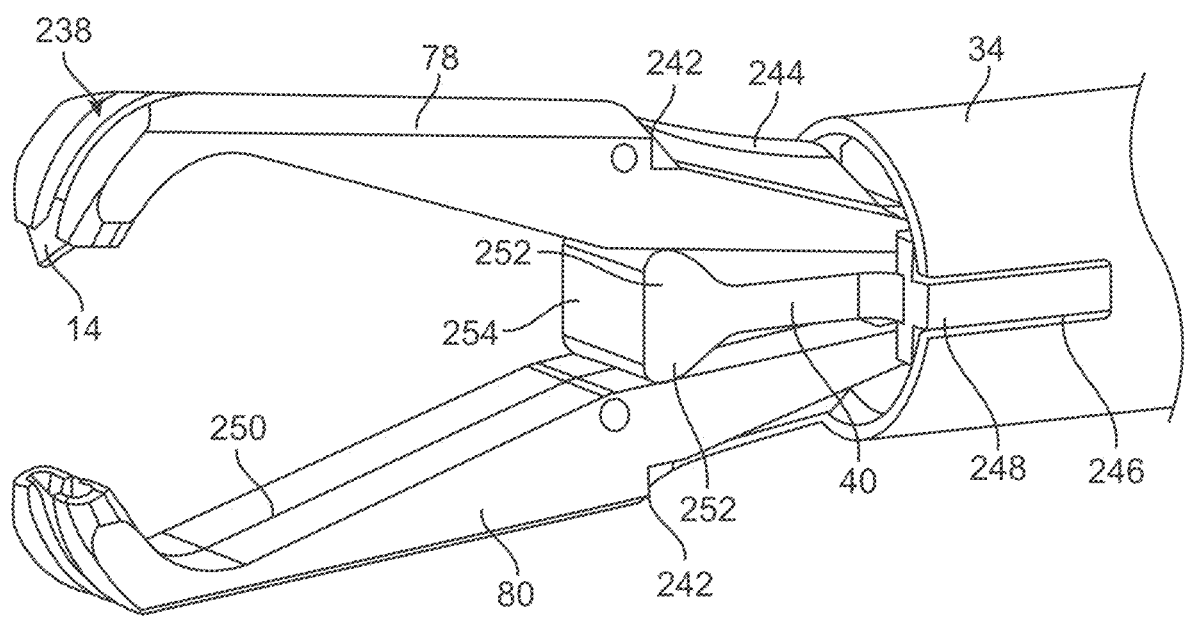
Figure 6C:
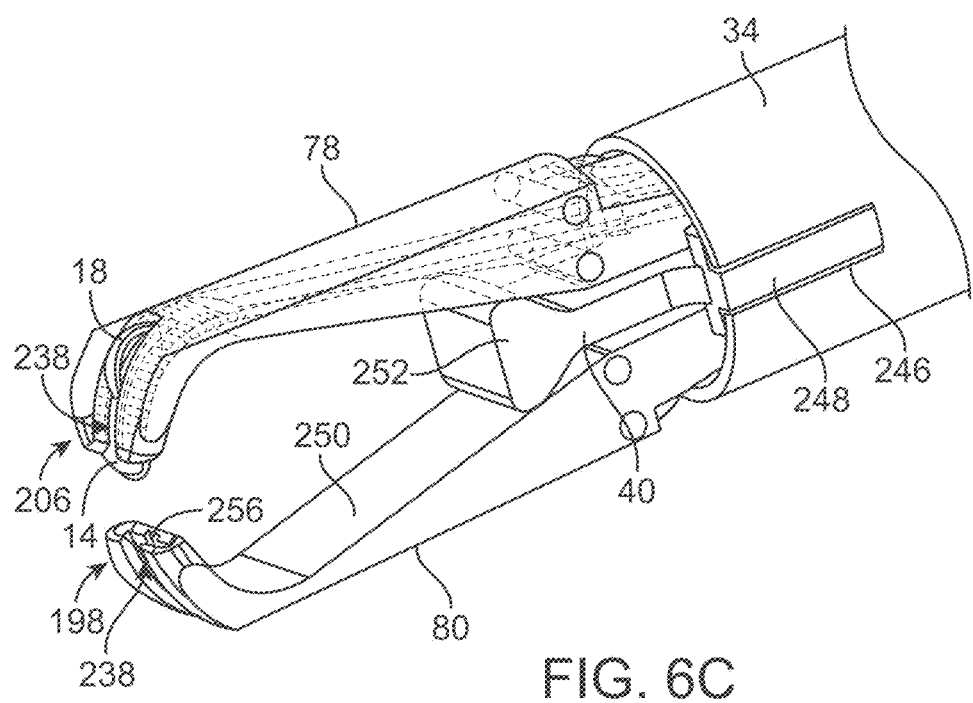
Figure 6D:
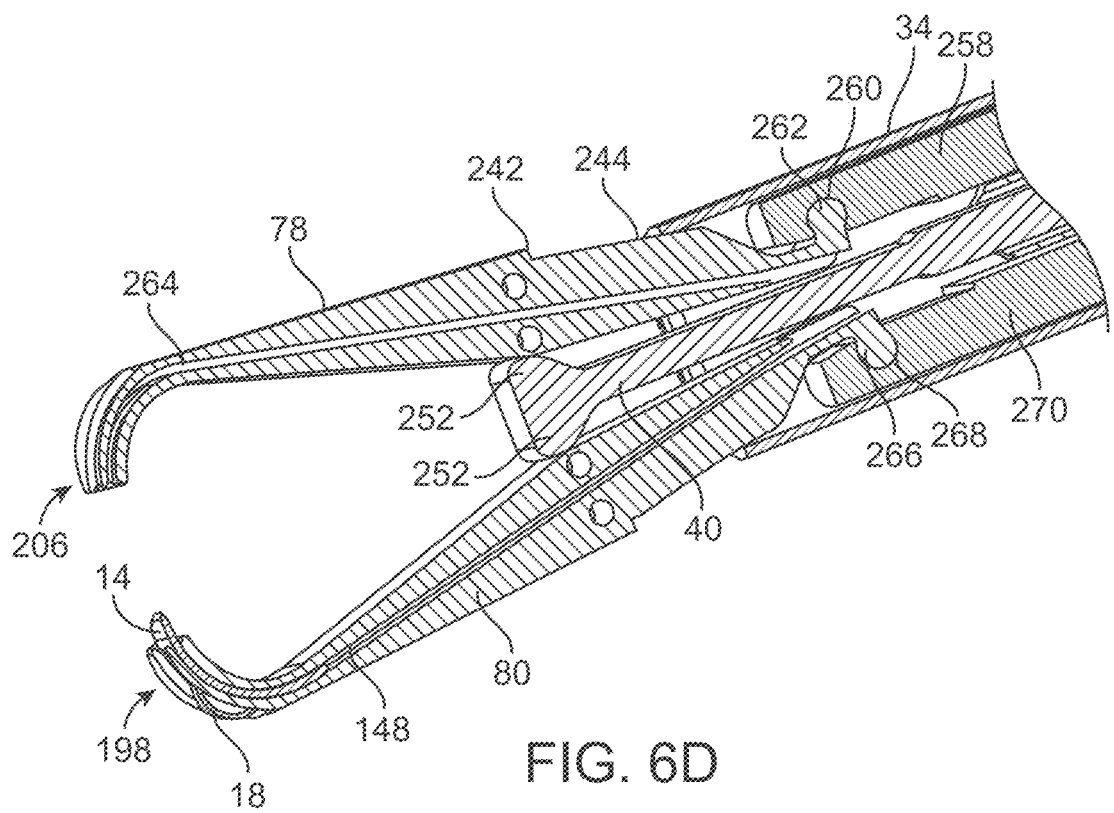
Figure 7A:
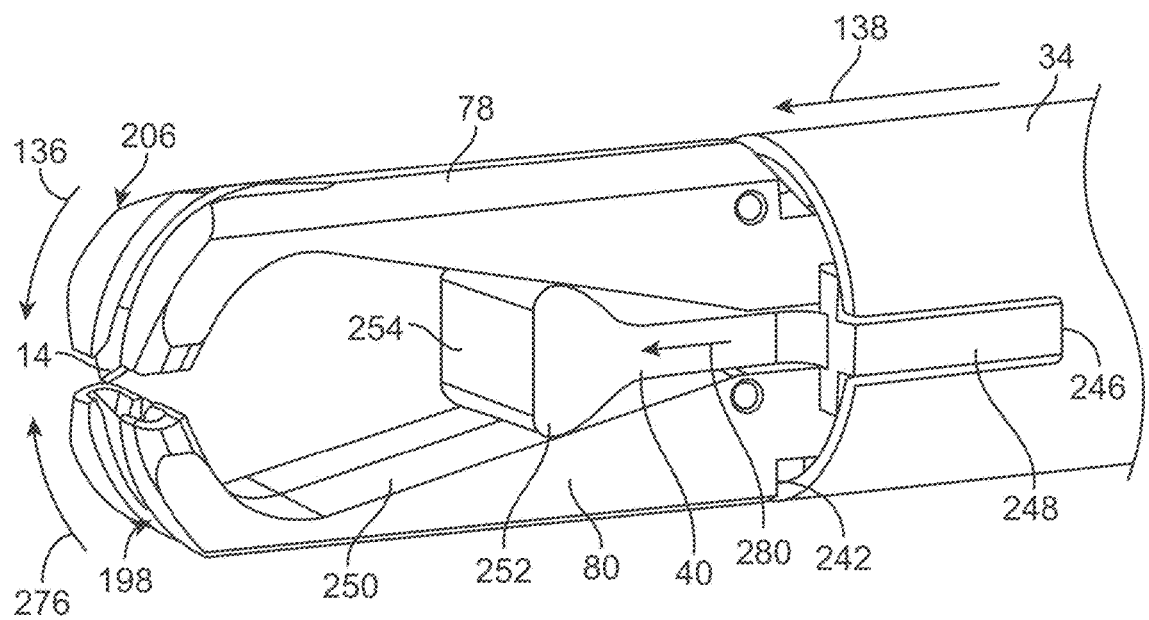
FIG. 7A is a side perspective view of a variation of the distal end of device with the jaws in a closed configuration with the shuttle in the upper jaw and not engaged in the lower jaw.
Figure 7B:
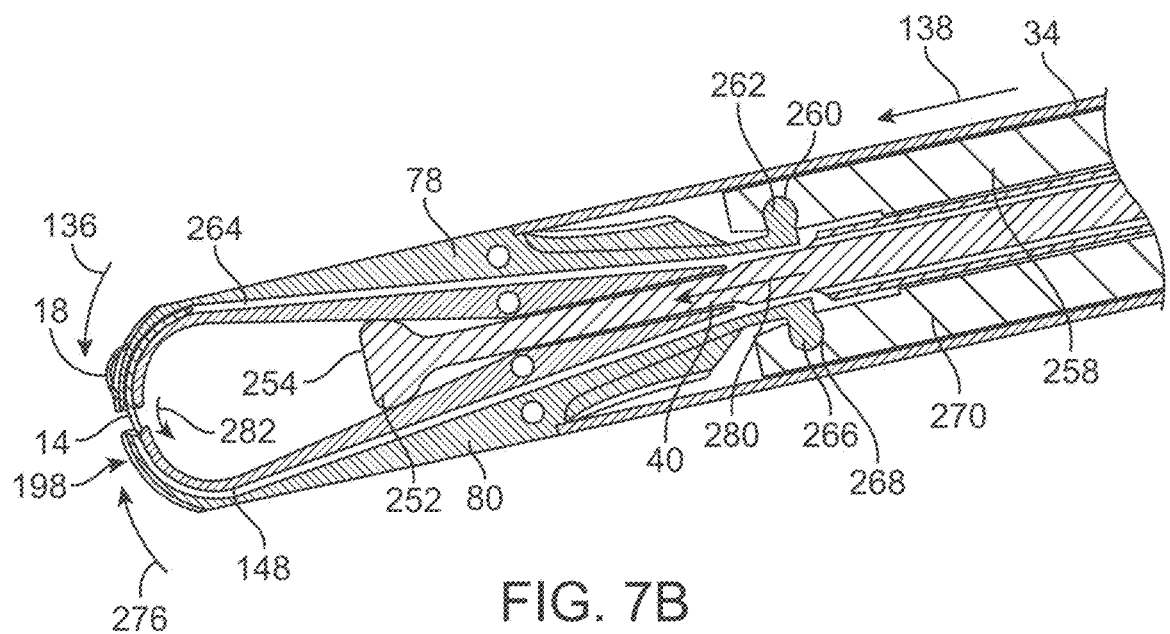
FIGS. 7B and 7C are longitudinal cross-section and side perspective views, respectively, of the device of FIG. 7A with the shuttle in the top and bottom jaws.
Figure 7C:
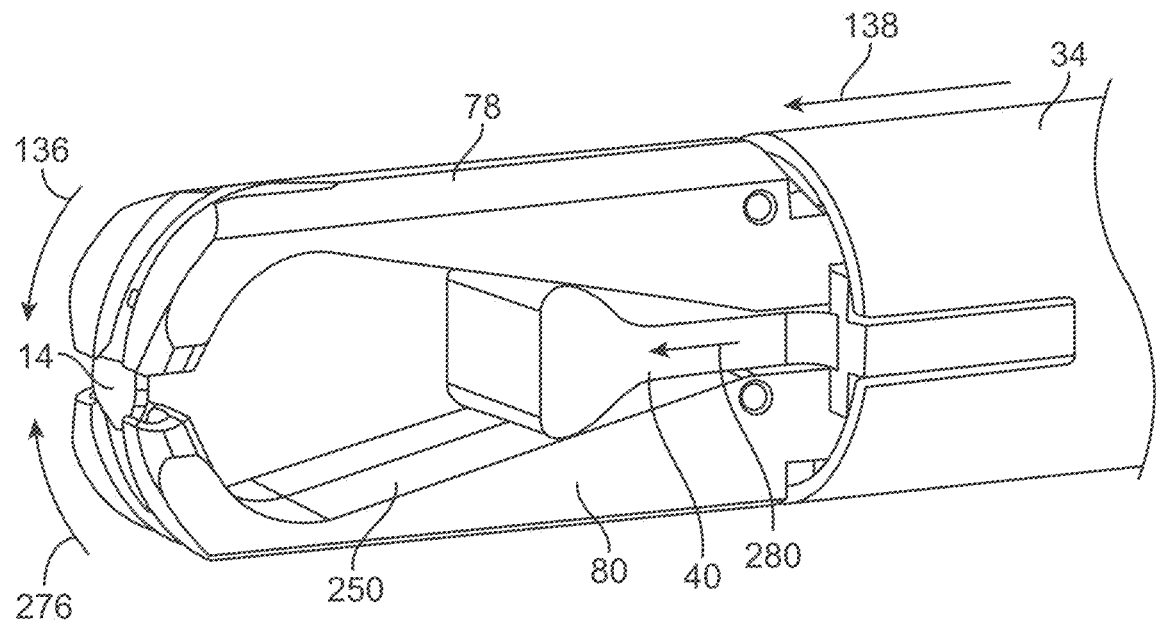
Figure 7D:
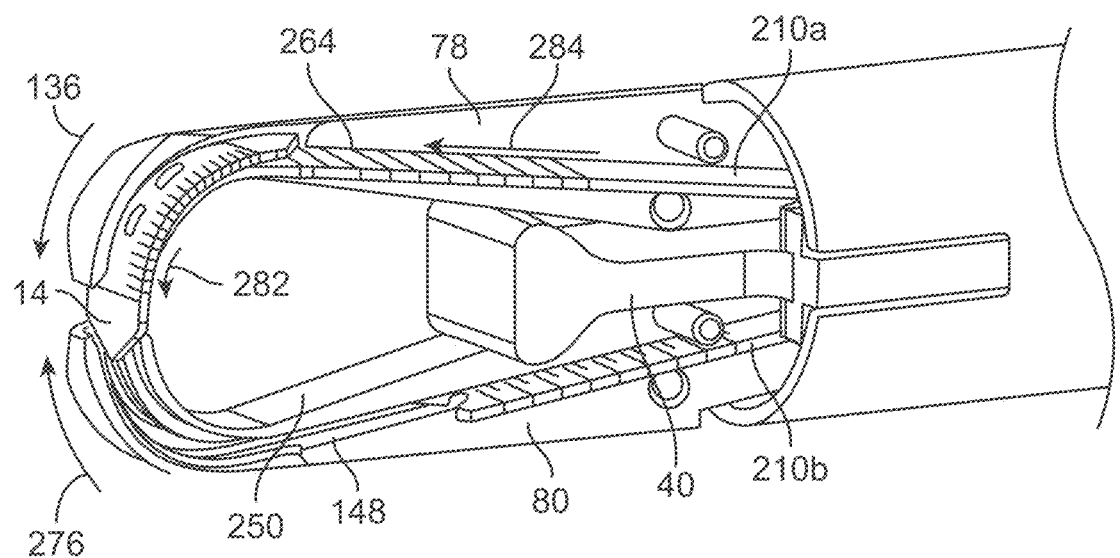
FIG. 7D is a partial cut-away view of FIG. 7C.

FIG. 5B illustrates that the shuttle 14 can have one or more shuttle notches 166 or cut-outs. For example, the shuttle 14 can have two shuttle notches 166 on each lateral site of the shuttle. The shuttle notches 166 can be even longitudinally spaced and distributed along the shuttle 14. The shuttle notches 166 can be curved. The sides of the shuttle 14, other than at the notches, can be straight.

A radius of curvature of the shuttle notch 166 can be from about 1 mm to about 2 mm.

FIGS. 6A through 6F illustrate that the upper jaw tip 206 and/or lower jaw tip 198 can have suture holder slots 238. The suture holder slots 238 can extend medially along the outer surface of the respective jaw tip. The suture holder slot 238 can extend from the outer surface of the jaw tip to the respective track. The suture holder 18 can be accessible through or extend out of the suture holder slot 238. The suture 70 (not shown) can attach to or be integral with the suture holder 18 in or outside of the suture holder slot 238.

The upper track 264 can distally terminate at an upper jaw tip shuttle port 240. The lower track 148 can distally terminate at a lower jaw tip shuttle port 256. The shuttle 14 can extend out of or into, and pass through each of the shuttle 14 ports. During use, the sharpened shuttle tip 164 extending out of the shuttle port can pierce, cut and dissect tissue 74 when the jaws are rotated to a closed configuration.

The upper jaw 78 and/or lower jaw 80 can have a jaw stop 242. The jaw stop 242 can be a feature, shape or configuration that can abut and stop the distal translation of the compression cover 34 with respect to the jaws. For example, the distal terminal end of the compression cover 34 can abut the jaw stops 242 when the jaws are in a closed configuration.

The radially inner surface of the jaws can have radially inner slopes 250.

The upper jaw 78 and/or lower jaw 80 can have a jaw slide 244. The jaw slide 244 can be a radially outer surface of the jaws between the jaw stops 242 and the compression cover 34 when the compression cover 34 is in a proximally retracted 126 position with respect to the jaws and/or the jaws are in an opened configuration. The jaw slide 244 can increase in radius from the jaw structure longitudinal axis 42 in the distal longitudinal direction (e.g., the larger the longitudinal dimension of the jaw slide 244, the larger the radial dimension of the jaw slide 244). When the compression cover is translated distally 138 with respect to the jaws, the radially inner distal edge of the compression cover 34 can slide along the jaw slide 244, and press the jaw slide 244 toward the jaw structure longitudinal axis 42. A radially compressive force delivered from the compression cover 34 to the jaw slide 244 can create a torque in the respective jaw, rotating the respective jaw toward the jaw structure longitudinal axis 42 and the opposing jaw.

The device 188 can have a jaw control extension 40. The jaw control extension 40 can extend along the jaw structure longitudinal axis 42. The jaw control extension 40 can extend between the jaws proximal to the jaw tips. The jaw control extensions 40 can terminate in a jaw control extension head 254.

The jaw control extension head 254 can have one or two lobes or cams. Each lobe can extend from the longitudinal axis of the jaw control extension 40 toward a jaw. The lobes can act similarly to the opening roller ball shown in FIGS. 4a, 4d, and elsewhere herein. The upper jaw 78 and lower jaw 80 can have upper and inner jaw radially inner slopes 250, respectively. The inner slopes can be the radially inner surfaces of the jaws proximal to the jaw tips and distal to the jaw control extension head 254 when the jaw control extension head 254 is in a proximally retracted position with respect to the jaws. The radially inner slope 250 can increase in radius from the jaw structure longitudinal axis 42 in the distal longitudinal direction (e.g., the larger the longitudinal dimension of the radially inner slope 250, the larger the radial dimension of the radially inner slope 250). When the jaw control extension 40 is proximally translated or retracted with respect to the jaws, the lobes can slide against the radially inner slopes 250 of the jaws and press the jaws away from each other into an open configuration.

When the jaws are in an open configuration, the compression cover 34 can be positioned at or proximally past the proximal end of the jaw slides 244, and the jaw extension head can be positioned at or proximally past the proximal end of the radially inner slopes 250.

The jaw control extension 40 can be attached to or integral with a control rail 248. The control rail 248 can extend radially from one or both lateral sides of the jaw control extension 40, for example in a plane at a right angle to a plane defined by the opposing jaws or the opposing extension head lobes 252.

The compression cover 34 can have a control rail slot 246. The control rail slot 246 can extend to the distal terminal end of the compression cover 34. The control rail 248 can be fixed to or longitudinally translate within the control rail slot 246. The control rail 248 can interference fit, abut or stop against the proximal end of the control rail slot 246, for example when the control rail 248 is in a proximal or distal longitudinal position with respect to the jaws. The control rail 248 can move longitudinally in unison (i.e., coincidentally) with the compression cover 34 in the distal and/or longitudinal directions. The control rail 248 can move longitudinally in unison with the jaw control extension 40 in the distal and/or longitudinal directions.

The device 188 can have an upper socket arm 258 and a lower socket arm 270 radially inside of the compression cover 34. The upper socket arm 258 and lower socket arm 270 can be a single integrated element (e.g., a hollow cylinder) or separate elements. The upper socket arm 258 can be opposite the lower socket arm 270. The upper socket arm 258 can be translatably fixed (i.e., mechanically attached to translate in unison) to the lower socket arm 270. The jaw control extension 40 can extend longitudinally between the upper 258 and lower socket arms 270 or within a hollow channel inside a unitary socket arm (comprising the upper 258 and lower socket arms 270 as an integrated element). The distal terminal ends of the socket arms can extend to or proximal to the distal terminal end of the compression cover 34 when the jaws are in an open configuration.

The proximal terminal end of the upper jaw 78 can have a laterally elongated upper jaw bearing 262. The upper jaw bearing 262 can extend radially outward from the remainder for the proximal end of the upper jaw 78.

The distal end 2 of the upper socket arm 258 can have a laterally elongated upper jaw socket 260. The upper jaw socket 260 can open medially and have a diameter approximately equal to or slightly larger than the diameter of the upper jaw bearing 262.

An upper jaw 78 hinge can have the upper jaw bearing 262 and the upper jaw socket 260. The upper jaw 78 can rotate around the transverse axis of the upper jaw bearing 262. The upper jaw bearing 262 can rotate in the upper jaw socket 260.

The proximal terminal end of the lower jaw 80 can have a laterally elongated lower jaw bearing 266. The lower jaw bearing 266 can extend radially outward from the remainder for the proximal end of the lower jaw 80.

The distal end 2 of the lower socket arm 270 can have a laterally elongated lower jaw socket 268. The lower jaw socket 268 can open medially and have a diameter approximately equal to or slightly larger than the diameter of the lower jaw bearing 266.

A lower jaw 80 hinge can have the lower jaw bearing 266 and the lower jaw socket 268. The lower jaw 80 can rotate around the transverse axis of the lower jaw bearing 266. The lower jaw bearing 266 can rotate in the lower jaw socket 268.

The upper 86 and/or lower pushers 76 can have entire lengths or only distal ends 2 that can have articulated segmentations 286. The articulated segments 286 can rotate with respect to each other around an axis perpendicular to the longitudinal axis of the respective pusher. The articulated segmentations 286 can be connected by a discrete hinge (e.g., a pin or snap connection) or can be longitudinally coincidental or longitudinally alternating lateral slots cut into the sides of the pusher, similar to the shape of the shuttle lateral slots 158. The proximal end of either or both upper 86 and lower pushers 76 can have a continuous, non-segmented, flat, uniform ribbon of material.

Each of the upper 86 and/or lower pushers 76 can have distal terminal ends that can have a shuttle seat 274. The shuttle seat 274 can be an inverse shape to the shape of the shuttle tip 164. For example, if the shuttle tip 164 has an angled end, the shuttle seat 274 can have the opposite angle. If the shuttle tip 164 has a convex curved end, the shuttle seat 274 can have a concave curved end with the same radius of curvature as the shuttle tip 164.

FIGS. 7A through 7D illustrate that the compression cover 34 can be distally translated, as shown by arrow, with respect to the jaws. The compression cover 34 can deliver translational force through the edges of the control rail slot 246 to the control rail 248. The control rail 248 can deliver the translational force to the jaw control extension 40. The jaw control extension 40 can translate distally, as shown by arrow, concurrently with the compression cover 34. The compression cover 34 can translate 138 over the jaw slides 244, pressing radially inward on the jaw slides 244. The jaw control extension head 254 can move distally with respect to the jaws, as shown by arrow 280, for example, allowing the closure of the jaws without interference fitting or abutting against the jaw control extension head 254. The upper jaw 78 and/or lower jaw 80 can rotate radially inward, as shown by arrows.

When the jaws are in a closed configuration, the compression cover 34 can be positioned at or adjacent to the jaw stop 242, and the jaw extension head can be positioned at or proximally past the proximal end of the radially inner slopes 250.

When the jaws are in a closed configuration, if the shuttle 14 is in the upper track 264, the upper pusher 86 can translate distally through the upper track 264. The distal terminal end of the upper pusher 86 can abut the shuttle 14. The upper pusher 86 can then push the shuttle 14 through the upper track 264, out the upper jaw tip shuttle port 240 and into the lower jaw tip shuttle port 256.

When the jaws are in a closed configuration, if the shuttle 14 is in the lower track 148, the lower pusher 76 can translate distally through the lower track 148. The distal terminal end of the lower pusher 76 can abut the shuttle 14. The lower pusher 76 can then push the shuttle 14 through the lower track 148, out the lower jaw tip shuttle port 256 and into the upper jaw tip shuttle port 240.

When the shuttle 14 is pushed from the upper track 264 to the lower track 148 or vice versa, the shuttle 14 can be curvilinearly translated 282, as shown by arrow, following the paths of the upper track 264 and the lower track 148.

When the jaws are in a closed configuration, the shuttle 14 can move from the upper jaw 78 to the lower jaw 80, as shown by arrow, back to the upper jaw 78, and can repeat the motion from the upper jaw 78 to the lower jaw 80, and optionally from the lower jaw 80 to the upper jaw 78 one, two or more times.

The device 188 can have a pusher lockout that can prevent translation of the pushers and the shuttle 14 when the jaws are in an open configuration.

The device 188 can have a jaw lockout preventing opening of the jaws when either of the pushers is extended out of the respective jaw tip shuttle port and/or when the shuttle 14 is concurrently in the upper jaw 78 and the lower jaw 80.

Figure 8A:
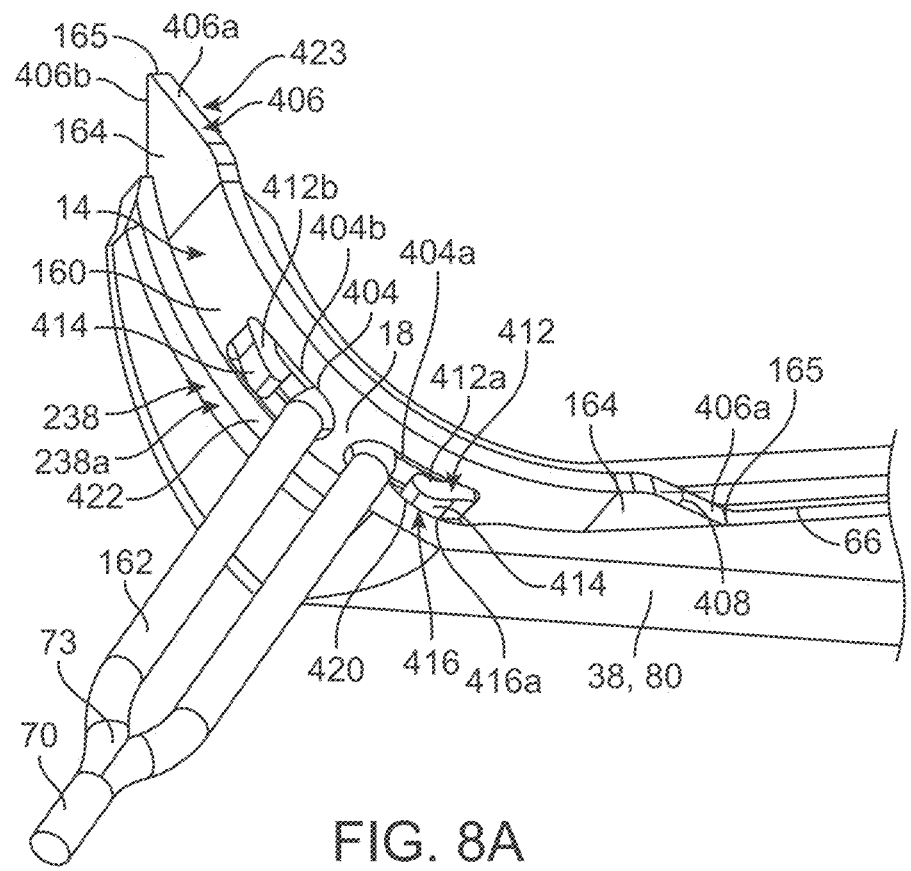
FIG. 8A illustrates a variation of the shuttle in a lower jaw with half the lower jaw shown transparent.

FIG. 8A illustrates that the suture holder 18 can be attached to or integrated with the shuttle 14. For example, the suture holder 18 can be a bridge integrated with the shuttle spine 160. A portion of the shuttle spine 160 can define the suture holder 18. As another example, the suture holder 18 can be removably attached to the shuttle 14. The suture holder 18 can extend between a shuttle first lateral side and a shuttle second lateral side. The suture holder 18 can extend between a shuttle first longitudinal side and a shuttle second longitudinal side. The suture holder 18 can be in the longitudinal center of the shuttle 14, on a proximal end of the shuttle 14, or on a distal end of the shuttle 14. A center of the suture holder 18 can be in the transverse center of the shuttle 14, on a first lateral side of the shuttle, or on a second lateral side of the shuttle. The suture holder 18 can be in the plane of the shuttle spine 160, extend away from the plane of the shuttle spine 160, or both. For example, FIG. 8A illustrates that the suture holder 18 does not extend away from the plane of the shuttle spine 160. The plane of the suture holder 18 can be flush with or coincident with the plane of the shuttle spine 160. This can advantageously allow the shuttle and suture holder 14, 18 to take up less space, thereby minimizing the trauma to surrounding tissue as the shuttle 14 is passed between the upper and lower jaws 30, 38 since it brings the base of the suture 70 closer to the shuttle 14. With the suture 70 closer to the shuttle 14, the force of the suture 70 against surrounding tissue is reduced as compared to when the suture 70 is connected to a structure out of the plane of the shuttle spine 160 (e.g., the suture holder 18 of FIGS. 5A and 5B). The shuttle and suture holder 18 can be a monolithic structure. The suture loop 162 can extend around and completely or partially circumscribe the suture holder 18. The remainder of the suture 70 can be integral with the suture loop 162, or can removably attached to the suture loop 162. The suture loop 162 can be attached to or integrated with the suture 70 at a suture junction 73. The suture junction 73 can be a knot, a braid, or both. The suture loop 162 can be circular, oval, or stadium-shaped.

The shuttle 14 can have zero, one, or multiple suture holes 404, for example, 0 to 4 or more suture holes 404, including every 1 suture hole increment within this range. For example, FIG. 8A illustrates that the shuttle 14 can have a first suture hole 404a and a second suture hole 404b. The shuttle holes 404 (e.g., first and second suture holes 404a, 404b) can have a regular or irregular shape, for example, curved, polygonal, or both. The suture holes 404 can be defined by one or more curved surfaces or curved edges, for example, one or more curved surfaces or curved edges of the shuttle 14. The suture holes 404 can be defined by one or more flat surfaces or straight edges, for example, one or more flat surfaces or straight edges of the shuttle 14. The suture holes 404 can have a cross-sectional shape of a circle, ellipse, rectangle, stadium, horseshoe, star, slot, or any combination thereof. The suture holes 404 can have such cross sectional shapes when the shuttle is curved or flat. The suture holes 404 can have a constant cross-sectional area or a tapered cross-sectional area.

The shuttle tips 164 can be beveled, non-beveled, or both. For example, FIG. 8A illustrates that the shuttle tips 164 can be non-beveled. The shuttle tips 164 can have one or multiple tip surfaces 406, for example, 1 to 4 or more tip surfaces 406, including every 1 tip surface increment within this range (e.g., 1 tip surface, 2 tip surfaces). For example, FIGS. 8A illustrates that the shuttle tips 164 can have a first tip surface 406a (e.g., a first non-beveled tip surface as shown in FIG. 8A) and a second tip surface 406b (e.g., a second non-beveled tip surface as shown in FIG. 8A). The non-beveled portion of the shuttle tips 164 can advantageously improve the force transfer from the upper and lower pushers 86, 76, thereby making it easier for the pushers 86 and 76 to push against the shuttle 14. A larger component of the force from the pushers (e.g., pushers 86 and 76) can be transferred along the longitudinal axis of the shuttle 14 when the shuttle tip 164 has a non-beveled surface 406 as compared to a beveled surface (e.g., the beveled surfaces shown in FIGS. 14a-14c). For beveled surfaces, a portion of the force applied to the shuttle 14 is directed against the surfaces that define the lower and upper tracks 66, 64 perpendicularly away from the beveled surface. When a pusher applies a longitudinal force against a beveled surface, a portion of the longitudinal force applied to the shuttle 14 by the pusher is transformed into a transverse component away from the longitudinal axis of the shuttle 14.

Figure 14A:
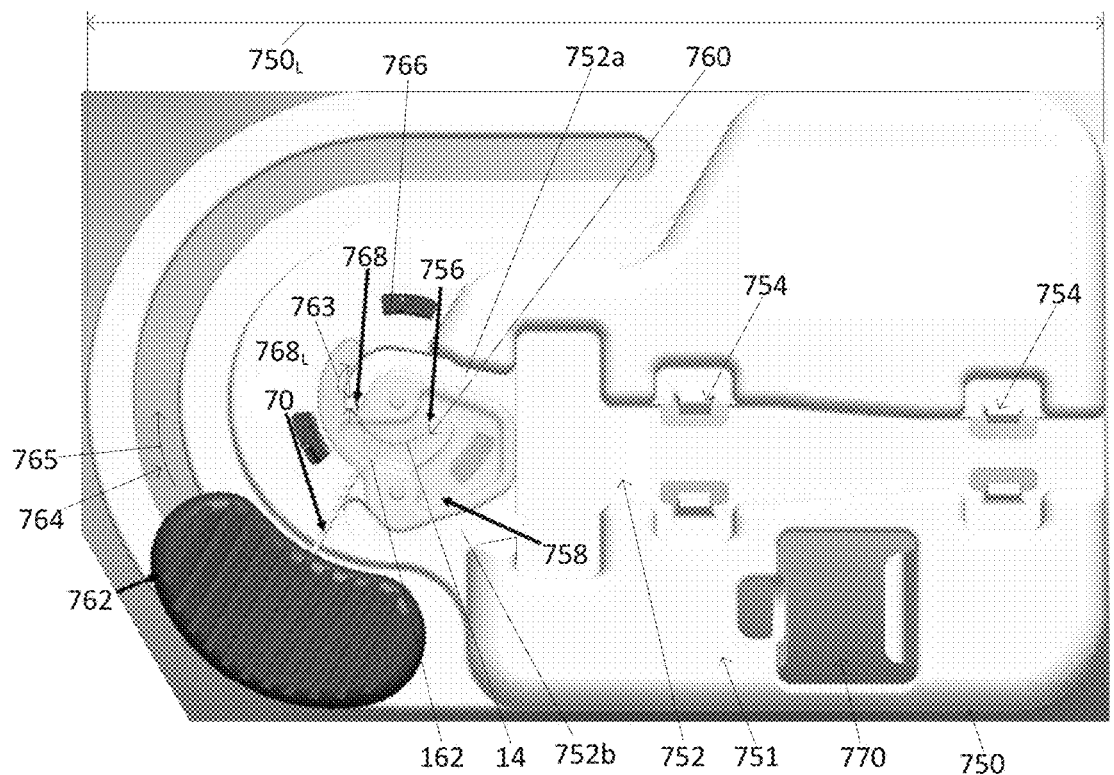
FIG. 14A illustrates a top view of a variation of a loader.
Figure 14B:
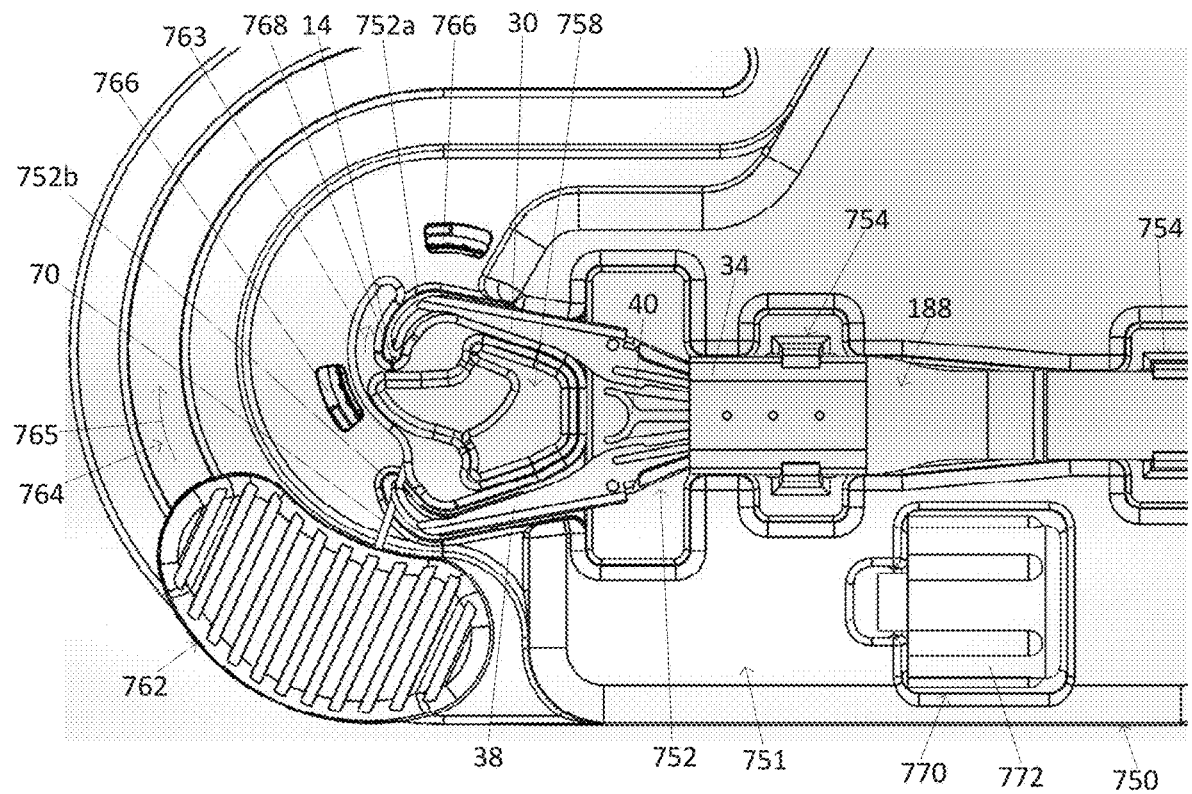
FIG. 14B illustrates a top view of a variation of a loader.
Figure 14C:
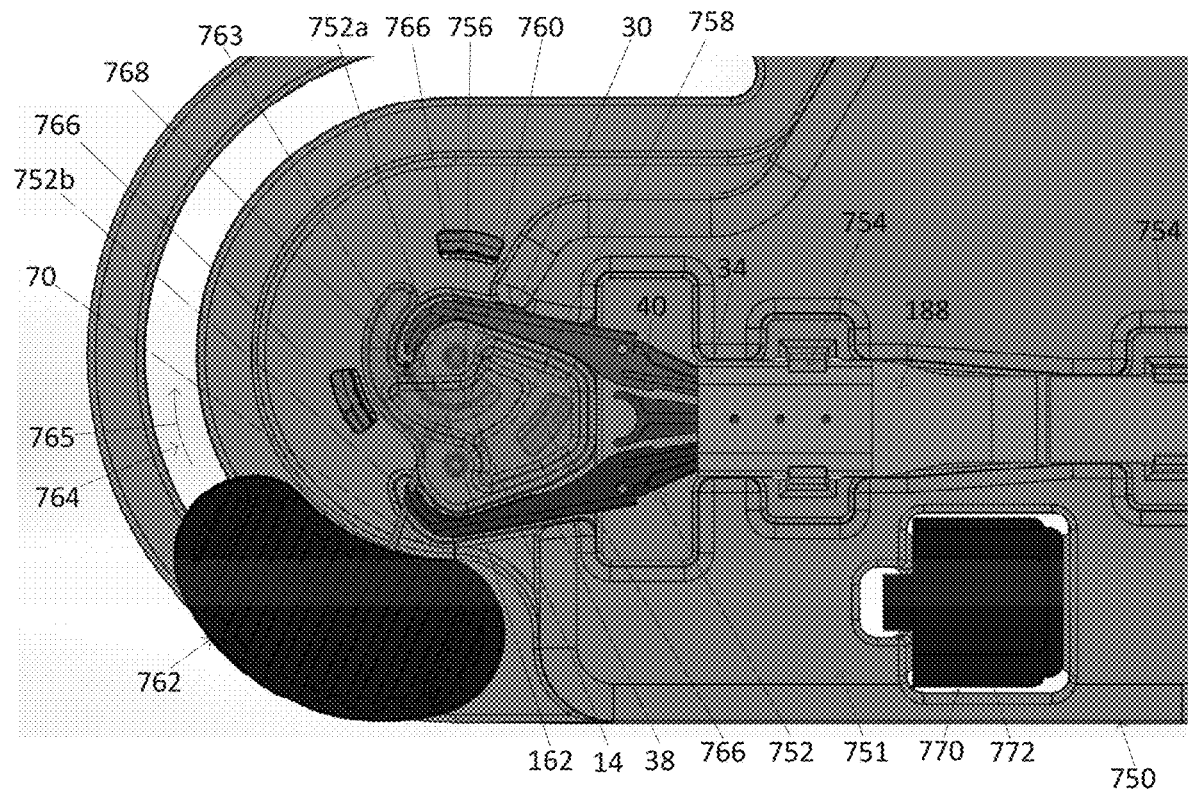
FIG. 14C illustrates a top view of a variation of a loader.

FIG. 8A further illustrates that the shuttle tips 164 can be tapered to form a terminal tip 165. The terminal tip 165 can be an edge or part of a rounded or flat surface. The tapered portion of the shuttle tip 164 can be a first bevel, for example, a first transverse bevel toward a longitudinal axis (e.g., center longitudinal axis) of the shuttle 14. The non-beveled surfaces 406 can thereby form first tissue cutting surfaces that are beveled in a first direction. The bevel referred to in the preceding paragraph can refer to a second bevel, for example, a second transverse bevel angled relative to a transverse axis perpendicular to the transverse axis of the first bevel and toward a longitudinal axis (e.g., center longitudinal axis) of the shuttle 14. Such a second bevel is shown in FIGS. 14a-14c. The second bevels can define second beveled surfaces along the taper that face a second direction different from the first direction. The second bevels can form second tissue cutting surfaces. The shuttle tips 164 can pierce or cut tissue. The tapered portion of the shuttle tips 164 can pierce or cut tissue. The tip surfaces 406 (e.g., tip surfaces 406a and 406b) can pierce or cut tissue. When the shuttle tips 164 have first and second bevels, the first and second bevels can pierce tissue or cut tissue. FIG. 8A illustrates that the shuttle tips 164 can be non-sharpened, meaning that while the edges are tapered to form a first cutting surface, the cutting surfaces 406 themselves can be chamfered or non-chamfered. The shuttle tips 164 can be non-sharpened and still cut or pierce tissue, where sharpened or non-sharpened can refer to the presence or non-presence of a second bevel (e.g., as shown in FIGS. 14a-14c), respectively.

FIG. 8A further illustrates that the device 188 can have one or multiple male stops 412 (also referred to as male catches, male detents, stops, catchers, detents) and one or multiple female stops 416 (also referred to as female catches, female detents, stops, catchers, detents). The device 188 can have, for example, 1-10 or more male stops 412, including every 1 male stop increment within this range (e.g., 1, 2, 3, 4 or more male stops). The device 188 can have, for example, 1-10 or more female stops 416, including every 1 female stop increment within this range (e.g., 1, 2, 3, 4 or more female stops).

The male stops 412 can be attached to or integrated with the device 188. For example, the male stops 412 can be part of, attached to, or integrated with the shuttle 14. As another example, the male stops 412 can be part of, attached to, or integrated with the jaws (e.g., jaws 30, 38, 78, 80). As yet another example, the device 188 can have some male stops 412 that are part of, attached to, or integrated with the shuttle 14 and can have some male stops 412 that are part of, attached to, or integrated with the jaws (e.g., jaws 330, 38, 78, 80). As yet still another example, the male stops 412 can be part of, attached to, or integrated with the pushers (e.g., the lower and upper pushers 76, 86).

The female stops 416 can be attached to or integrated with the device 188. For example, the female stops 416 can be part of, attached to, or integrated with the shuttle 14. As another example, the female stops 416 can be part of, attached to, or integrated with the jaws (e.g., jaws 330, 38, 78, 80). As yet another example, the device 188 can have some female stops 416 that are part of, attached to, or integrated with the shuttle 14 and can have some female stops 416 that are part of, attached to, or integrated with the jaws (e.g., jaws 330, 38, 78, 80). As yet still another example, the female stops 416 can be part of, attached to, or integrated with the pushers (e.g., the lower and upper pushers 76, 86).

FIGS. 8A-9B illustrate, for example, that the shuttle 14 can have the male stops 412 and that the jaws (e.g., jaws 330, 38, 78, 80) can have the female stops 416. For example, FIGS. 8A-9B illustrate that the shuttle 14 can have a first male stop 412a and a second male stop 412b, that the lower jaw (e.g., jaw 38, 80) can have a first female stop 416a (also referred to as the lower jaw first female stop 416a and other similar terms) configured to releasably engage with or releasably attach to the first male stop 412a, and that the upper jaw (e.g., jaw 30, jaw 78) can have a second female stop 416b (also referred to as the upper jaw first female stop 416b and other similar terms) configured to releasably engage with or releasably attach to the second male stop 412b. Half of the lower and upper jaws are shown transparent in FIGS. 8A-9B so that the shuttle 14 can be more easily seen in the jaw tracks (e.g., lower and upper tracks 66, 64), and so that the male and female stops 412, 416 can be more easily seen.

Each male stop 412 can releasably fit into, attach to, or engage with a corresponding female stop 416, for example, via a friction fit, snap fit, magnetic fit, ratchet fit, or any combination thereof. For example, the first male stop 412a can be configured to releasably attach to the first female stop 416a and the second male stop 412b can be configured to releasably attach to the second female stop 416b. When two stops (e.g., male and female stops 412, 416) are releasably attached to one another, a threshold release force can be required to release the stops from one another. The threshold release force can be from about 1.0 Newton to about 10.0 Newtons or more, including every 0.5 Newton increment within this range (e.g., 4.0 Newtons, 4.5 Newtons, 5.0 Newtons). As another example, the release force can be from about 0.5 lbs to about 1.5 lbs, including every 0.1 lb increment within this range (e.g., 1.0 lb).

The male stops 412 can be a positive feature such as a protrusion, bump, ridge, arm, extension, flexure, detent flexure, or any combination thereof. The male stops 412 can be straight and/or curved. The male stops 412 can be flexible, rigid, or both (e.g., a first portion can be flexible and a second portion can be rigid). The male stops 412 can be one or more springs. The female stops 416 can be a negative feature such as a void, space, pocket, notch, hole, through hole, recess, detent recess, or any combination thereof. The female stops 416 can be flexible, rigid, or both (e.g., a first portion can be flexible and a second portion can be rigid). The male and female stops 412, 416 can include magnets that attract one another to keep the male and female stops releasably attached together.

The male stops 412 can have a male surface 414 and the female stops 416 can have a female surface 418. The male and female surfaces 414, 418 can be configured to engage with one another, slidably engage with one another, contact one another other, or any combination thereof. The female stops 416 can have a lip 420 configured to engage with, slidably engage with, or contact the male stop 412, or any combination thereof. The male stops 412 can be configured to engage with, slidably engage with, or contact the lip 420, or any combination thereof.

For each male-female stop pair, the male and female surfaces 414, 418 can engage with one another and/or the male stop 412 can engage with the lip 420, for example, when the male stop 412 is being forced into the female stop 416, when the male stop 412 is being withdrawn from the female stop 416, when the female stop 416 is being forced over or onto the male stop 412, when the female stop 416 is being withdrawn from the male stop 412, when the male and female stops 412, 416 are attached to one another (also referred to as the stopped position, caught position, fixed position), or any combination thereof. As another example, two female stops 416 can engage with one another, for example, where the two female stops 416 include a magnet. As yet another example, two male stops 412 can engage with one another, for example, where the two male stops include a magnet. The male and/or female stops 412, 416 can form a hook or hook-like feature to releasably catch the other stop.

Figure 9A:
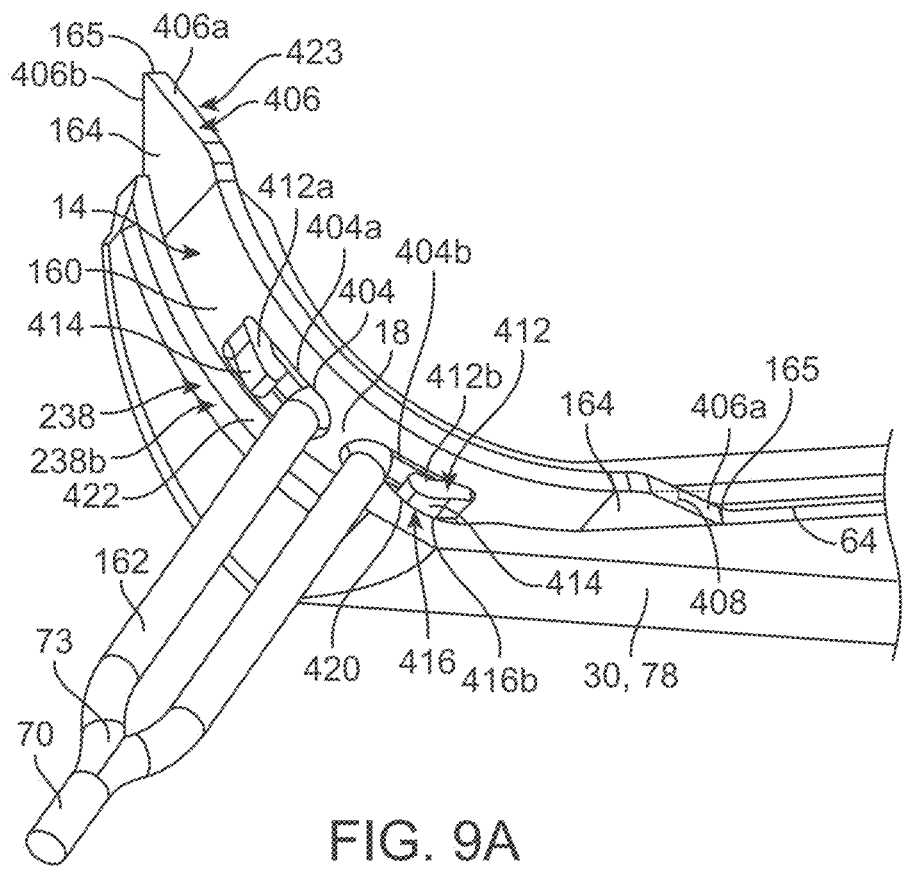
FIG. 9A illustrates a variation of the shuttle in an upper jaw with half the upper jaw shown transparent.

The male stops 412 can move relative to the female stops 416, vice versa, or both. The female stops 416 can move relative to the male stops 412, vice versa, or both. For example, FIG. 8A illustrates that the male stops 412 can be translatable (e.g., slidably translatable) in the lower jaw track, for example, in a first direction toward the first female stop 416a and in a second direction away from the first female stop 416a, or vice versa such that the first female stop 416a is translatable toward and away from a male stops 412 (e.g., for arrangements where the female stop 416 is integrated with or attached to the shuttle 14 and the male stop 412 is integrated with or attached to the lower jaw). As another example, FIG. 9A illustrates that the male stops 412 can be translatable (e.g., slidably translatable) in the upper jaw track, for example, in a first direction toward the second female stop 416b and in a second direction away from the second female stop 416b, or vice versa such that the second female stop 416b is translatable toward and away from a male stop 412 (e.g., for arrangements where the female stop 416 is integrated with or attached to the shuttle 14 and the male stop 412 is integrated with or attached to the upper jaw). The first and second directions can be opposite from one another.

Figure 8B:
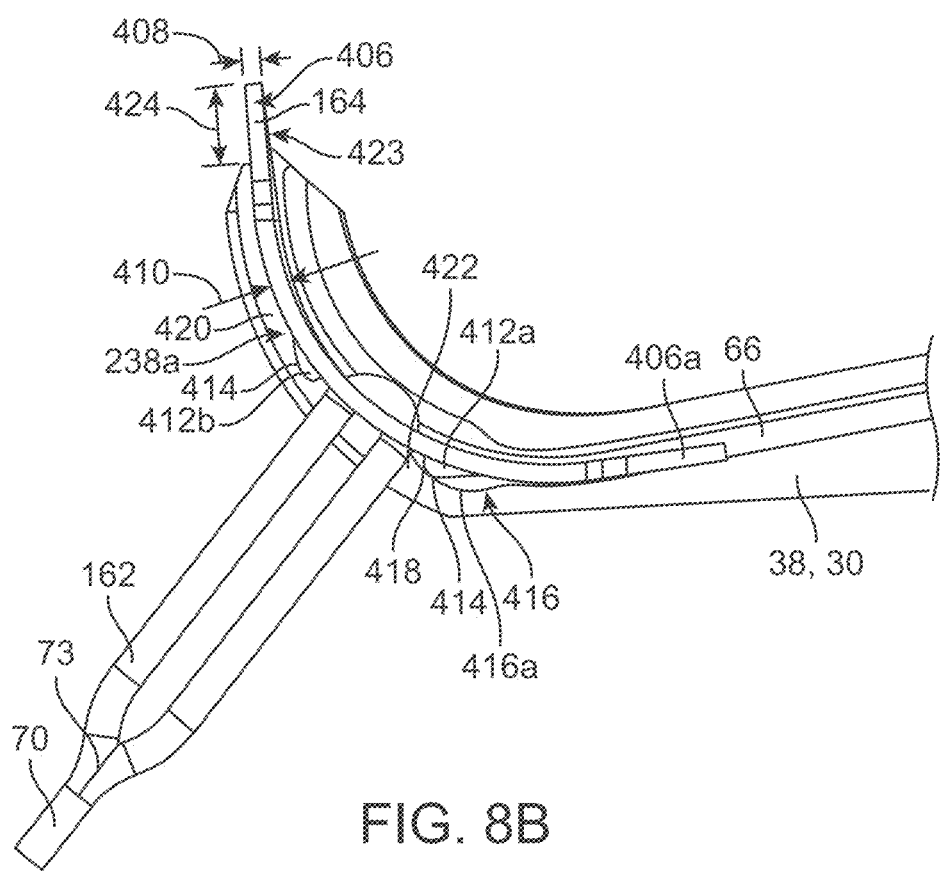
FIG. 8B illustrates a variation of the shuttle in a lower jaw with half the lower jaw shown transparent.

FIGS. 8A and 8B illustrate that when the shuttle 14 is being translated (e.g., pushed by the upper jaw pusher 86, pulled by the lower jaw pusher 76, or both) in a first direction in the lower jaw track toward the first female stop 416a, the lip 420 can exert a force against the first male stop 412a that causes the first male stop 412a to flex toward a longitudinal axis of the shuttle 14. This flexure can allow the first male stop 412a to fit into the first female stop 416a. Upon passing by the lip 420, the first male stop 412a can rebound to its neutral position or to a less flexed position and releasably lock the shuttle 14 to the lower jaw via the releasable attachment between the first male stop 412a and the first female stop 416a. FIGS. 8A and 8B further illustrate that when the shuttle 14 is being translated (e.g., pulled by the upper jaw pusher 86, pushed by the lower jaw pusher 76, or both) in a second direction (e.g., opposite the first direction) in the lower jaw track away from the first female stop 416a, the female surface 418 can exert a force against the first male stop 412a that causes the first male stop 412a to flex toward a longitudinal axis of the shuttle 14. This flexure can allow the first male stop 412a to slide under and past the lip 420. Upon passing by the lip 420 in the second direction, the first male stop 412a can rebound to its neutral position (also referred to as a non-flexed position). When the first male stop 412a flexes, it can deflect into the first suture hole 404a.

Figure 9B:
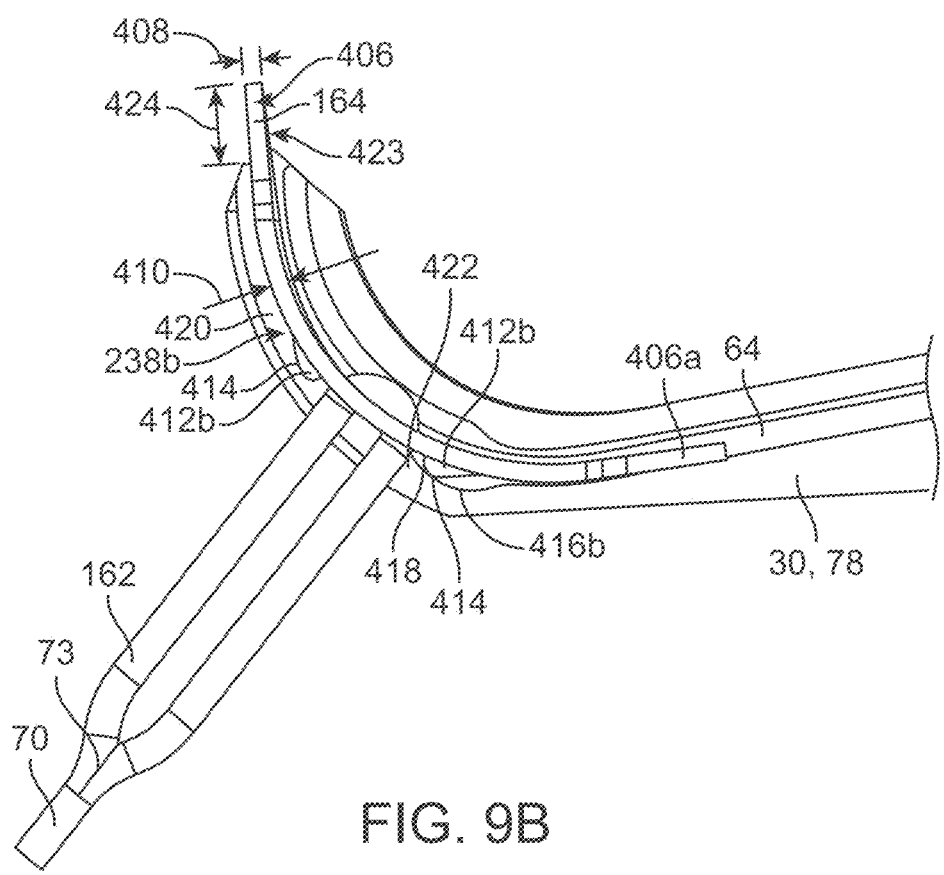
FIG. 9B illustrates a variation of the shuttle in an upper jaw with half the upper jaw shown transparent.

FIGS. 9A and 9B illustrate that when the shuttle 14 is being translated (e.g., pushed by the lower jaw pusher 76, pulled by the upper jaw pusher 76, or both) in a first direction in the upper jaw track toward the second female stop 416b, the lip 420 can exert a force against the second male stop 412b that causes the second male stop 412b to flex toward a longitudinal axis of the shuttle 14. This flexure can allow the second male stop 412b to fit into the second female stop 416b. Upon passing by the lip 420, the second male stop 412b can rebound to its neutral position or to a less flexed position and releasably lock the shuttle 14 to the upper jaw via the releasable attachment between the second male stop 412b and the second female stop 416b. FIGS. 9A and 9B further illustrate that when the shuttle 14 is being translated (e.g., pushed by the upper jaw pusher 86, pulled by the lower jaw pusher 76, or both) in a second direction (e.g., opposite the first direction) in the upper jaw track away from the second female stop 416b, the female surface 418 can exert a force against the second male stop 412b that causes the second male stop 412b to flex toward a longitudinal axis of the shuttle 14. This flexure can allow the second male stop 412b to slide under and past the lip 420. Upon passing by the lip 420 in the second direction, the second male stop 412b can rebound to its neutral position (also referred to as a non-flexed position). When the first male stop 412a flexes, it can deflect into the second suture hole 404b.

The lip 420 can resist passage of the first and second male stops 412a, 412b along the second direction out of the first and second female stops 416a, 416b with the threshold release force. The female surface 418 can be an inner surface of the lip 420. The lip 420 can resist passage of the first and second male stops 412a, 412b along the first direction into the first and second female stops 416a, 416b with the threshold release force or a lesser force (e.g., a force 10% to 75% of the threshold release force).

The device 188 can have zero, one, or multiple male stops 412 and zero, one, or multiple female stops 416 on the device distal end 2 (e.g., closer to the jaws than to the handle 104) and/or on the device proximal end (e.g., closer to the handle 104 than to the jaws). For example, the upper jaw (e.g., upper jaw 78) can have one or multiple male stops 412, one or multiple female stops 416, or any combination thereof. The lower jaw (e.g., lower jaw 80) can have one or multiple male stops 412, one or multiple female stops 416, or any combination thereof. The male and/or female stops 412 and/or 416 can be attached to or integrated with the jaw, the jaw track, or both. The shuttle 14 can have one or multiple male stops 412, one or multiple female stops 416, or any combination thereof. The male stops 412 can extend away from and/or toward a longitudinal axis of the shuttle 14. The male stops 412 can extend away from and/or toward a longitudinal axis of a jaw track (e.g., tracks 66 and 64). The female stops 416 can extend away from and/or toward a longitudinal axis of the shuttle 14. The female stops 416 can extend away from and/or toward a longitudinal axis of a jaw track (e.g., tracks 66 and 64).

For example, FIG. 8A illustrates that the shuttle 14 can have a first male stop 412a and a second male stop 412b, and that the lower and upper jaw tracks (e.g., tracks 66 and 64) can each define a female stop 416 (e.g., a first female stop 416a in the lower jaw and a second female stop 416b in the upper jaw). The lower and upper jaws can each define one or multiple female stops 416. For example, the first male stop 412a can releasably attach to the first female stop 416a and the second male stop 412b can releasably attach to a second female stop 416b. FIG. 8A illustrates that the first and second male stops 412a, 412b can extend away from a longitudinal axis (e.g., center longitudinal axis) of the shuttle toward a longitudinal center of the shuttle 14. The first and second male stops 412a, 412b can be the same or a different dimension away from the longitudinal center of the shuttle 14 as the other detent.

FIGS. 8A-9B further illustrate a surface 422 of jaw suture slots 238, for example, lower jaw suture slot 238a and upper jaw suture slot 238b.

FIGS. 8B and 9B illustrate that the shuttle tips 164 can have a shuttle tip thickness 408 of about 0.05 mm to about 0.75 mm, including every 0.05 mm increment within this range (e.g., 0.15 mm, 0.20 mm, 0.25 mm). The shuttle tip thickness 408 can be the width of the non-beveled surfaces 406. As another example, the shuttle tip thickness 408 can be from about 0.0080 in. to about 0.0090 in. (e.g., 0.0085 in.).

FIGS. 8B and 9B further illustrate that the shuttle 14 can have a shuttle thickness 410 (also referred to as the shuttle thickness $14_T$) of about 0.05 mm to about 0.75 mm, including every 0.05 mm increment within this range (e.g., 0.15 mm, 0.20 mm, 0.25 mm). The shuttle tip thickness 408 can be the same or different from the shuttle thickness 410. The shuttle tip thickness 408 can be less than, equal to, or greater than the shuttle thickness 410. For example, the shuttle tip thickness 408 can be about 0.15 mm and the shuttle thickness 410 can be about 0.25 mm, or vice versa.

The shuttle 14 can be made from a single panel of material (e.g., metal). The suture holes 404 can be cut, leaving the shuttle 14 and the male stops 412. The shuttle 14 can then be bent, which can result in the male stops 412 extending out of the plane of the shuttle spine 160.

FIGS. 8A-9B further illustrate that a portion 423 of the shuttle tips 164 can remain exposed outside of the jaws when the shuttle 14 is fully translated into the jaws. The exposed portion 423 can have an exposed length 424, for example, from about 0.25 mm to about 5.00 mm or more, including every 0.25 mm increment within this range (e.g., 0.50 mm, 1.00 mm, 1.50 mm). The exposed portion 423 can align the lower and upper jaws when they close. The exposed portion 423 can pierce tissue when the lower and upper jaws are closed against each other and before the shuttle 14 is translated to the other jaw. This can advantageously leverage the clamping force of the jaws to cut tissue with the shuttle 14. A portion of the exposed portion 423 can pierce tissue when the shuttle 14 is translated from the lower jaw to the upper jaw, or vice versa.

Figure 10:
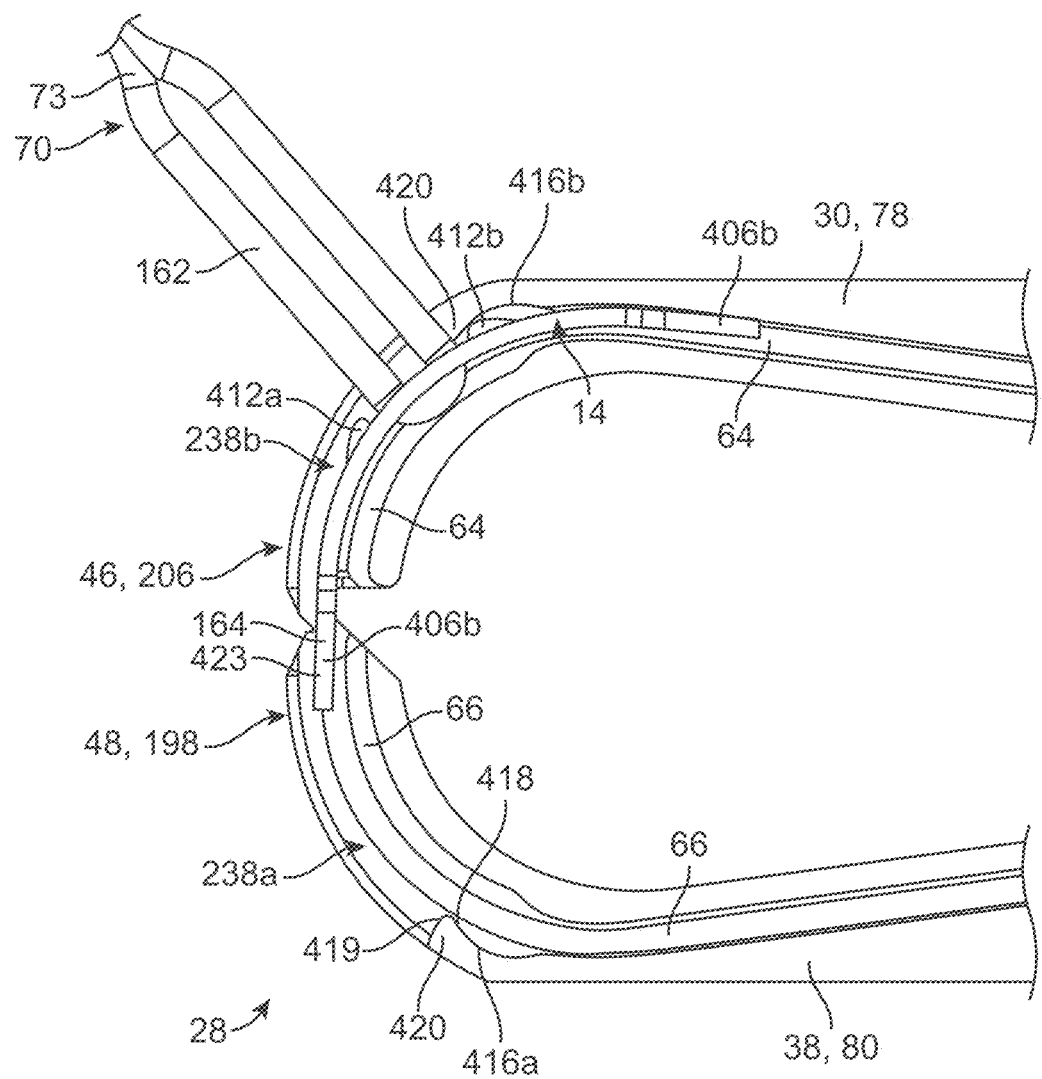
FIG. 10 illustrates a variation of the device with half the lower and upper jaws shown transparent.

FIG. 10 illustrates that all or a portion of the exposed portion 423 can be in the other jaw when the lower and upper jaws are closed and before the shuttle 14 is translated to the other jaw via the lower or upper pusher 76, 86. For example, when the jaws are moved from an open configuration to a closed configuration with the exposed portion 423 extending from the upper jaw (e.g., jaw 30, jaw 78) as shown in FIGS. 8A and 8B, the exposed portion 423 can be moved into the lower jaw (e.g., jaw 38, jaw 80) via the jaws closing with or without translation (e.g., simultaneous translation) of the shuttle 14 into the lower jaw via an upper and/or lower pusher while the jaws are being closed.

FIG. 10 further illustrates that the female stops 416 can have an outer surface 419 and an inner surface 418 (also referred to as a female surface). The outer surface 419 can be flat or curved. The outer surface 419 can define a ramp surface for the male stops 412 to flex against. The outer surface 419 can define a plane at an angle to a longitudinal axis of the shuttle. For example, the plane of the outer surface 419 can be perpendicular or substantially perpendicular to the center longitudinal axis of the shuttle. The inner surface can be flat or curved. The inner surface 418 can define a ramp surface for the male stops 412 to flex against.

FIG. 10 further illustrates that when the lower and upper jaws are closed the jaws can define a continuous track for the shuttle 14 such the lower jaw track 66 and the upper jaw track 64 are continuous with one another. The tracks of the upper jaw and bottom jaw can form a continuous path when the jaw structure 28 is in a closed configuration.

FIG. 10 further illustrates that the first jaw tip (e.g., jaw tip 46, jaw tip 206) can be configured to interdigitate with the second jaw tip (e.g., jaw tip 48, jaw tip 198). For example, the first jaw tip can interdigitate with and be adjacent or in contact with the second jaw tip when the jaw structure 28 is in a closed configuration. The jaw tips can be sharpened. The jaw tips can be tapered. The jaw tips can be sharp and seat into each other to form a continuous track when the jaw structure 28 is in a closed configuration. The jaw tips can seat into each other to connect the lower and upper jaw tracks 66, 64 to each other.

Figure 11A:
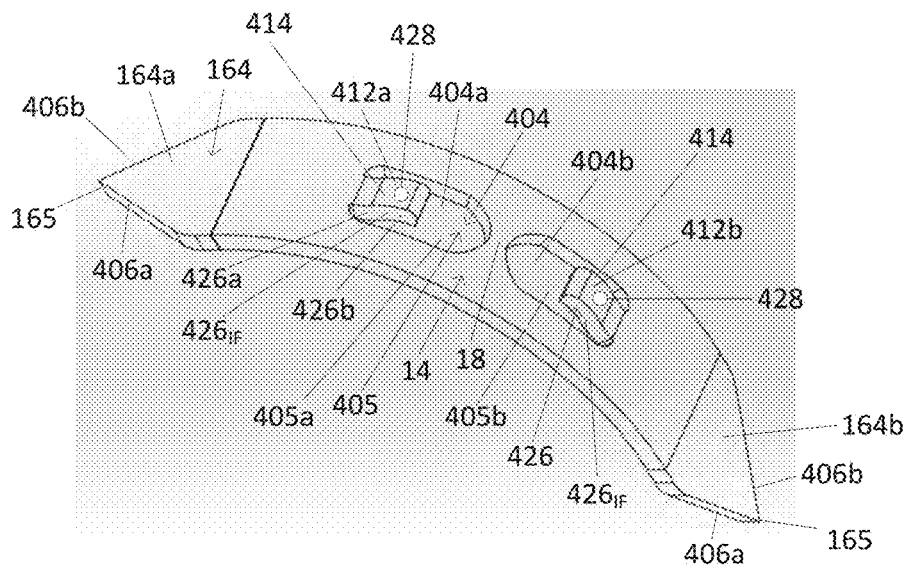
FIG. 11A illustrates a perspective view of a variation of a shuttle.

FIG. 11A illustrates that the shuttle 14 can have a shuttle first tip 164a and a shuttle second tip 164b.

FIG. 11A further illustrates that the shuttle 14 can have zero, one, or multiple shuttle holes 405, for example, 1 to 6 or more shuttle holes 405, including every 1 shuttle hole increment within this range (e.g., 2 shuttle holes, 4 shuttle holes). The shuttle 14 can have a first shuttle hole 405a and a second shuttle hole 405b. The shuttle holes 405 (e.g., holes 405a and 405b) can be the same as or different from the suture holes 404 (e.g., holes 404a and 404b). The male and/or female stops 412, 416 can move into and out of the shuttle holes 405, the suture holes 404, or any combination thereof, for example, via flexing, bending, translating, and/or rotating into and out of the holes 405 and/or 404.

FIG. 11A further illustrates that the male stops 412 can have one or multiple bends 426. For example, FIG. 11A illustrates that the male stops 412 can have a first bend 426a and a second bend 426b. The male stops 412 can have inflection points $426_{IF}$ where the curvature of the male stop 412 changes direction or its concavity. For example, FIG. 11A illustrates that the male stops 412 can have an inflection point $426_{IF}$ between two bends 426 (e.g., between the first and second bends 426a, 426b) where the male stops 412 change concavity (e.g., from concave up for the first bend 426a to concave down for the second bend 426b as shown in FIG. 11A).

FIG. 11A further illustrates that one or more magnets 428 can be attached to or integrated with the male stops 412 on a first side of the detents, for example, on or under the first surface 414 (also referred to as a male surface). The magnets 428 can be configured to be magnetically attracted to a magnet attached to or integrated with the upper or lower jaw having an opposite dipole as the magnets 428.

Figure 11B:
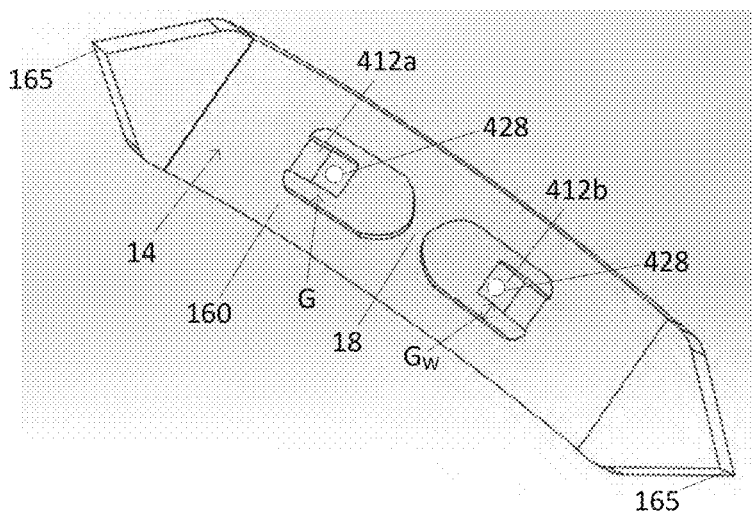
FIG. 11B illustrates a bottom view of the shuttle of FIG. 11A.

FIG. 11B illustrates that the one or more magnets 428 can be attached to or integrated with a second surface 415 of the male stops 412, for example, to an underside of the male stops 412.

FIG. 11B further illustrates that there can be a gap G on each side of the male stop 412 between the male stop 412 and the shuttle body 160. The gap G can advantageously inhibit or prevent pressure from forming in the jaws by allowing gas, liquid, or solids to flow or pass through the gap G as the shuttle 14 is advanced into the jaws. There can be a gap on each lateral side of the male stop 412 as shown in FIG. 11B. As another example, there may not be any gaps G between the male stops 412 and the shuttle body 160, or the gap G can be on only one side of the male stop 412 instead of both sides as shown in FIG. 11B. The gaps G can have a gap width $G_W$ that can be, for example, constant (e.g., as shown in FIG. 11B) or tapered. As another example, the gaps G can have multiple gap widths $G_W$. For example, FIG. 11B further illustrates that the gap G can have a constant width, for example, as measured between the lateral edge or surface of the male stop 412 and the lateral edge or surface of the shuttle body 160.

FIG. 11B further illustrates that the terminal tips 165 can have a sharpened edge. The sharpened edge can be configured to pierce tissue.

Figure 11C:
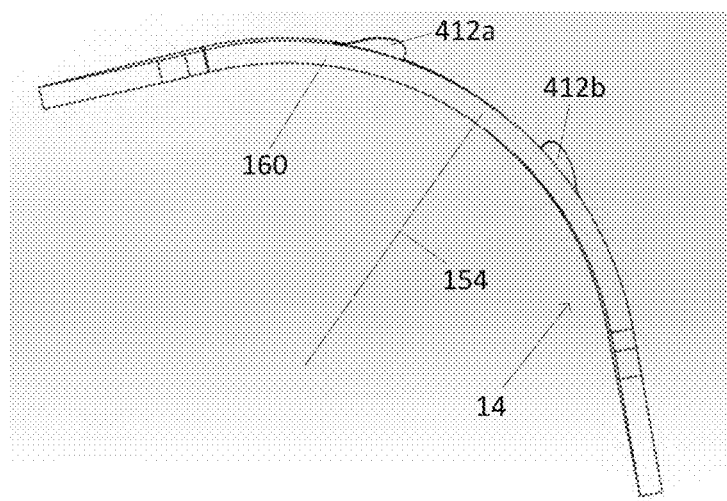
FIG. 11C illustrates a side view of the shuttle of FIG. 11A.

FIG. 11C illustrates that the male stops 412 (e.g., first and second male stops 412a, 412b) can extend away from a longitudinal axis of the shuttle 14 out of the plane of the shuttle spine 160.

The shuttle longitudinal axis (e.g., longitudinal axis 157) can be flat or curved. FIG. 11C illustrates that the shuttle radius of curvature 154 can be from about 2.00 mm to about 5.00 mm or more, including every 0.01 mm increment within this range (e.g., 2.84 mm).

The shuttle 14 can be straight or have a preformed bend or curve (e.g., having the radius of curvature 154). The shuttle 14 can have a preformed bend having a radius of curvature of about 40% to about 200% of the radius of curvature 154, including every 1% increment within this range (e.g., 50%).

The curvature of the shuttle 14 can be constant. The curvature of the shuttle 14 can be fixed. The shuttle 14 can be flexible. The shuttle 14 can be rigid. The shuttle 14 can transition between curved and straight configurations. Having a preformed bend within this range can reduce the strain on the shuttle 14. For example, the strain can be reduced for variations where the shuttle 14 shifts between straight and curved configurations when moving within and/or between the jaws.

Figure 12A:
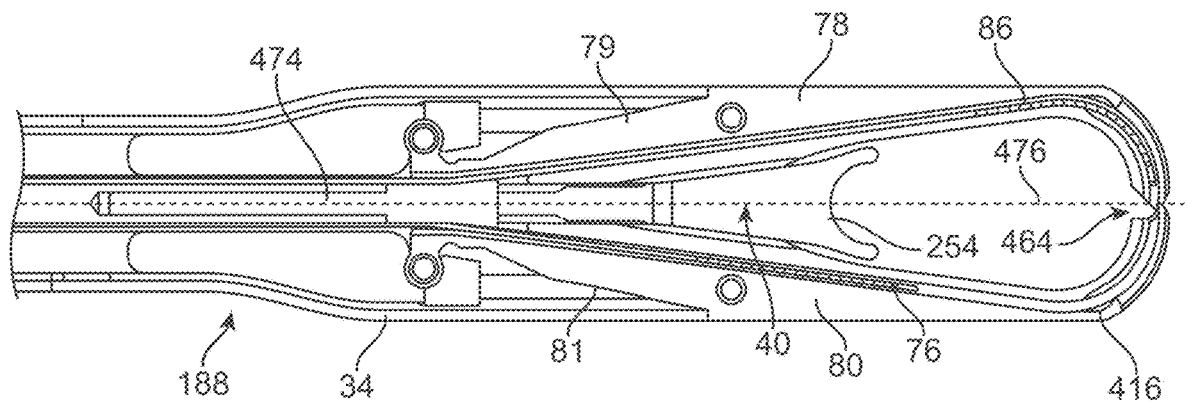
FIG. 12A illustrates a side view of a variation of the device with half the device shown transparent.
Figure 12B:
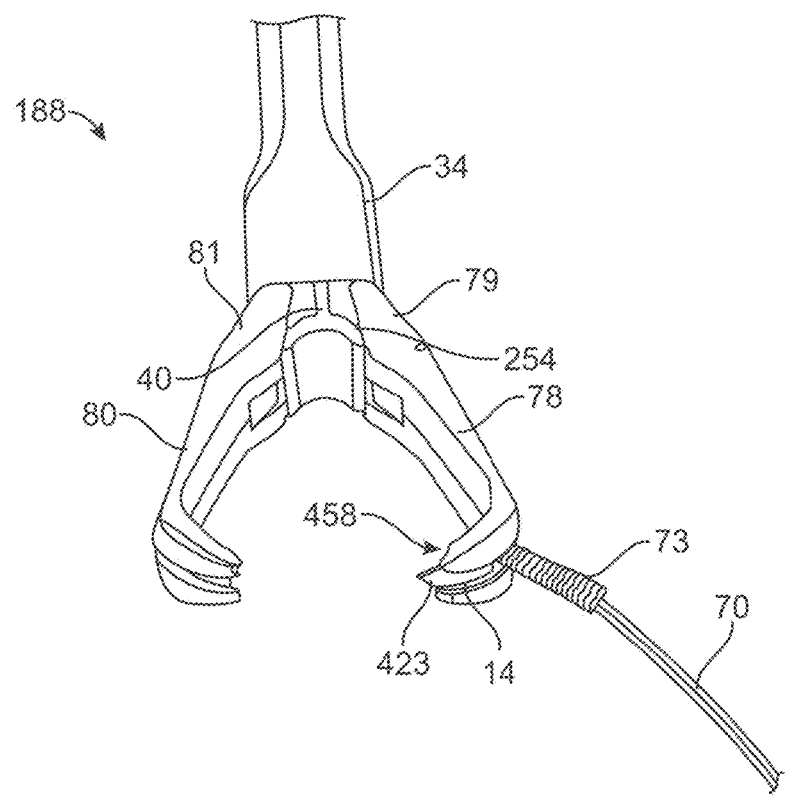
FIG. 12B illustrates a perspective view of the device of FIG. 12A.

FIGS. 12A and 12B illustrate a variation of the device 188 in a fully closed and fully open configuration, respectively.

FIGS. 12A and 12B illustrate that the jaw control extension 40 can be fixed and that the jaws 78 and 80 can move relative to the jaw control extension 40. For example, the jaws 78 and 80 can move distally and proximally against the jaw control extension 40 to open and close, respectively. The jaws 78 and 80 can move longitudinally along a device longitudinal axis 476. The jaws 78 and 80 can move into and out of the compression cover 34. The jaws 78 and 80 can be attached to a tube 474 connected to the handle controls that can translate (e.g., slidably translate) the jaws 78 and 80 into and out of the compression cover 34. FIGS. 12A and 12B illustrate that the compression cover 34 can engage with an upper jaw surface 79 and a lower jaw surface 81 to force the jaws closed when the jaws 78 and 80 are translated proximally toward the handle and into the compression cover 34. Movement of the jaws 78 and 80 in a first direction (e.g., distal movement) against the jaw control extension 40 can cause the jaws to open and move from the closed configuration shown in FIG. 12A to the open configuration shown in FIG. 12B. Movement of the jaws 78 and 80 in a second direction (e.g., proximal movement) against the compression cover 34 can cause the jaws to close and move from the open configuration shown in FIG. 12B to the closed configuration shown in FIG. 12A. The first and second directions can be opposite from one another. As another example, the jaws can be fixed and the jaw control extension can move relative to the jaws. The compression cover 34 can be longitudinally fixed or longitudinally movable.

The extension head 254 can have the shape shown such that the jaws open relative to each other when the jaws are moved out of the compression cover 34 over the extension head 254.

FIG. 12A illustrates the device 188 without a shuttle 14 for illustrative purposes and FIG. 12B illustrates the device 188 of FIG. 12A with a shuttle 14.

Figure 13A:
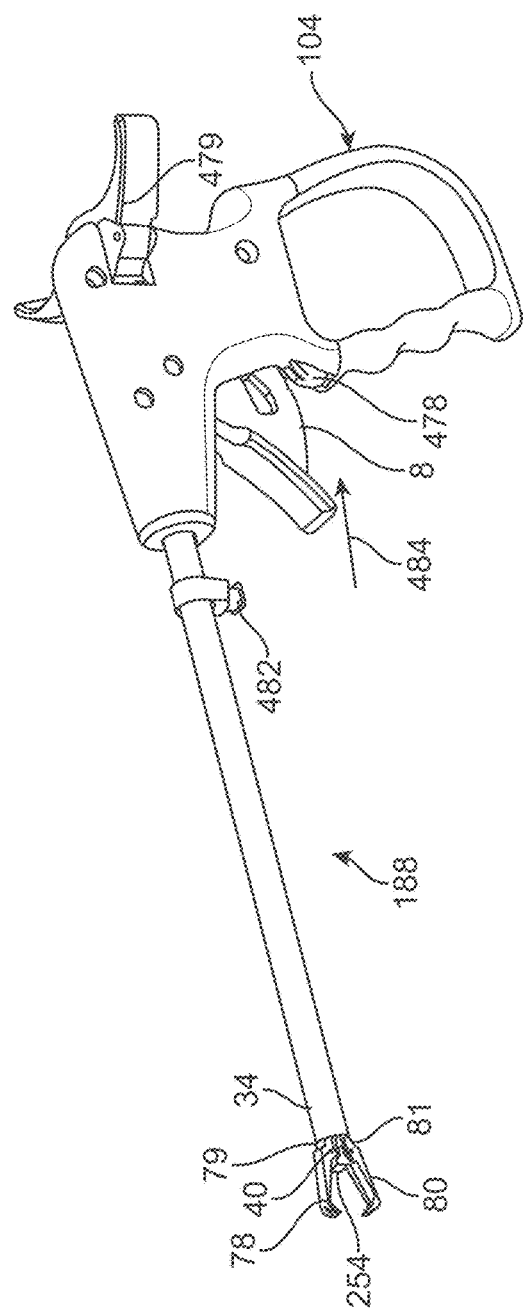
FIG. 13A illustrates a variation of the device.
Figure 13B:
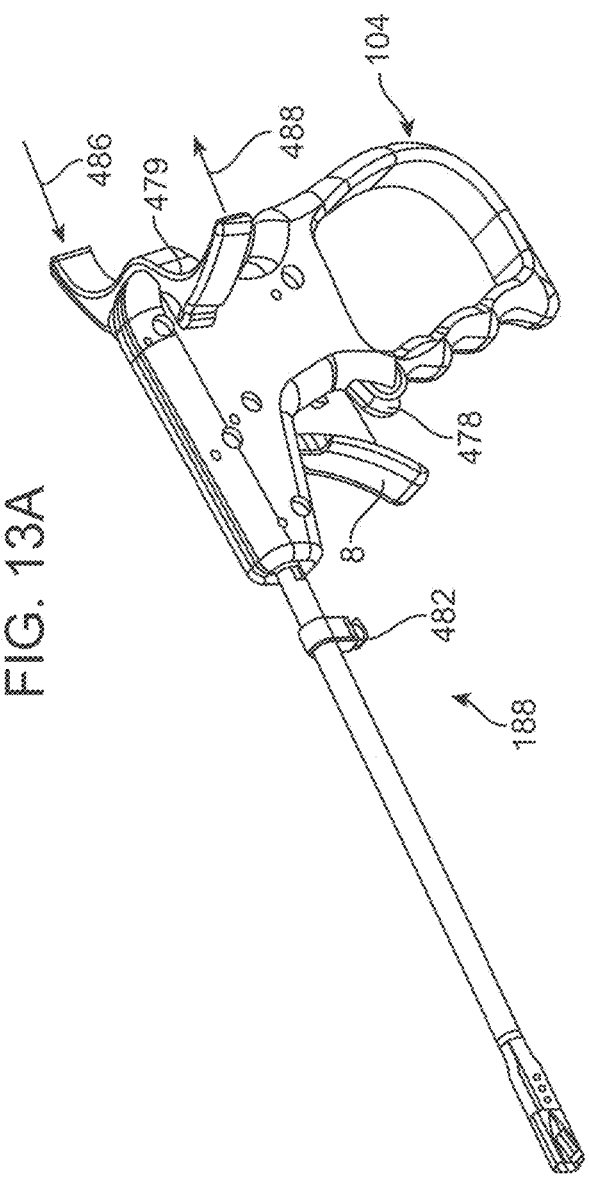
FIG. 13B illustrates a variation of the device.

FIGS. 13A and 13B illustrate a variation of the device 188 in a fully opened and fully closed configuration, respectively.

FIGS. 13A and 13B illustrate that the handle 104 can have a jaw control 8 (also referred to as a trigger), a jaw control release 478 and a shuttle control 479. The jaw control 8 can be pulled with one or more fingers in direction 484 to move the jaw control 8 to the configuration shown in FIG. 13B. The jaw control 8 can translate and/or rotate. When the jaw control 8 is moved in direction 484, the jaws 78 and 80 can move from an open configuration to a less open configuration (e.g., to the closed configuration shown in FIG. 13B). When the jaw control 8 is moved in a direction opposite to direction 484, the jaws 78 and 80 can move from a closed configuration to an open configuration (e.g., from the closed configuration in FIG. 13B to the fully open configuration illustrated in FIG. 13A).

As another example, the handle 104 can have a first press button configured to close the jaws when pressed and a second press button configured to open the jaws when pressed.

The jaw control release 478 can be a press button, a switch, a knob, or any combination thereof. The jaw control 8 can lock when the jaws 78 and 80 are in the fully closed configuration. Activating the jaw control release 478 can release the jaw control 8 from the lock position. The jaw control release 478 can be activated, for example, by pressing it. Upon pressing the jaw control release 478, the jaw control 8 can be manually returned to the position shown in FIG. 13A to fully open the jaws, or the jaw control 8 can automatically return to the position shown in FIG. 13A.

The shuttle control 479 can be a button, switch, knob, or any combination thereof. For example, FIGS. 13A and 13B illustrate that the shuttle control 479 can be a switch that can pivot. The shuttle control 479 can be locked when the jaws 78 and 80 are in the open configuration of FIG. 13A. When the jaws are closed, the shuttle control can be rotated in direction 486 and direction 488. Directions 486 and 488 can be directed opposite from one another. When the shuttle control 479 is moved in (e.g., rotated) in direction 486, the upper pusher 86 can move the shuttle 14 to the lower jaw 80. When the shuttle control 479 is moved in (e.g., rotated) in direction 488, the lower pusher 76 can move the shuttle 14 to the upper jaw 78. The shuttle control 479 can have a batwing shape, which can provide ergonomic benefits.

As another example, the handle 104 can have a first press button configured to move the upper pusher 86 when pressed and a second press button configured to move the lower pusher 76 when pressed.

FIGS. 13A and 13B further illustrate that the device 188 can have a flush port 482 having a luer connection. A cleaning fluid (e.g., enzyme cleaner) can be flushed through the device through the flush port 482 to clean it.

FIG. 13C illustrates that the shuttle control 479 can have a neutral position. When the shuttle control 479 is in the neutral position, one or neither of the pushers 76 and 86 can be in contact with the shuttle 14. When the shuttle control 479 is in the neutral position, the shuttle 14 can be ejected from the jaws.

FIG. 13D illustrates the shuttle control 479 in a fully advanced position when moved in direction 486. When in the shuttle control 479 is in the fully advanced position in direction 486, the upper pusher 86 can be in a fully advanced position and the lower pusher 76 can be in a fully retracted position. For example, the upper pusher 86 can be fully advanced toward the lower jaw 80, thereby pushing the shuttle 14 into the lower jaw 80. The upper pusher 86 can push the shuttle 14 into the lower jaw 80 to the point where detents on the shuttle 14 (male and/or female stops 412, 416) releasably engage with detents on the lower jaw 80 (male and/or female stops 412, 416).

FIG. 13E illustrates the shuttle control 479 in a fully advanced position when moved in direction 488. When in the shuttle control 479 is in the fully advanced position in direction 488, the lower pusher 76 can be in a fully advanced position and the upper pusher 86 can be in a fully retracted position. For example, the lower pusher 76 can be fully advanced toward the upper jaw 78, thereby pushing the shuttle 14 into the upper jaw 78. The lower pusher 76 can push the shuttle 14 into the upper jaw 78 to the point where detents on the shuttle 14 (male and/or female stops 412, 416) releasably engage with detents on the upper jaw 78 (male and/or female stops 412, 416).

The upper and lower jaws referred to throughout the application can be any of the upper and lower jaws disclosed, illustrated, and/or contemplated herein. For example, the upper and lower jaws 30, 48 can be the upper and lower jaws 78, 80, respectively. As another example, the upper jaw 30 can be interchangeable with the upper jaw 78, and the lower jaw 38 can be interchangeable with the upper jaw 80. As yet another example, the upper jaw 30 can also be referred to as the upper jaw 78, and the lower jaw 38 can also be referred to as the lower jaw 80. The lower jaw can be a first jaw and the upper jaw can be a second jaw. The lower jaw can be a second jaw and the upper jaw can be a first jaw.

The upper and lower jaw tracks referred to throughout the application can be any of the upper and lower jaw tracks disclosed, illustrated, and/or contemplated herein. For example, the upper and lower jaw tracks 64, 66 can be the upper and lower jaw tracks 264, 148, respectively. As another example, the upper jaw track 64 can be interchangeable with the upper jaw track 264, and the lower jaw track 66 can be interchangeable with the upper jaw track 264. As yet another example, the upper jaw track 64 can also be referred to as the upper jaw track 264, and the lower jaw track 66 can also be referred to as the lower jaw track 148. The lower jaw track can also be referred to as the lower track, and the upper jaw track can also be referred to as the upper track.

FIG. 14A illustrates a variation of a shuttle loader 750 (also referred to as a loader) that can load the shuttle 14 into the device 188, for example, into the upper jaw 30 or into the lower jaw 38. The loader 750 can have a loader body 751 that can have a device space 752. The device 188 can be removably positionable in the device space 752. The device space 752 can be one or multiple spaces. For example, FIG. 14A illustrates that the device space 752 can be a recess in the loader body 751. The spaces can be recesses, grooves, depressions, or available space on the loader 750. FIG. 14A illustrates that the device space 752 can include a first jaw space 752a and a second jaw space 752b. For example, FIG. 14A illustrates that the first jaw space 752a can be a recess and that the second jaw space 752b can be a recess. The upper jaw 30 jaw can be placed in the first jaw space 752a and the lower jaw 38 can be placed in the second jaw space 752b. As another example, the lower jaw 38 jaw can be placed in the first jaw space 752a and the upper jaw 30 can be placed in the second jaw space 752b. The device 188 can be placed in the device space 752 in a partially open configuration or a fully open configuration. For example, FIG. 14A illustrates that the upper and lower jaws 30, 38 can be positionable in the first and second jaw spaces 752a, 752b when the jaws 30 and 38 are in a fully open configuration.

FIG. 14A further illustrates that the loader 750 can have one or multiple holders 754 that can hold the device 188 and the loader 750 together. For example, FIG. 14A illustrates that the holders 754 can hold the device 188 in the device space 752. The holders 754 can be, for example, clips, clasps, magnets, or fasteners, clasps, catches, pins, or any combination thereof. For example, FIG. 14A illustrates that the holders 754 can be clips that the device 188 can be snapped into when the device 188 is placed in the device space 752. As another example, the device space 752 can be sized and shaped to form an interference fit (also referred to as a friction fit) with the device 188 when the device 188 is in the device space 752.

FIG. 14A further illustrates that the loader 750 can have a loader body shuttle track 756 (also referred to as the shuttle track 756 or the track 756). The track 756 can be a track in the loader body 751. The track 756 can be a groove in the loader body 751. The track 756 can be a channel in the loader body 751. The track 756 can have the same radius of curvature as the shuttle 14. The shuttle 14 can be in the shuttle track 756 or can be positionable in the shuttle track 756. For example, FIG. 14A illustrates that the loader 750 can be packaged with the shuttle 14 positioned in the shuttle track 756 in the arrangement shown.

The shuttle 14 can be moveable (e.g., translatable, slideable) in the track 756. The shuttle 14 can be longitudinally moveable along the track 756. For example, the shuttle 14 can be translatable or slideable along the track 756. The shuttle 14 can be moveable out of (e.g., longitudinally out of) the track 756, for example, into the upper jaw track 64 or into the lower jaw track 66. For example, the shuttle 14 can have a shuttle first position and a shuttle second position. The shuttle 14 can be moveable from the shuttle first position to the shuttle second position. The shuttle 14 can be moved from the shuttle first position to the shuttle second position, for example, in a first direction 763 along the track 756. The shuttle 14 can be moved from the shuttle first position to the shuttle second position to load the device 188 with the shuttle 14. When the shuttle 14 is in the shuttle first position, the shuttle 14 can be in the track 756. When the shuttle 14 is in the shuttle second position, the shuttle 14 can be in the upper jaw 30 or in the lower jaw 38, for example, in the upper jaw track 64 or in the lower jaw track 66. When the shuttle 14 is in the shuttle second position, the shuttle 14 can be in or above the first jaw space 752a. For example, FIG. 14A illustrates that the shuttle first position can be the shuttle 14 in the track 756. The shuttle first position can be the home position (also referred to as the neutral position) of the shuttle 14. The loader 750 can be packaged with the shuttle 14 in the shuttle first position. The shuttle second position can be a shuttle loaded position (e.g., a fully loaded position, a partially loaded position) of the shuttle 14.

A fully loaded position of the shuttle 14 can be the position of the shuttle 14 when, for example, the shuttle 14 is in the device 188 (e.g., is in the upper jaw 30 or in the lower jaw 38) and a male stop 412 is engaged with another male stop 412 or with a female stop 416. Where the device 188 does not have any stops, the fully loaded position of the shuttle 14 can be, for example, when the shuttle 14 is in the device 188 (e.g., is in the upper jaw 30 or in the lower jaw 38) to an extent where the upper and lower jaws 30, 38 can be closed (e.g., fully closed) with the shuttle 14 in the device 188.

A partially loaded position of the shuttle 14 can be any position of the shuttle 14 between the shuttle first position and a fully loaded position of the shuttle 14. For example, a partially loaded position of the shuttle 14 can be, for example, when the shuttle 14 is in the device 188 (e.g., is in the upper jaw 30 or in the lower jaw 38) but before a male stop is engaged with another male stop 412 or with a female stop 416. Where the device 188 does not have any stops, a partially loaded position of the shuttle 14 can be, for example, when the shuttle 14 is in the device 188 (e.g., is in the upper jaw 30 or in the lower jaw 38) but the upper and lower jaws 30, 38 cannot be closed with the shuttle 14 in the device 188 (e.g., because the shuttle 14 is inhibiting or preventing the jaws 30 and 38 from being closed), or the jaws 30 and 38 can be partially closed but the shuttle 14 prevents the jaws 30 and 38 from being fully closed.

FIG. 14A further illustrates that the loader 750 can have the suture 70, the suture loop 162, or both. The suture 70 can be attached to the shuttle 14 or can be attachable to the shuttle 14 with or without the suture loop 162. For example, FIG. 14A illustrates that the loader 750 can be packaged with the suture 70 and the suture loop 162 in the arrangement shown, with the suture loop 162 attached to the shuttle 14. When the device 188 is in the device space 752, the shuttle 14 can be loaded into the device 188.

FIG. 14A further illustrates that the loader 750 can have a cap 758. The cap 758 can be opaque or transparent. For example, FIG. 14A illustrates that the cap 758 can be transparent. A transparent cap 758 can advantageously allow the user to observe the loading process, for example, so that the user can see whether or not the shuttle 14 is properly loading into the device 188 during the loading process. A transparent cap 758 can advantageously allow the user to inspect the shuttle 14 prior to loading the shuttle 14 into the device 188. The cap 758 can keep the shuttle 14 in the shuttle track 756. The cap 758 can have a cap shuttle track 760 (also referred to as the shuttle track 760 or the track 760) that can mate with the shuttle track 756. The cap 758 can be attached to the loader body 751, for example, with glue. As another example, the cap 758 can be removably attached to the loader body 751. The cap 758 can define a portion of the device space 752. The cap 758 can have a finger $758_F$ (also referred to as an extension). The finger $758_F$ can constrain or guide movement of the shuttle 14 in the first jaw space 752a. The finger $758_F$ can define a side wall of the first jaw space 752a. The finger $758_F$ can constrain or guide the device 188 when in the first jaw space 752a.

FIG. 14A further illustrates that the loader 750 can have a loader control 762 and a loader control track 764 (also referred to as the track 764). The loader control 762 can be, for example, a moveable button, a moveable knob, a moveable toggle, a moveable switch, a moveable slide, a translator, a rotator, a slider, or any combination thereof. The loader control 762 can have an ergonomic shape, for example, the shape shown in FIG. 14A. For example, FIG. 14A illustrates that the loader control 762 can have a bean shape (e.g., a kidney bean shape) when viewed from a top view. The loader control 762 can be translatable and/or rotatable. For example, FIG. 14A illustrates that the loader control 762 can be a moveable button. The track 764 can be, for example, a track, a channel, a groove, or a through channel of the loader body 751, or any combination thereof. For example, FIG. 14A illustrates that the track 764 can extend through the loader body 751. The loader control 762 can be moveable (e.g., translatable, slideable) in and/or along the loader control track 764. The loader control 762 can have a loader control first position and a loader control second position. The loader control 762 can be moveable from the loader control first position to the loader control second position. The loader control 762 can be moved from the loader control first position to the loader control second position, for example, in a first direction 765 along the track 764. The loader control first position can be at a first end of the track 764. The loader control second position can be at the first end of the track 764, or at a second end of the track 764. For example, FIG. 14A illustrates that the loader control first position can be at a first terminal end of the track 764. The loader control first position can be the home position (also referred to as the neutral position or a non-loaded position) of the loader control 762. The loader 750 can be packaged with the loader control 762 in the loader control first position, with the suture loop 162 attached to the shuttle 14. The loader control second position can be at a second terminal end of the track 764 or any position along the track 764 between the first and second terminal ends of the track 764. The loader control second position can be a loader control loaded position (e.g., a fully loaded position, a partially loaded position). For example, the loader control first position can be a non-loaded position of the loader control 762, the loader control positions between the loader control first and second positions can be loader control partially loaded positions of the loader control 762, the loader control second position can be a fully loaded position of the loader control 762, and the loader control positions beyond the loader control second position (e.g., along the track 764 in direction 765) can be loader control over-loaded positions of the loader control 762.

A fully loaded position of the loader control 762 can be the position of the loader control 762 when, for example, the shuttle 14 is in the device 188 (e.g., is in the upper jaw 30 or in the lower jaw 38) and a male stop 412 is engaged with another male stop 412 or with a female stop 416. Where the device 188 does not have any stops, the fully loaded position of the loader control 762 can be, for example, when the shuttle 14 is in device 188 (e.g., is in the upper jaw 30 or in the lower jaw 38) to an extent where the upper and lower jaws 30, 38 can be closed (e.g., fully closed) with the shuttle 14 in the device 188.

A partially loaded position of the loader control 762 can be any position of the loader control 762 between the loader control first position and a fully loaded position of the loader control 762. For example, a partially loaded position of the loader control 762 can be, for example, when the shuttle 14 is in the device 188 (e.g., is in the upper jaw 30 or in the lower jaw 38) but before a male stop is engaged with another male stop 412 or with a female stop 416. Where the device 188 does not have any stops, a partially loaded position of the loader control 762 can be, for example, when the shuttle 14 is in the device 188 (e.g., is in the upper jaw 30 or in the lower jaw 38) but the upper and lower jaws 30, 38 cannot be closed with the shuttle 14 in the device 188 (e.g., because the shuttle 14 is inhibiting or preventing the jaws 30 and 38 from being closed), or the jaws 30 and 38 can be partially closed but the shuttle 14 prevents the jaws 30 and 38 from being fully closed.

The loader control 762 can be moveable from the loader control first position to the loader control second position to move the shuttle 14 into the device 188, for example, to move the shuttle 14 from the shuttle first position to the shuttle second position. To load the shuttle 14 into the device 188, the loader control 762 can be moved (e.g., pushed, pulled, pushed and pulled) from the loader control first position to the loader control second position or to a loader control third position beyond the loader control second position. The loader control third position can be any position beyond the loader control second position, and can include, for example, the position of the loader control 762 at the second terminal end of the track 764.

When the loader control 762 is in the loader control first position, the shuttle 14 can be in the shuttle first position. When the loader control 762 is in the loader control second position, the shuttle 14 can be in the shuttle second position. When the loader control 762 is in the loader control third position, the shuttle 14 can be in the shuttle second position. Moving the loader control 762 from the loader control first position to the loader control second position can move the shuttle 14 from the shuttle first position to the shuttle second position or can cause the shuttle 14 to move from the shuttle first position to the shuttle second position. For example, when the loader control 762 is moved from the loader control first position to the loader control second position, the loader control 762 can pull the suture 70 which can in turn pull the shuttle 14. As the loader control 762 is moved in the first direction 765, for example, from the loader control first position to the loader control second position, the suture 70 between the shuttle 14 and the loader control 762 can be in tension. In this way the loader control 762 can move the shuttle 14 by moving the suture 70. As another example, the loader control 762 can be directly attached (e.g., directly removably attached) to the shuttle 14. As yet another example, the loader control 762 can be the suture 70 itself.

As the loader control 762 is moved from the loader control first position to the loader control second position, the shuttle 14 can be moved along the loader body shuttle track 756, along the cap shuttle track 760, along the first jaw space 752a, along a jaw track (e.g., the upper jaw track 64 or the lower jaw track 66), or any combination thereof. For example, when the loader 750 is used to load the upper jaw 30 with the shuttle 14, the shuttle 14 can be moved along the loader body shuttle track 756 and the cap shuttle track 760 into the upper jaw track 64. When the shuttle 14 is in the upper jaw track 64, the shuttle can be in or above the first jaw space 752a. When the shuttle 14 is in the shuttle second position in the upper jaw 30, the loader control 762 can be in the loader control second position and the shuttle 14 can be fully loaded into the upper jaw track 64 (e.g., the shuttle 14 can be in a fully loaded position in the upper jaw track 64). As another example, when the loader 750 is used to load the lower jaw 38 with the shuttle 14, the shuttle 14 can be moved along the loader body shuttle track 756 and the cap shuttle track 760 into the lower jaw track 66. When the shuttle 14 is in the lower jaw track 66, the shuttle can be in or above the first jaw space 752a. When the shuttle 14 is in the shuttle second position in the lower jaw 38, the loader control 762 can be in the loader control second position and the shuttle 14 can be fully loaded into the lower jaw track 66 (e.g., the shuttle 14 can be in a fully loaded position in the upper jaw track 64).

When the loader control 762 is in the loader control second position, the shuttle 14 can be fully loaded into the device 188. Once the loader control 762 is in the loader control second position, the loader control 762 can be moveable to the loader control third position, for example, to help make sure the shuttle 14 is fully loaded into the device 188 by the loader control 762 and/or to let the user know that the shuttle 14 is fully loaded into the device 188. As the loader control is moved from the loader control second position to the loader control third position, the shuttle 14 may or may not move farther into the device 188 (e.g., into the upper jaw 30 or into the lower jaw 38), for example, into a shuttle third position. The shuttle third position can be an overloaded position of the shuttle 14 in the device 188. For example, when the loader control 762 is in the loader control second position and the shuttle 14 is in the shuttle second position fully loaded into the device 188, moving the loader control 762 to the loader control third position can cause the loader 750 to provide tactile and/or audible feedback to the user (e.g., audible clicks, movement of the suture 70 through or around the loader control 762, an audible slipping sound as the suture 70 is pulled through or around the loader control 762) which can indicate that the shuttle 14 is fully loaded into the device 188.

The loader control 762 can be moveable along the track 764 from the loader control first position to the loader control second position in discrete steps (e.g., stopping at one or more intermediate positions between the loader control first and second positions) and/or in one continuous movement, for example, in direction 765 (e.g., the direction toward the second terminal end of the track 764 along the track 764, for example, the direction along the track 764 from the first terminal end of the track 764 to the second terminal end of the track 764). The loader control 762 can be moved along the track 764 from the loader control first position to the loader control second position in discrete steps (e.g., stopping at one or more intermediate positions between the loader control first and second positions) and/or in one continuous movement, for example, in direction 765 (e.g., the direction toward the second terminal end of the track 764 along the track 764, for example, the direction along the track 764 from the first terminal end of the track 764 to the second terminal end of the track 764).

The loader control 762 can be moveable along the track 764 from the loader control first position to the loader control third position in discrete steps (e.g., stopping at one or more intermediate positions between the loader control first and second positions and/or stopping at one or more intermediate positions between the loader control second and third positions) and/or in one continuous movement, for example, in direction 765 (the direction along the track from the first terminal end of the track 764 to the second terminal end of the track 764). The loader control 762 can be moved along the track 764 from the loader control first position to the loader control third position in discrete steps (e.g., stopping at one or more intermediate positions between the loader control first and second positions and/or stopping at one or more intermediate positions between the loader control second and third positions) and/or in one continuous movement, for example, in direction 765 (the direction along the track from the first terminal end of the track 764 to the second terminal end of the track 764).

The loader control 762 can be moveable along the track 764 in a direction opposite to direction 765 (e.g., the direction toward the first terminal end of the track 764 along the track 764, for example, the direction along the track 764 from the second terminal end of the track 764 to the first terminal end of the track 764). The loader control 762 can be moved toward the first terminal end of the track 764, for example, to partially or fully unload the shuttle 14 from the device 188 back into the track 756. The shuttle 14 can be partially or fully unloaded from the upper jaw 30 or from the lower jaw 38, for example, if there was an error or malfunction during loading such as the shuttle 14 being misaligned with the upper or lower jaw 30, 38 or such as the suture 70 prematurely slipping through the loader control 762. As another example, the shuttle 14 can be partially or fully unloaded from the device 188 if when the loader control is in the loader control second position or in the loader control third position, the shuttle 14 is in a partially loaded position between the shuttle first and second positions. Once the shuttle 14 is partially or fully unloaded from the device 188 by moving the loader control 762 in toward the first terminal end of the track 764 (e.g., in a direction opposite to direction 765), the shuttle 14 can be loaded or reloaded into the device 188 with or without making adjustments to the loader 750 and/or the device 188. For example, after the shuttle 14 is unloaded from the device 188, the positions of the suture 70 and/or the shuttle 14 can be repositioned, as needed, so that the loader control 762 can load the shuttle 14 into the device 188. For example, if a portion of the suture 70 is extending across the track 756 after the shuttle is unloaded, the suture 70 can be moved away from the track 756 so that the suture 70 does not block or inhibit the shuttle 14 from moving along the track 756 and into the device 188 as the loader control 762 is moved from the loader control first position to the loader control second position.

FIG. 14A further illustrates that the loader 750 can have a suture holder 766. The suture holder 766 can be, for example, a suture spool. The suture 70 can have a length of about 3 cm to about 150 cm, including every 1 cm increment within this range (e.g., 3 cm, 4 cm, 40 cm, 150 cm). The suture holder 766 may or may not hold suture, depending on the length of the suture. For example, where the suture holder 766 is a suture spool, the suture holder 766 may or may not have suture 70 wound around it. The loader 750 can be packaged with any length of suture. For example, FIG. 14A illustrates that the loader 750 can be packaged with a suture 70 having a length of 4 cm. For a suture length of 4 cm, the suture holder 766 may or may not hold any of the suture 70. As another example, FIG. 14A illustrates that the loader 750 can be packaged with a suture 70 having a length of 40 cm. For a suture length of 40 cm, the suture holder 766 can hold some of the suture 70 (e.g., where the suture holder 766 is a spool, some of the suture 70 can be wound around the suture holder 766). As the shuttle 14 is loaded into the device 188, for example, by moving the loader control 762 from the loader control first position to the loader control second position, the suture 70 on the suture holder 766 can be pulled from the suture holder 766. When the suture 70 is pulled from the suture holder 766, the suture 70 can, for example, unwind or unfold from the suture holder 766. FIG. 14A illustrates, for example, that the suture holder 766 can be seen through holes in the loader body 751.

The suture 70 can be a first suture. A first end of the suture 70 can be connected to the shuttle 14 (e.g., via the suture loop 162) and a second end of the suture 70 can be connected to a second suture, for example, to an implantable suture. The second end of the suture 70 can have a loop that can be attachable to the second suture.

FIG. 14A further illustrates that the cap 758 can be on a first side of the loader 750 and that the suture holder 766 can be on a second side of the loader 750. The first and second sides of the loader 750 can be opposite to each other. For example, FIG. 14A illustrates that the cap 758 can be on a front side of the loader 750 and that the suture holder 766 can be on the back side of the loader 750.

FIG. 14A further illustrates that the suture 70 can extend from the shuttle 14 under the cap 758 to the loader control 762, can extend through the loader control 762 from a first side of the loader 750 to a second side of the loader 750, and can extend from the loader control 762 to the suture holder 766.

FIG. 14A further illustrates that the device 188 can be placed in the device space 752 with the upper jaw 30 in the first jaw space 752*a* with the upper and lower jaws 30, 38 in an open configuration (e.g., in a partially open configuration or in a fully open configuration). For example, FIG. 14A illustrates that the upper and lower jaws 30, 38 can be positionable in the first and second jaw spaces 752*a,* 752*b,* respectively (or vice versa) when the upper and lower jaws 30, 38 are in a fully open configuration. When the upper and lower jaws 30, 38 are positioned in the first and second jaw spaces 752*a,* 752*b,* respectively (or vice versa), the upper and lower jaws 30, 38 can be closeable against the cap 758. For example, when the upper and lower jaws 30, 38 are positioned in the first and second jaw spaces 752*a,* 752*b,* respectively (or vice versa) in an open configuration, the upper and lower jaws 30, 38 can be partially closed against the cap 758, for example, by moving the jaw control 8 in direction 484 (e.g., by pulling the jaw control 8). When the upper and lower jaws 30, 38 are partially closed against the cap 758, the upper and lower jaws 30, 38 can be clamped against the cap 758. Closing the jaws against the cap 758 can advantageously stabilize the device 188 in the device space 752. Closing the jaws against the cap 758 can advantageously align the shuttle 14 with the jaw track that is in the first jaw space 752*a* (e.g., the upper jaw track 64 or the lower jaw track 66). As another example, when the upper and lower jaws 30, 38 are positioned in the first and second jaw spaces 752*a,* 752*b,* respectively (or vice versa), the upper and lower jaws 30, 38 can be clampable against the cap 758. For example, when the upper and lower jaws 30, 38 are positioned in the first and second jaw spaces 752*a,* 752*b,* respectively (or vice versa) in an open configuration, the upper and lower jaws 30, 38 can be clamped against the cap 758 by moving the jaws into a partially closed configuration (e.g., by moving the jaw control 8 in direction 484). Clamping the jaws against the cap 758 can advantageously stabilize the device 188 in the device space 752. Clamping the jaws against the cap 758 can advantageously align the shuttle 14 with the jaw track that is in the first jaw space 752*a* (e.g., the upper jaw track 64 or the lower jaw track 66).

FIG. 14A further illustrates that when the shuttle 14 is in the shuttle first position (e.g., in the position shown in FIG. 14A), a portion 768 (also referred to as the exposed portion 768) of one of the shuttle tips 164 can extend from the cap 758. The portion 768 can be the portion of the shuttle 14 that extends out from under the cap 758 when the shuttle 14 is in the shuttle first position. The portion 768 can remain exposed outside of the cap 758 when the shuttle is in the shuttle first position. The exposed portion 768 can have an exposed length 768$_L$, for example, from about 0.15 mm to about 5.00 mm or more, including every 0.25 mm increment within this range (e.g., 0.15 mm, 1.00 mm, 1.50 mm, 5.00 mm). As another example, the exposed length 768$_L$ can be the same as the exposed length 424.

When the jaws are in a partially closed configuration (e.g., with or without being clamped against the cap 758), all or a portion of the exposed portion 768 may not be in the jaw that is in the first jaw space 752*a* (e.g., the upper jaw 30 or the lower jaw 38). As another example, as the upper and lower jaws 30, 38 are partially closed against the cap 758, the jaw in the first jaw space 752*a* (e.g., the upper jaw 30 or the lower jaw 38) can close onto all or a portion of the exposed portion 768. The exposed portion 768 can align the jaw (e.g., the upper jaw 30 or the lower jaw 38) in the first jaw space 752*a* during loading, for example, as the jaw in the first jaw space 752*a* closes onto the exposed portion 768. For example, the device 188 can be placed in the device space 752 with the upper jaw 30 in the first jaw space 752*a* with the upper and lower jaws 30, 38 in an open configuration (e.g., in a partially open configuration or in a fully open configuration). When the jaws are in a partially closed configuration against the cap 758, all or a portion of the exposed portion 768 can be in the jaw that is in the first jaw space 752*a* (e.g., the upper jaw 30 or the lower jaw 38). When the shuttle 14 is in the shuttle first position and the jaws are closed against the cap 758, all or a portion of the exposed portion 768 can be in the jaw that is in the first jaw space 752*a* (e.g., the upper jaw 30 or the lower jaw 38). The exposed portion 768 can align the jaw that is in the first jaw space 752*a* as the upper and lower jaws 30, 38 are closed together against the cap 758. This can advantageously leverage the clamping force of the jaws to load the shuttle 14 into the device 188 (e.g., into the upper jaw 30 or into the lower jaw 38). When the shuttle 14 is in the shuttle second position, the portion 423 of the shuttle tip 164 can remain exposed outside of the jaw that is in the first jaw space 752*a*. In this way, a first side of the shuttle 14 can have the exposed portion 768 when the shuttle 14 is in the shuttle first position, and a second side of the shuttle 14 can have the exposed portion 423 when the shuttle 14 is in the shuttle second position. As another example, when the shuttle 14 is in the shuttle first position and the jaws are closed against the cap 758 and/or against the loader body 751, all or a portion of the exposed portion 768 can be outside of the jaw that is in the first jaw space 752*a* (e.g., the upper jaw 30 or the lower jaw 38). For example, when the shuttle 14 is in the shuttle first position and the jaws are closed against the cap 758 and/or against the loader body 751, all or a portion of the exposed portion 768 can be in the track 756 and/or in the track 760. As another example, when the shuttle 14 is in the shuttle first position and the jaws are closed against the cap 758 and/or the loader body 751, a first portion of the exposed portion 768 can be in the track 756 and/or in the track 760, and a second portion of the exposed portion 768 can be in (e.g., can extend into) the first jaw space 752 with or without also extending into the device 188. As the jaws are closed against the cap 758 and/or against the loader body 751, the upper jaw 30 or the lower jaw 38 may or may not close onto the shuttle 14 (e.g., onto the exposed portion 768). In either case (e.g., the shuttle 14 is in the jaws when the jaws are clamped against cap 758 and/or the loader body 751, or the shuttle 14 is not in the jaws when the jaws are clamped against the cap 758 and/or the loader body 751), closing the jaws onto the cap 758 and/or onto the loader 751 can advantageously leverage the clamping force of the jaws to load the shuttle 14 into the device 188 (e.g., into the upper jaw 30 or into the lower jaw 38), for example, by stabilizing the device 188 in or on the loader 750. The shuttle 14 can be loaded into the device from the track 756 and/or from the track 760 with or without clamping the jaws onto the cap 758 and/or onto the loader body 751.

The shuttle 14 can be loaded into the device 188 with or without closing the jaws against the cap 758.

The first jaw space 752*a* and/or the second jaw space 752*b* can be sized and shaped to form an interference fit (also referred to as a friction fit) with the upper jaw 30 and/or the lower jaw 38 when the upper and lower jaws 30, 38 are in the device spaces 752*a,* 752*b,* respectively (or vice versa). When the first jaw space 752*a* is sized and shaped to form an interference fit with the jaw positioned in the first jaw space 752*a,* the first jaw space 752*a* can advantageously stabilize the device 188 on the loader 750 by stabilizing the jaw in the first jaw space 752a and can advantageously align the shuttle 14 with the jaw track that is in the first jaw space 752a (e.g., the upper jaw track 64 or the lower jaw track 66).

FIG. 14A further illustrates that the loader 750 can have a luer cap holder 770 that a luer cap can be removably secured to. The luer cap holder 770 can be a recess or a hole in the loader body 751. For example, FIG. 14A illustrates that the luer cap holder 770 can be a hole in the loader body 751.

FIG. 14A further illustrates that the loader 750 can have a loader length 750$_L$. The loader length 750$_L$ can be, for example, about 2.50 in. to about 5.00 in., including every 0.01 in. increment within this range (e.g., 2.50 in., 3.00 in., 3.50 in., 5.00 in.).

FIG. 14B illustrates that the device 188 can be placed in the device space 752. The device 188 can be removably attached to the loader 750 in the arrangement shown, with the upper jaw 30 in the first jaw space 752a and the lower jaw 38 in the second jaw space 752b, or vice versa. For example, FIG. 14B illustrates that the loader 750 can be used to load the upper jaw 30 with the shuttle 14. When the loader control 762 is moved from the loader control first position to the loader control second position, the shuttle 14 can be moved into the upper jaw 30, for example, from outside the upper jaw 30 in the shuttle first position to inside the upper jaw 30 in the shuttle second position.

FIG. 14B further illustrates the device 188 attached to the loader 750 before the jaws are closed against the cap 758. As another example, FIG. 14B illustrates the shuttle 14 can be loaded into the device 188 without closing the jaws against the cap 758. Before the jaws are closed against the cap 758, the jaws can float in the first and second jaw spaces 752a, 752b and may or may not make contact with the cap 758. For example, FIG. 14B illustrates the upper and lower jaws 30, 38 floating in the first and second jaw spaces 752a, 752b, respectively (or vice versa), with the upper jaw 30 in contact with the cap 758 and with the lower jaw 38 not in contact with the cap 758. When the jaws are closed against the cap 758, the upper and lower jaws 30, 38 can be in contact with the cap 758. When the jaws are closed against the cap 758, the upper and lower jaws 30, 38 can be clamped against the cap 758. When the jaws are closed against the cap 758, the jaws may not float in the first and second jaw spaces 752a, 752b.

FIG. 14B further illustrates that when the jaws are in the first and second jaw spaces 752a, 752b, the exposed portion 768 may not be in the jaw that is in the first jaw space 752a.

FIG. 14B further illustrates that the loader 750 can have a luer cap 772, and that the luer cap 772 can be removably attached to the luer cap holder 770.

FIG. 14B further illustrates that the device 188 can be removably attached to the loader 750 via the holders 754. For example, FIG. 14B illustrates that the holders 754 can be removably attached the compression cover 34 of the device 188. As another example, FIG. 14B illustrates that the compression cover 34 of the device 188 can be removably attached to the holders 754.

FIG. 14B further illustrates that the cap 758 can be opaque.

FIG. 14C illustrates that the cap 758 illustrated in FIG. 14B can be transparent, showing the shuttle 14, the suture loop 162, and the suture 70 under the cap 758.

Figure 14D:
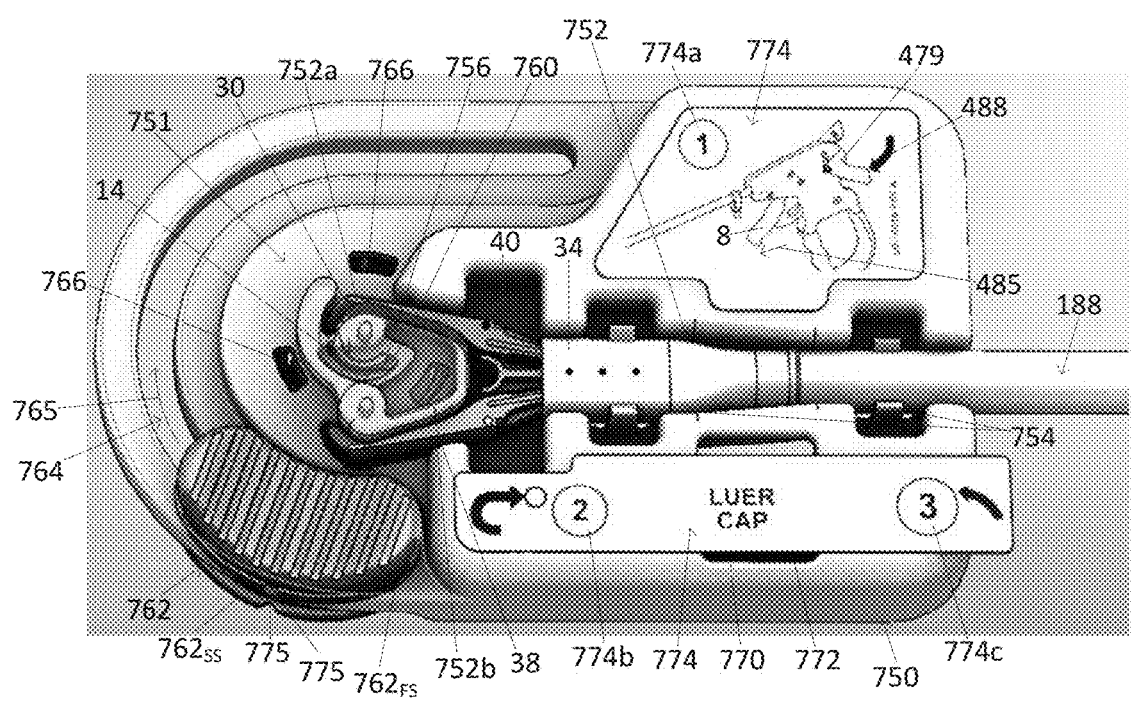
FIG. 14D illustrates a perspective view of a variation of a loader.

FIG. 14D illustrates that the loader 750 can have loading instructions 774. The loading instructions 774 can include, for example, a loading instruction first step 774a, a loading instruction second step 774b, and a loading instruction third step 774c. Each loading instruction step (e.g., loading instruction first, second, and third steps 774a, 774b, 774c) can include one or multiple instructions.

FIG. 14D illustrates that when the upper jaw 30 is to be loaded with the shuttle 14, the loading instruction first step 774a can include, for example, opening the jaws, moving the upper jaw pusher 86 to a fully retracted position, and placing the upper jaw 30 is in the first jaw space 752a and the lower jaw 38 is in the second jaw space 752b, or any combination thereof. For example, when the upper jaw 30 is to be loaded with the shuttle 14, the loading instruction first step 774a can include an instruction to load the device 188 onto the loader 750 with the trigger arrangement shown (e.g., with the jaw control 8 and the shuttle control 479 in the positions shown). As another example, the loading instruction first step 774a can include an instruction to move the jaw control 8 in direction 485 (e.g., which can be opposite to direction 484) to move the upper and lower jaws 30, 38 into an open configuration (e.g., into a fully open configuration), can include an instruction to move the shuttle control 479 to the fully advanced position in direction 488 to position the lower jaw pusher 76 in a fully advanced position and the upper jaw pusher 86 in a fully retracted position, or can include both instructions.

As another example, when the lower jaw 38 is to be loaded with the shuttle 14, the loading instruction first step 774a can include, for example, opening the jaws, moving the lower jaw pusher 76 to a fully retracted position, and placing the lower jaw 38 is in the first jaw space 752a and the upper jaw 30 is in the second jaw space 752b, or any combination thereof. For example, when the lower jaw 38 is to be loaded with the shuttle 14, the loading instruction first step 774a can include an instruction to load the device 188 onto the loader 750 with the jaw control 8 in the position shown in FIG. 14D and with the shuttle control 479 in the position shown, for example, in FIG. 13D). For example, the loading instruction first step 774a can include an instruction to move the jaw control 8 in direction 485 (e.g., which can be opposite to direction 484) to move the upper and lower jaws 30, 38 into an open configuration (e.g., into a fully open configuration), can include an instruction to move the shuttle control 479 to the fully advanced position in direction 486 (e.g., see FIG. 13D) to position the upper jaw pusher 86 in a fully advanced position and the lower jaw pusher 86 in a fully retracted position, or can include both instructions.

FIG. 14D illustrates that the loading instruction second step 774b can include moving the loader control 762 from the loader control first position to the loader control second position to move the shuttle 14 from the shuttle first position to the shuttle second position.

FIG. 14D illustrates that the loading instruction third step 774c can include removing the device 188 from the loader 750.

As another example, the loading instructions 774 can include a loading instruction step between the loading instruction first and second steps 774a, 774b that includes an instruction to close or clamp the jaws against the cap 758 by moving the jaw control in direction 484.

FIG. 14D further illustrates that the loader control track 764 can have the arrangement shown. The loader control 762 is shown transparent for illustrative purposes only, for example, to show the portion of the loader control track 764 under the loader control 762. As another example, the loader control 762 can be transparent. A transparent loader control 762 can advantageously allow the user to observe the suture 70 in the loader control 762, for example, so that the user can see whether or not the loader control 762 is properly pulling the suture 70 during the loading process. A transparent loader control 762 can advantageously allow the user to inspect the loader control 762 to verify that the suture 70 is properly positioned in the loader control 762 prior to loading the shuttle 14 into the device 188.

FIG. 14D further illustrates that the loader 750 can be packaged without the suture 70 or the suture loop 162 attached to the shuttle 14. FIG. 14D further illustrates that the suture 70 or the suture loop 162 can be attached to the shuttle 14 in the arrangement shown, and that the suture 70 can be attached to or passed through the loader control 762 in the arrangement shown.

FIG. 14D further illustrates that the shuttle 14 can be fully under the cap 758, for example, such that the shuttle 14 does not have the portion 768 extending out from under the cap 758 when the shuttle is in the shuttle first position (e.g., the position of the shuttle 14 in FIG. 14D).

FIG. 14D further illustrates that the luer cap 772 can be covered by the loading instructions 774. The loading instructions 774 can indicate the location of the luer cap 772. For example, FIG. 14D illustrates that the luer cap 772 is under "LUER CAP" on the loading instructions 774. To remove the luer cap 772 from the loader 750, the loading instructions 774 (e.g., the portion of the loading instructions 774 having the loading instruction second and third steps 774b, 774c) can be removed from the loader 750 (e.g., like a pull tab). As another example, to remove the luer cap 772 from the loader 750, the luer cap 772 can be pushed through the portion of the loading instructions 774 that cover the luer cap 772. Pushing the luer cap 772 through the loading instructions 774 can tear the loading instructions 774. As yet another example, to remove the luer cap 772 from the loader 750, the luer cap 772 can be removed from the back side of the loader 750 without having to remove or tear through the loading instructions 774.

FIG. 14D further illustrates that the loader control 762 can have a loader control first side $762_{FS}$ and a loader control second side $762_{SS}$. The loader control first side $762_{FS}$ can be on a first side of the loader 750 and the loader control second side $762_{SS}$ can be on a second side of the loader 750. For example, FIG. 14D illustrates that the loader control first side $762_{FS}$ can be on a front side of the loader 750 and that the loader control second side $762_{SS}$ can be on the back side of the loader 750. As shown in FIG. 14D, the loader control 762 can extend through the track 764.

The loader control first side $762_{FS}$ can be moveable toward the loader control second side $762_{SS}$. A portion of the loader control first side $762_{FS}$ can be moveable toward the loader control second side $762_{SS}$. A portion of the loader control second side $762_{SS}$ can be moveable toward the loader control first side $762_{FS}$. For example, the loader control first side $762_{FS}$ and/or the loader control second side $762_{SS}$ can have a loader control suture holder (e.g., see FIG. 19A for exemplary illustrated details) that can hold or lock the suture 70 in the loader control 762 as the loader control 762 is moved from the loader control first position to the loader control second position. The loader control suture holder can advantageously inhibit or prevent the suture 70 from slipping through the loader control 762 as the loader control 762 is moved from the loader control first position to the loader control second position. For example, the loader control suture holder can prevent the suture 70 from sliding through the loader control suture holder in the loader control 762 until a loader control threshold force is reached or exceeded. When the loader control threshold force is reached or exceeded, the suture 70 can slip or slide through the loader control suture holder in the loader control 762. In this way the loader control suture holder can advantageously inhibit or prevent the suture 70 from breaking or fraying, allowing the suture to slip or slide through the loader control 762 when the loader control 762 pulls the suture 70 and the shuttle 14 with a force equal to or greater than the loader control threshold force. The loader control threshold force can advantageously inhibit or prevent the integrity of the suture 70 from breaking or becoming damaged during the loading process.

The loader control suture holder can be, for example, a pad that the suture 70 can pass through. The pad can have a living hinge. The pad can be, for example, a silicon pad with two sides connected by the living hinge. As another example, the loader control suture holder can have two pads connected by a living hinge. The two pads and the living hinge can be, for example, a single silicon pad with a living hinge folded over on itself. The suture 70 can pass between the two pads of the loader control suture holder, or can pass between the two sides of a single pad of the loader control suture holder. When the loader control first side $762_{FS}$ and the loader control second side $762_{SS}$ are pressed together, the pad of the loader control suture holder can clamp the suture 70 in the loader control 762, preventing the suture 70 from slipping through the loader control 762 until the loader control threshold force is reached or exceeded as the loader control 762 is moved from the loader control first position to the loader control second position.

FIG. 14D further illustrates that the loader control 762 can have one or multiple loader control suture tracks 775 (also referred to as the tracks 775) that the suture 70 can be positionable in and/or that the suture 70 can be moveable in. The suture 70 can move (e.g., slide, translate) in the tracks 775, for example, as the suture 70 is pulled through the loader control 762. The tracks 775 can be one or multiple grooves or channels in the loader control 762. For example, FIG. 14D illustrates that the loader control first side $762_{FS}$ can have a track 775 and that the loader control second side $762_{SS}$ can have a track 775. The tracks 775 can advantageously keep the suture 70 at or below a surface of the loader control 762 so that the suture is not damaged by the user (e.g., via pulling, twisting, or rolling the suture 70) as user moves the loader control 762 from the loader control first position to the loader control second position.

Figure 14E:
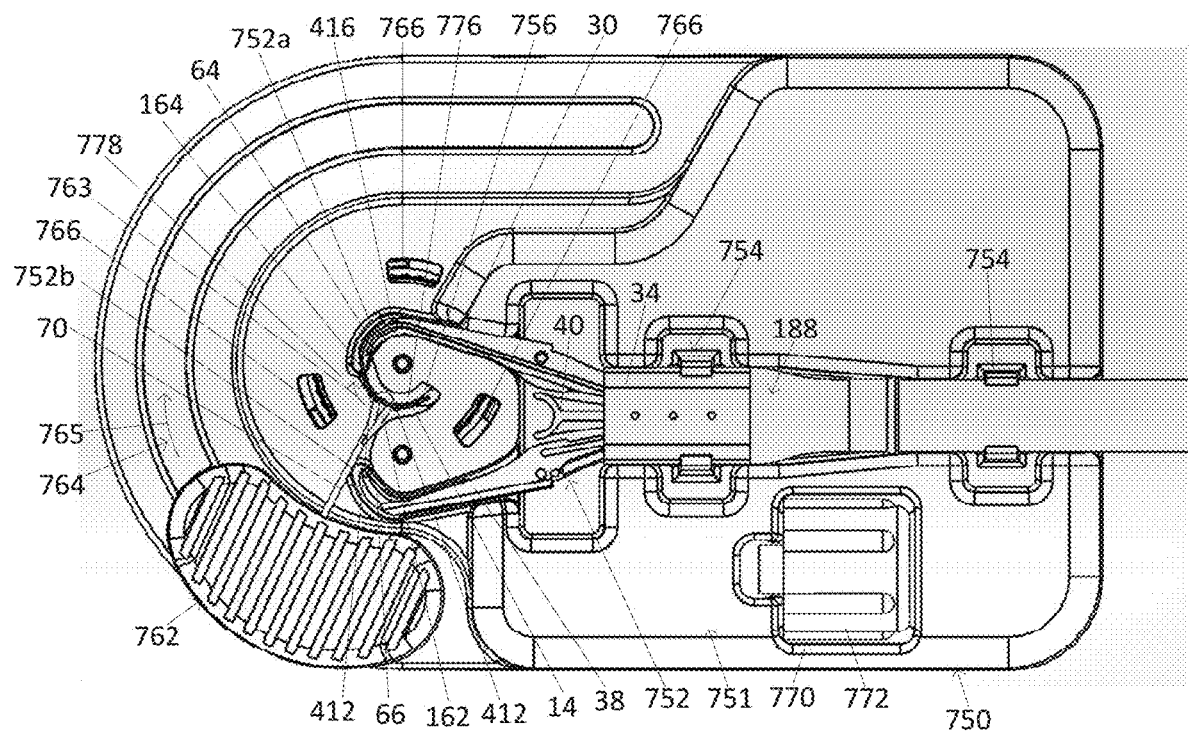
FIG. 14E illustrates a top view of a variation of a loader.

FIG. 14E illustrates that the loader 750 can be packaged with the suture 70 attached to the shuttle 14, for example, via the suture loop 162. Half of the upper and lower jaws 30, 38 in FIG. 14E are shown transparent for illustrative purposes only, for example, so that the relationship between the upper and lower jaw tracks 64, 66 and the shuttle 14 when the shuttle 14 is in the shuttle first position can be more easily seen. The upper jaw 30 is shown without the cover 556 and the lower jaw 38 is shown with the cover 556, for example, to illustrate that the device 188 can be attached to the loader 750 in the device space 750 with or without the cover 556. The cover 556 over the lower jaw 38 in FIG. 14E is shown opaque, but it can be transparent.

FIG. 14E further illustrates, for example, that when the jaws are in the first and second jaw spaces 752a, 752b, the exposed portion 768 can be aligned with the shuttle track of the jaw that is in the first jaw space 752a. For example, FIG. 14E illustrates that when the upper jaw 30 is in the first jaw space 752a, the shuttle tip 164 can be aligned with the upper jaw track 64 such that the shuttle 14 can be loaded into the upper jaw 30 when the loader control 762 is moved from the loader control first position to the loader control second position.

FIG. 14E further illustrates, for example, that the loader 750 can have a loader body suture track 776 (also referred to as the suture track 776 or the track 776). The track 776 can be a track in the loader body 751. The track 776 can be a groove in the loader body 751. The track 776 can be a channel in the loader body 751. The track 776 can be a ledge. For example, FIG. 14E illustrates that the track 776 can be a ledge. The track 776 can be parallel to the track 756. The track 776 can have a radius of curvature greater than, less than, or equal to the radius of curvature of the shuttle 14. The track 776 can have a radius of curvature greater than, less than, or equal to the radius of curvature of the track 756. The suture 70 and/or the suture loop 162 can be in the track 776 or can be positionable in the track 776. For example, FIG. 14E illustrates that the suture loop 162 can be in the track or can be positionable in the track 776. For example, FIG. 14E illustrates that the loader 750 can be packaged with the suture loop 162 attached to the shuttle 14 and positioned in the track 776 in the arrangement shown, for example, when the shuttle 14 is in the shuttle first position and the loader control 762 is in the loader control first position.

The suture 70 and/or the suture loop 162 can be moveable (e.g., translatable, slideable) in the track 776. The suture 70 and/or the suture loop 162 can be longitudinally moveable along the track 776. For example, the suture 70 and/or the suture loop 162 can be translatable or slideable along the track 776. The suture 70 and/or the suture loop 162 can be moveable out of (e.g., longitudinally out of) the track 776, for example, into the upper jaw track 64 and/or into the upper jaw suture slot 238b. The suture 70 and/or the suture loop 162 can be moveable out of (e.g., longitudinally out of) the track 776, for example, into the lower jaw track 66 and/or into the lower jaw suture slot 238a. For example, when the shuttle 14 is in the shuttle first position, FIG. 14E illustrates that the shuttle 14 can be in the track 756 and that the suture loop 162 can be in the track 776. When the shuttle 14 is in the shuttle second position and has been loaded into the upper jaw 30, the shuttle 14 can be in the upper jaw 30, and the suture loop 162 can be in the upper jaw track 64 and/or in the upper jaw suture slot 238b. When the shuttle 14 is in the shuttle second position and has been loaded into the lower jaw 38, the shuttle 14 can be in the lower jaw 38, and the suture loop 162 can be in the lower jaw track 66 and/or in the lower jaw suture slot 238a.

FIG. 14E further illustrates that the shuttle body can have a loader body surface 778 (also referred to as the surface 778). The surface 778 can form an edge of the track 776. The surface 778 can form an edge of the first jaw space 752a. The surface 778 can form an edge of the second jaw space 752b. For example, FIG. 14E illustrates that the surface 778 can abut or form the edge of the first and second jaw spaces 752a, 752b. FIG. 14E illustrates that the male stops 412 on the shuttle 14, the suture loop 162, and the suture 70 can extend over the surface 778. The male stops 412 on the shuttle 14, the suture loop 162, and the suture 70 can be moveable across the surface 778, for example, as the shuttle 14 is moved from the shuttle first position to the shuttle second position. The male stops 412 on the shuttle 14, the suture loop 162, and/or the suture 70 may or may not contact the surface 778. For example, as the shuttle 14 is moved from the shuttle first position to the shuttle second position, the male stops 412 on the shuttle 14, the suture loop 162, and/or the suture 70 may or may not contact the surface 778. For example, FIG. 14E illustrates that as the shuttle 14 is moved from the shuttle first position to the shuttle second position, the male stops 412 on the shuttle 14, the suture loop 162, and/or the suture 70 can extend over the surface 778 without contacting the surface 778 as the male stops 412 on the shuttle 14, the suture loop 162, and/or the suture 70 are moved across the surface 778 by the loader control 762 as the loader control 762 is moved, for example, from the loader control first position to the loader control second position.

Figure 14F:
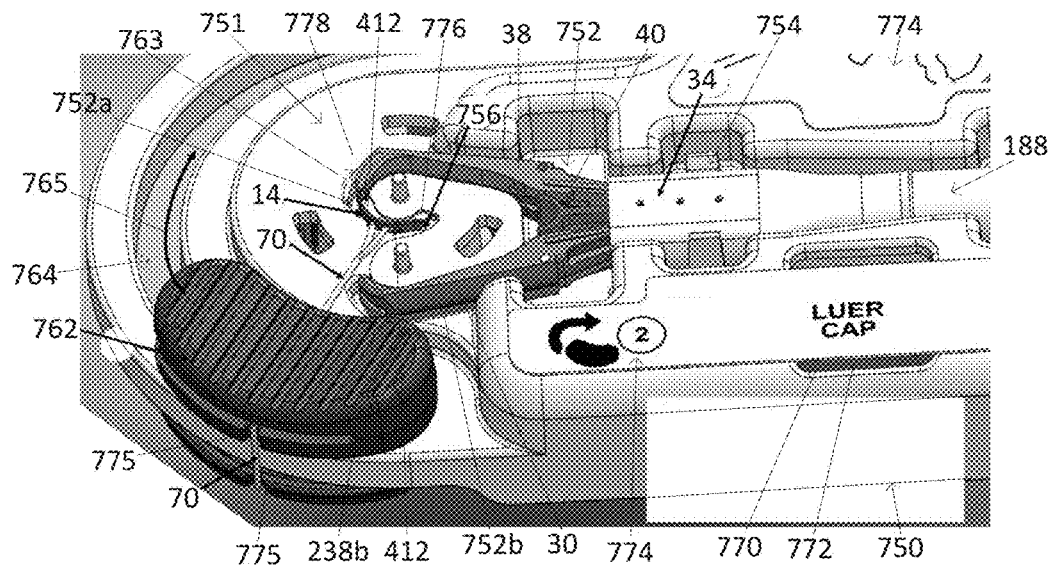
FIG. 14F illustrates a perspective view of a variation of a loader.

FIG. 14F illustrates the device 188 in the loader 750 with the cap 758 shown transparent for illustrative purposes only. As another example, FIG. 14F illustrates that the loader 750 may not have a cap (e.g., the cap 758).

FIG. 14F further illustrates that the first jaw space 752a can be deeper than the track 756, and that the track 756 can be deeper than the track 776. For example, the first jaw space 752a can have a first jaw space depth, the track 756 can have a loader body shuttle track depth, and the track 776 can have a loader body suture track depth. FIG. 14F illustrates, for example, that the first jaw space depth can be greater than the loader body shuttle track depth, and the loader body shuttle track depth can be greater than the loader body suture track depth. FIG. 14F further illustrates that the surface 778 and the bottom surface of the track 776 can be the same level as each other. As another example, the track 776 can be deeper than the surface 778. As yet another example, the surface 778 can form the track 776.

FIG. 14F further illustrates that the suture 70 can extend from the shuttle 14 toward the loader control 762 and loop around the loader 750 from a first side of the loader 750 to a second side of the loader 750 through the loader control 762. For example, FIG. 14F illustrates that the suture 70 can extend through the loader control 762 (e.g., through the loader control suture holder).

FIG. 14F further illustrates that the lower jaw 38 can be placed in the first jaw space 752a and that the upper jaw 30 can be placed in the second jaw space 752b.

Figure 15A:
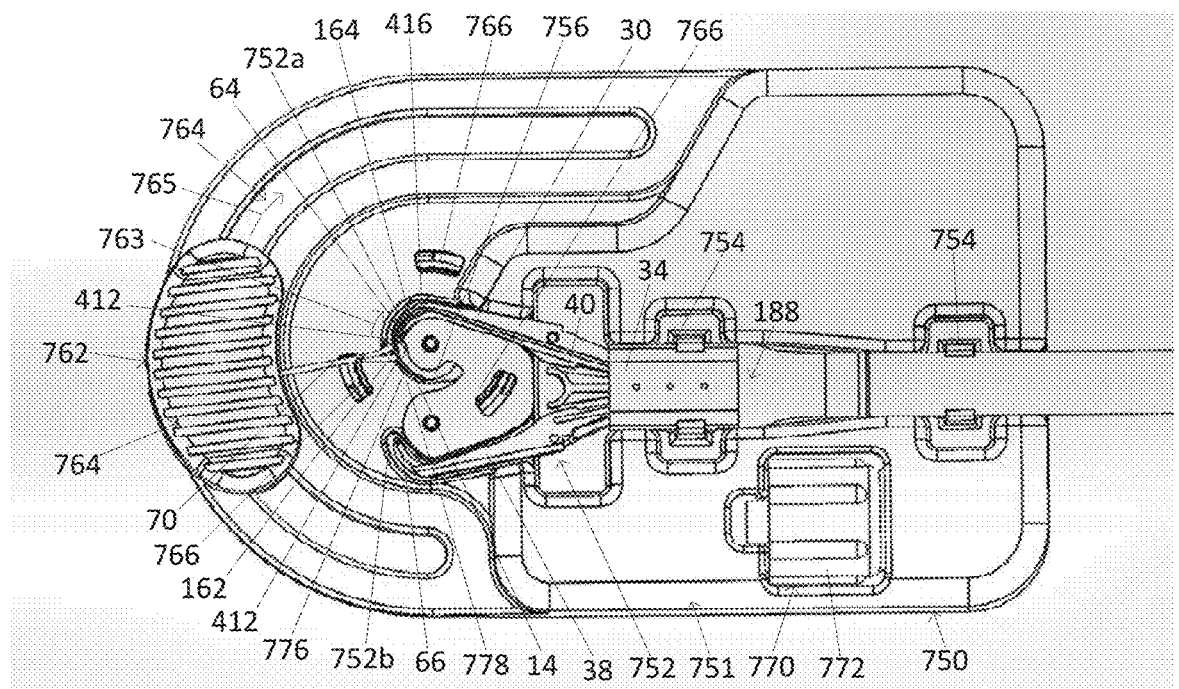
FIG. 15A illustrates a top view of a variation of a loader.

FIG. 15A illustrates that the jaws can be clamped against the loader body 751 (e.g., by pulling the jaw control 8). When the jaws are clamped against the loader body 571, the shuttle 14 can be loaded into the device 188 via the loader control 762. As another example, half of the jaws can be clamped against the loader body 751 and half of the jaws can be clamped against the cap 758 (e.g., shown transparent in FIG. 15A). FIG. 15A shows the loader 750 and the device 188 of FIG. 14E in a mid-loaded configuration (also referred to as a partially loaded configuration). As for FIG. 14E, half of the upper and lower jaws 30, 38 in FIG. 15A are shown transparent for illustrative purposes only, for example, so that the relationship between the upper and lower jaw tracks 64, 66 and the shuttle 14 when the shuttle 14 is between the shuttle first and second positions can be more easily seen. The upper jaw 30 is shown without the cover 556 and the lower jaw 38 is shown with the cover 556, for example, to illustrate that the device 188 can be attached to the loader 750 in the device space 752 with or without the cover 556.

FIG. 15A illustrates the loader control 762 can be moved away from the loader control first position to a loader control intermediate position between the loader control first and second positions. FIG. 15A illustrates that when the loader control 762 is in an intermediate position, the shuttle 14 can be between the shuttle first and second positions, for example, in a shuttle intermediate position. The intermediate position of the loader control 762 illustrated in FIG. 15A is also referred to as the loader control first intermediate position. The intermediate position of the shuttle 14 illustrated in FIG. 15A is also referred to as the shuttle first intermediate position.

FIG. 15A illustrates, for example, the loader 750 in a partially loaded configuration and the device 188 in a partially loaded configuration. When the loader 750 is in a partially loaded configuration, the loader control 762 can be between the first and second terminal ends of the track 764. When the loader 750 is in a partially loaded configuration, the loader control 762 can be between the loader control first position and the loader control second position, for example, in an intermediate position between the loader control first and second positions as shown in FIG. 15A. When the loader 750 is in a partially loaded configuration, the suture loop 162 can extend over the track 756, the track 776, and the surface 778. When the device 188 is in a partially loaded configuration, a first end of the shuttle 14 can be in the device 188 (e.g., in the upper jaw 30 or in the lower jaw 38) and a second end of the shuttle 14 can be outside of the device 188, for example, in the track 756. When the loader 750 is in a partially loaded configuration, the shuttle 14 can be between the shuttle first position and the shuttle second position, for example, in an intermediate position between the shuttle first and second positions as shown in FIG. 15A. When the device 188 is in a partially loaded configuration, the suture loop 162 can extend over the track 756, the track 776, and the surface 778.

Figure 15B:
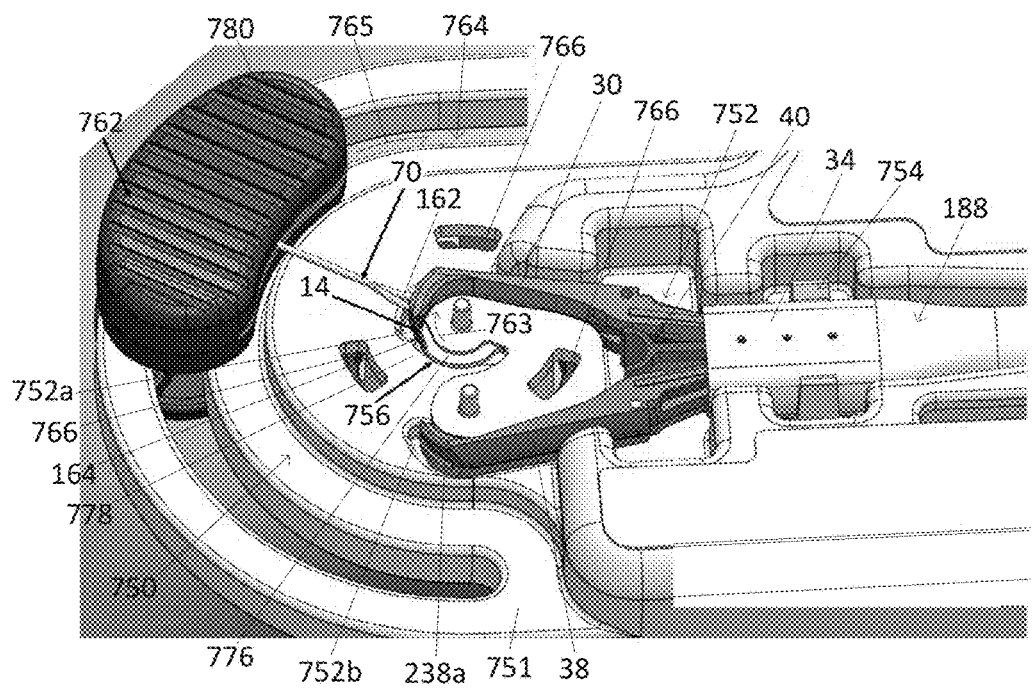
FIG. 15B illustrates a perspective view of a variation of a loader.

FIG. 15B illustrates that the loader control 762 can be moved away from the loader control first intermediate position to a loader control second intermediate position, where the loader control second intermediate position can be between the loader control first and second positions. The loader control second intermediate position can be between the loader control first intermediate position and the loader control second position. FIG. 15B illustrates that when the loader control 762 is in the loader control second intermediate position, the shuttle 14 can be between the shuttle first and second positions, for example, in a shuttle second intermediate position. The shuttle second intermediate position can be between the shuttle first intermediate position and the shuttle second position.

FIG. 15B illustrates, for example, the loader 750 in a partially loaded configuration and the device 188 in a partially loaded configuration. When the loader and the device 750, 188 are in a partially loaded configuration and the loader control 762 is in the loader control second intermediate position, the suture loop 162 can be in the upper jaw 30, extend through the upper jaw suture slot 238b, and extend over both the first jaw space 752a and the surface 778. FIG. 15B illustrates the suture 70 and the suture loop 162 can be fully out of the track 776. When the device 188 is in a partially loaded configuration and the loader control 762 is in the loader control second intermediate position, a first end of the shuttle 14 can be in the device 188 (e.g., in the upper jaw 30 or in the lower jaw 38) and a second end of the shuttle 14 can be outside of the device 188, for example, in the track 756. FIG. 15B illustrates that both of the male stops 412 illustrated in FIG. 15A can be in the upper jaw 30 (e.g., they no longer extend over the surface 778). In the partially loaded configuration shown in FIG. 15B, the male stops 412 may not be engaged with a female stop 416.

FIG. 15B further illustrates that the loader control 762 (e.g., the loader control first side 762$_{FS}$) can have a loader control channel 780 (also referred to as the channel 780). The channel 780 can be the opening to the loader control suture holder. FIG. 15B illustrates that the suture 70 can extend into the channel 780, for example, from the shuttle 14.

Figure 15C:
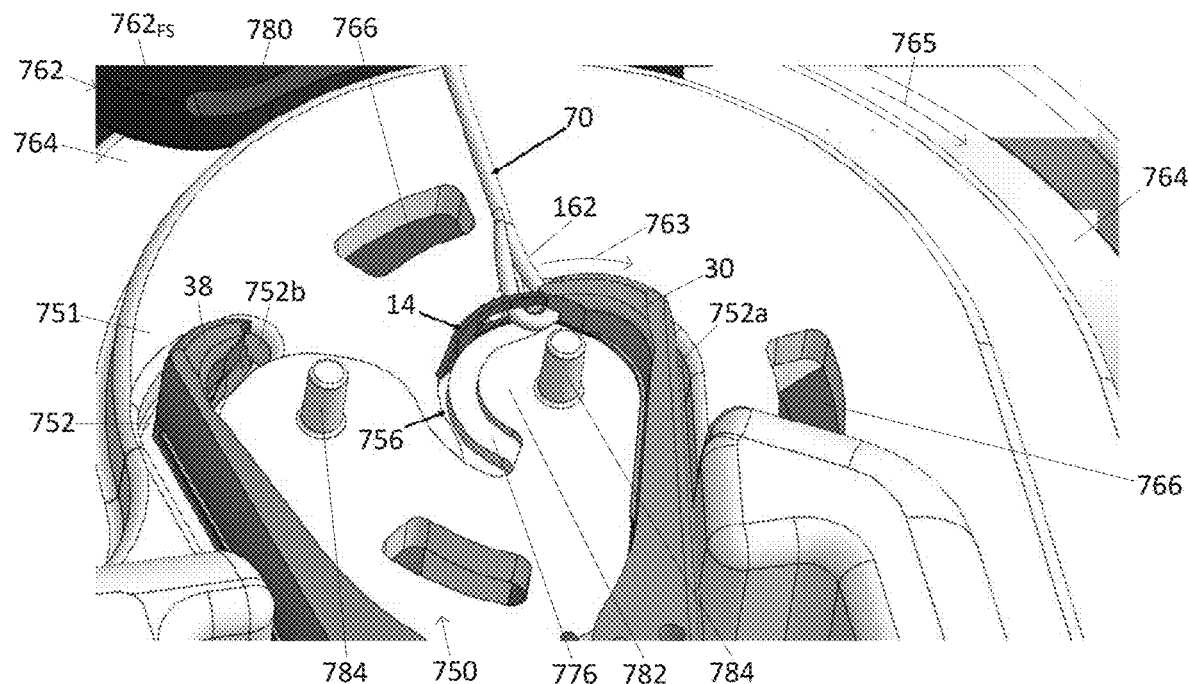
FIG. 15C illustrates a magnified perspective view of the loader of FIG. 15B.

FIG. 15C illustrates that the surface 778 and the track 776 can be the same height. As another example, the surface 778 can define the track 776.

FIG. 15C further illustrates that the cap 758 can be placed on a surface 782. The surface 782 can be above the track 776 and the surface 778, for example, to provide clearance (e.g., a gap, a space) between the cap 758 and the surface 778 for the suture 70, the suture loop 162, and/or the male stops 412 to extend into when the cap 758 is attached to the loader 750. The cap 758 can be attached to (e.g., glued to) or rest against the surface 782. The cap 758 can be attached to the cap attachers 784. The cap attachers 784 can be, for example, posts or masts. For example, the cap 758 can be glued to the posts 784. As another example, the cap 758 can be removably attachable to the posts 784, for example, with a friction fit, a snap fit, or a magnetic fit. When the cap 758 is attached to the cap attachers 784, the cap 758 can contact or rest against the surface 782.

Figure 15D:
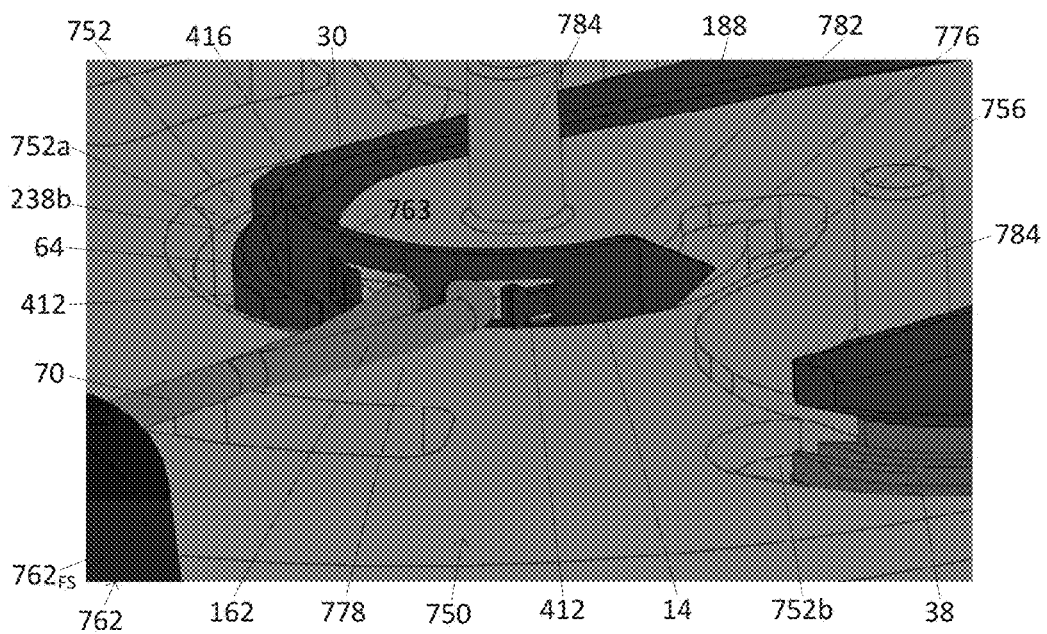
FIG. 15D illustrates a magnified perspective view of the loader of FIG. 15C.

FIG. 15D illustrates that when the loader control 762 is in a loader control intermediate position, for example, the intermediate position shown in FIG. 15C, the loader 750 and the device 188 can have the arrangement of features shown, for example, with the suture 70 extending across the surface 778 to the loader control 762.

Figure 15E:
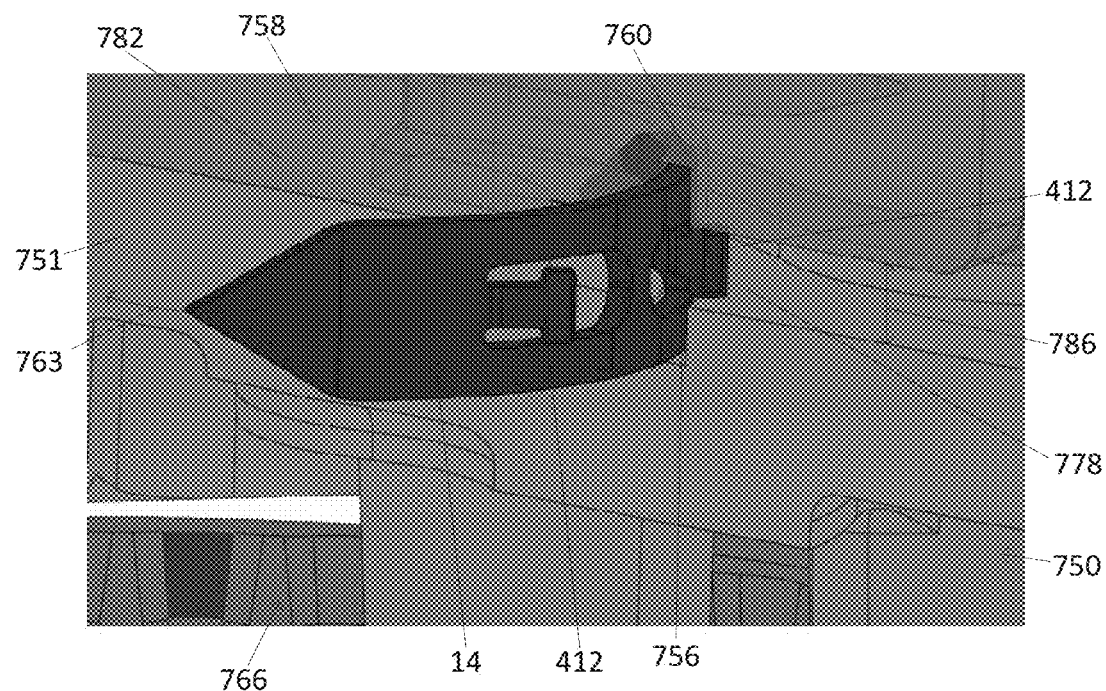
FIG. 15E illustrates a magnified perspective cross-sectional view of the loader of FIG. 15D.

FIG. 15E illustrates that when the cap 758 is attached to the loader 750, a bottom surface of the cap 758 can be in contact with the surface 782.

FIG. 15E further illustrates that when the cap 758 is attached to the loader 750, a space 786 (also referred to as a gap 786) can be between the cap 758 and the surface 778 for the suture 70, the suture loop 162, and/or the male stops 412 to extend into and/or move through. The suture 70, the suture loop 162, and/or the male stops 412 can be moveable in the space 786.

FIG. 15E further illustrates that the track 756 can be opposite of the track 760 such that a first lateral side of the shuttle 14 is moveable in the track 756 and a second lateral side of the shuttle 14 is moveable in the track 760.

Figure 15F:
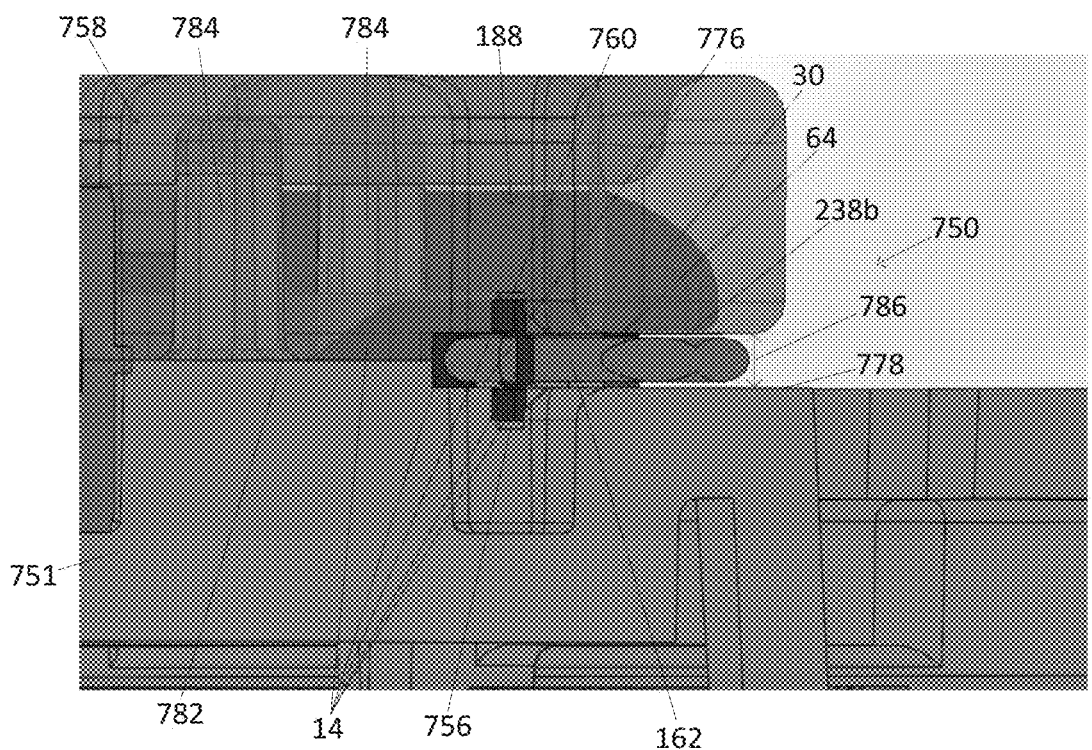
FIG. 15F illustrates a magnified perspective cross-sectional view of the loader of FIG. 15C.

FIG. 15F illustrates that the suture loop 162 can be in the gap 786. The suture loop 162 can be in the gap 786, for example, when the loader control 762 is in the loader control first position, is in the loader control second position, and/or is in any position between the loader control first and second positions. As another example, the suture loop 162 may no longer extend through the gap 786 when the loader control 762 is in the loader control second position. For example, FIG. 15F can illustrate a cross-sectional view of FIG. 14A with the cap 758 attached to the loader 750. As another example, FIG. 15F can illustrate a cross-sectional view of FIG. 15A with the cap 758 attached to the loader 750. As yet another example, FIG. 15F can illustrate a cross-sectional view of FIG. 15B with the cap 758 attached to the loader 750.

FIG. 15F further illustrates that the gap 786 can be between the cap 758 and the loader body 751, for example, to inhibit or prevent the suture 70 from lifting out of the plane that extends, for example, between the shuttle 14 and the loader control 762, and that FIG. 15F shows can be parallel to the surface 778.

FIG. 15F further illustrates that the surface defining the track 776 and the surface 778 can be same level as each other. For example, the surface defining the track 776 and the surface 778 can be the same distance away from the bottom of the cap 758.

Figure 16:
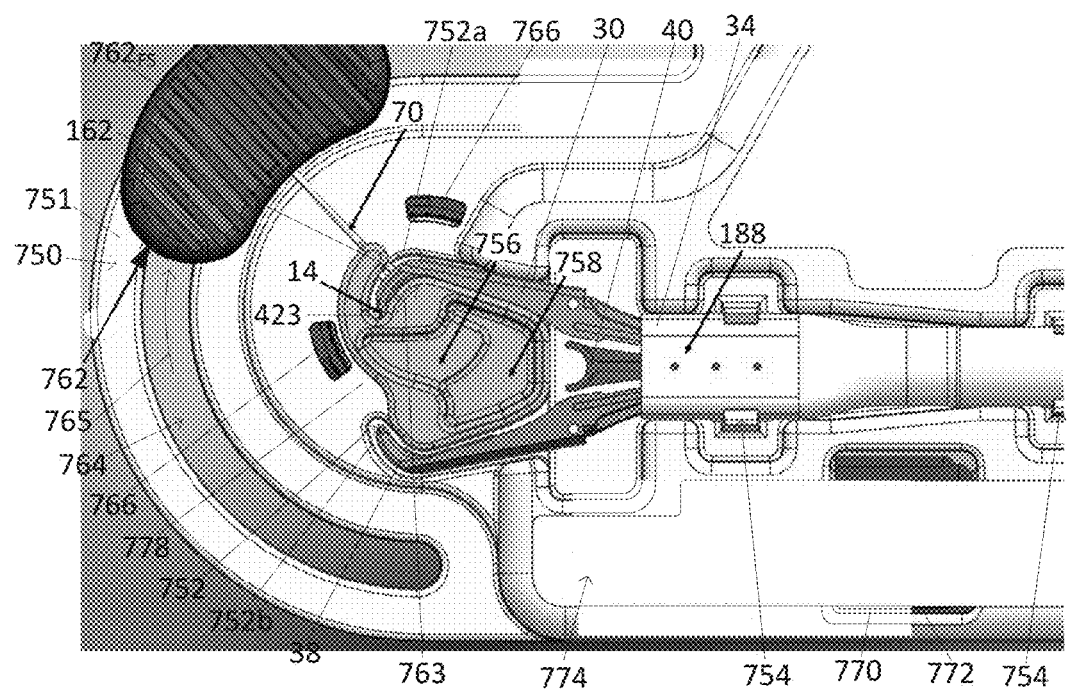
FIG. 16 illustrates a top view of a variation of a loader.

FIG. 16 illustrates that the loader control 762 can be moved to the loader control second position. For example, FIG. 16 illustrates that the loader control 762 can be moved away from the loader control second intermediate position to the loader control second position. FIG. 16 illustrates that when the loader control 762 is in the loader control second position, the loader 750 and the device 188 can have the arrangement of features as shown. FIG. 16 illustrates, for example, that when the loader control 762 is in the loader control second position, the shuttle 14 can be in the shuttle second position, and that the shuttle second position can be a fully loaded position. When the loader control 762 is in the loader control second position, FIG. 16 illustrates that a male stop can be engaged with a female stop. When the loader control 762 is moved into the loader control second position (e.g., from the loader control first position), the shuttle 14 can be moved out of the track 756 into the device 188 (e.g., into the upper jaw 30 or into the lower jaw 38), the suture loop 162 can be moved out of or off of the track 776 onto or over the surface 778 and/or onto or over the first jaw space 752a, and the suture 70 can moved out of or off of the track 776 and onto or over the surface 778 and/or onto or over the first jaw space 752a, or any combination thereof. FIG. 16 further illustrates that when the loader control 762 is in the loader control second position, the exposed portion 423 can extend from the device 188. As another example, when the loader control 762 is in the loader control second position and the shuttle 14 is in the shuttle second position, the shuttle 14 can be fully in the device 188, for example, such that the shuttle 14 does not extend from the device 188 or does not have an exposed portion (e.g., exposed portion 423).

FIG. 16 further illustrates that the suture 70 and/or the suture loop 162 can extend under the cap 758 (e.g., under a finger of the cap 758), for example, through the space 786, when the loader control 762 is in the loader control second intermediate position shown in FIG. 15B.

FIG. 16 further illustrates that the cap 558 can be placed over the track 756.

FIG. 16 further illustrates that half of the jaws can be clamped against the loader body 751 and that half of the jaws can be clamped against the cap 751.

Figure 17A:
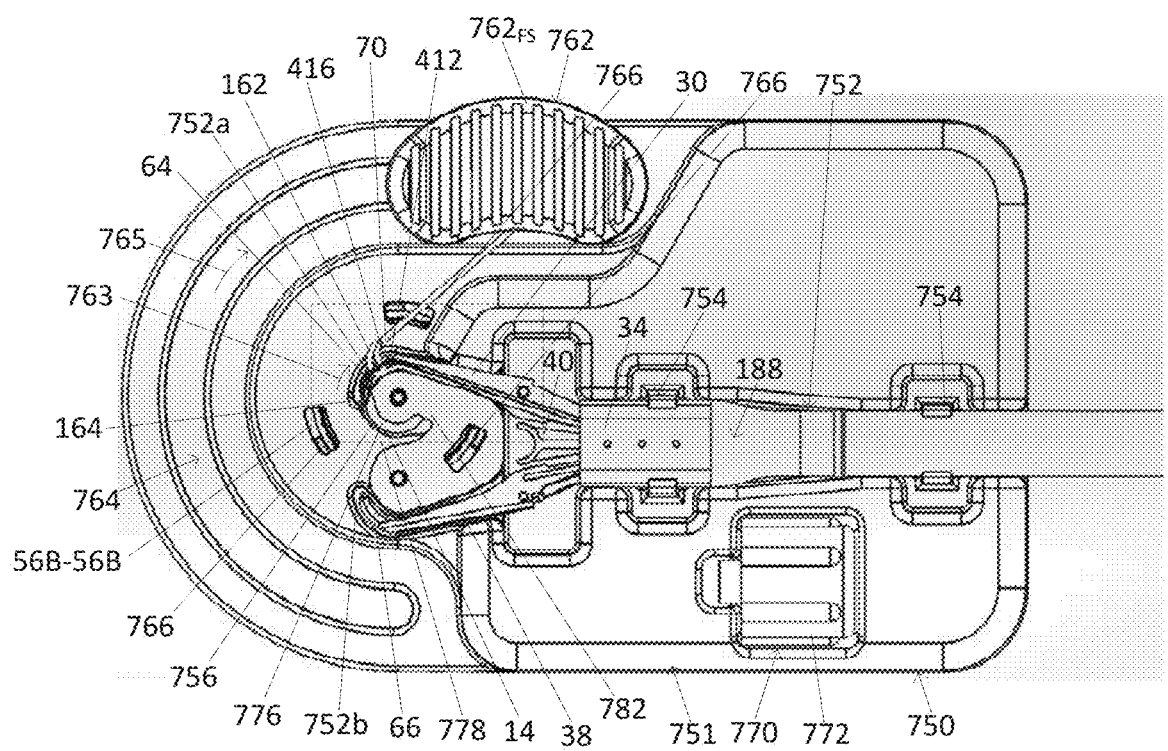
FIG. 17A illustrates a top view of a variation of a loader.

FIG. 17A illustrates that the loader control 762 can be moved to the loader control third position. FIG. 17A illustrates that when the loader control 762 is in the loader control third position, the loader 750 and the device 188 can have the arrangement of features as shown. FIG. 17A illustrates, for example, that when the loader control 762 is in the loader control third position, the shuttle 14 can be in the shuttle second position, and that the shuttle second position can be a fully loaded position. As another example, when the loader control 762 is in the loader control third position, the shuttle 14 can be in a shuttle third position, which can be an overloaded position in the device 188. When the shuttle 14 is in the shuttle third position, more of the shuttle 14 can be in the device 188 than when the shuttle 14 is in the shuttle second position. For example, when the shuttle 14 is in the shuttle second position, the exposed portion 423 can extend from the device 188, and when the shuttle 14 is in the shuttle third position, less of the exposed portion 423 can extend from the device 188 or the shuttle 14 can be completely in the device 188. As another example, the shuttle 14 can have the same position (e.g., the shuttle second position) when the loader control 762 is in the loader control second position and when the loader control 762 is in the loader control third position.

FIG. 17A further illustrates that when the loader control 762 is in the loader control third position, the loader control 762 can be at the second terminal end of the track 764. When the loader control 762 is in the loader control third position, the suture 70 and the suture loop 162 can be in the positions shown. When the loader control 762 is in the loader control third position, FIG. 17A illustrates that a male stop can be engaged with a female stop. As the loader control 762 is moved from the loader control second position to the loader control third position, the suture 70 can slip through the loader control suture holder. The loader control suture holder can be a friction member that the suture 70 can slip through. As for FIGS. 14E and 15A, the cap 758 and half of the upper and lower jaws 30, 38 in FIG. 17A are shown transparent for illustrative purposes only, for example, so that the relationship between the upper and lower jaw tracks 64, 66 and the shuttle 14 when the shuttle 14 is in the shuttle third position can be more easily seen. The upper jaw 30 is shown without the cover 166 and the lower jaw 38 is shown with the cover 556, for example, to illustrate that the device 188 can be attached to the loader 750 in the device space 752 with or without the cover 556.

Figure 17B:
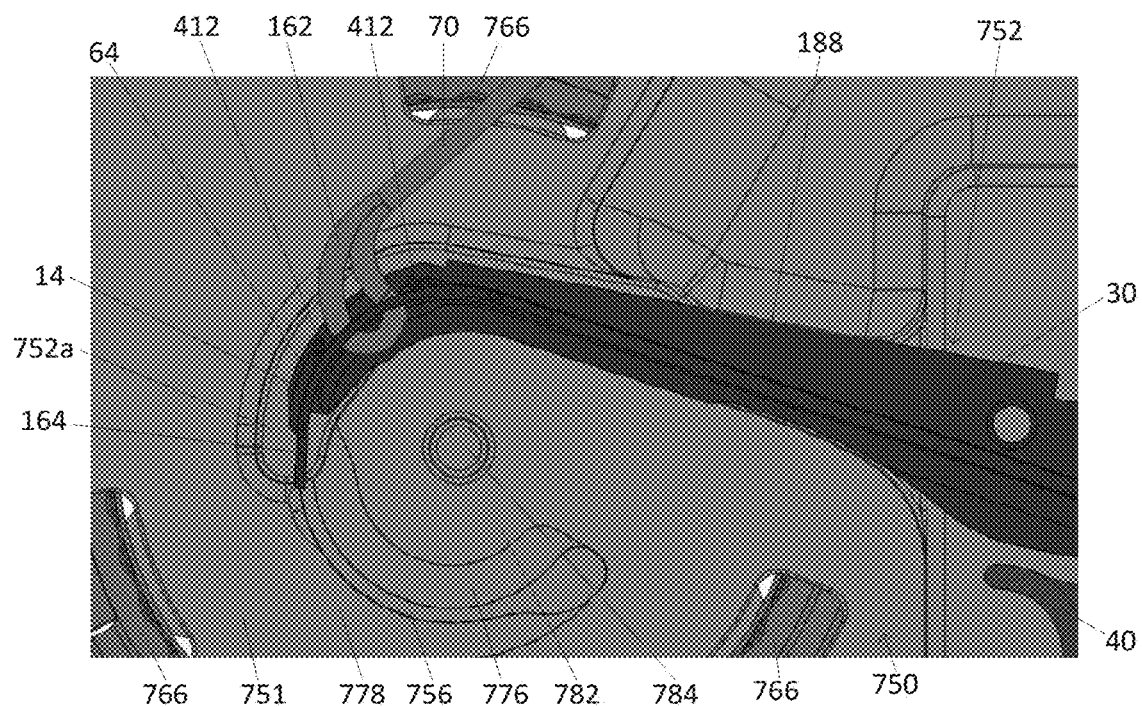
FIG. 17B is a magnified view of the loader of FIG. 17A at section 17B-17B.

FIG. 17B illustrates that when the loader control 762 is moved into the loader control third position (e.g., from the loader control first position), the shuttle 14 can be moved out of the track 756 into the device 188 (e.g., into the upper jaw 30 or into the lower jaw 38), the suture loop 162 can be moved out of or off of the track 776 onto or over the surface 778 and/or onto or over the first jaw space 752a, and the suture 70 can moved out of or off of the track 776 and onto or over the surface 778 and/or onto or over the first jaw space 752a, or any combination thereof.

FIG. 17B further illustrates that when the loader control 762 is in the loader control third position, the exposed portion 423 can extend from the device 188. As another example, when the loader control 762 is in the loader control second position and the shuttle 14 is in the shuttle second position, the shuttle 14 can be fully in the device 188, for example, such that the shuttle 14 does not extend from the device 188, does not have an exposed portion (e.g., exposed portion 423), or less of the exposed portion 423 is exposed when the loader control 762 is in the loader control third position than when in the loader control second position.

Figure 17C:
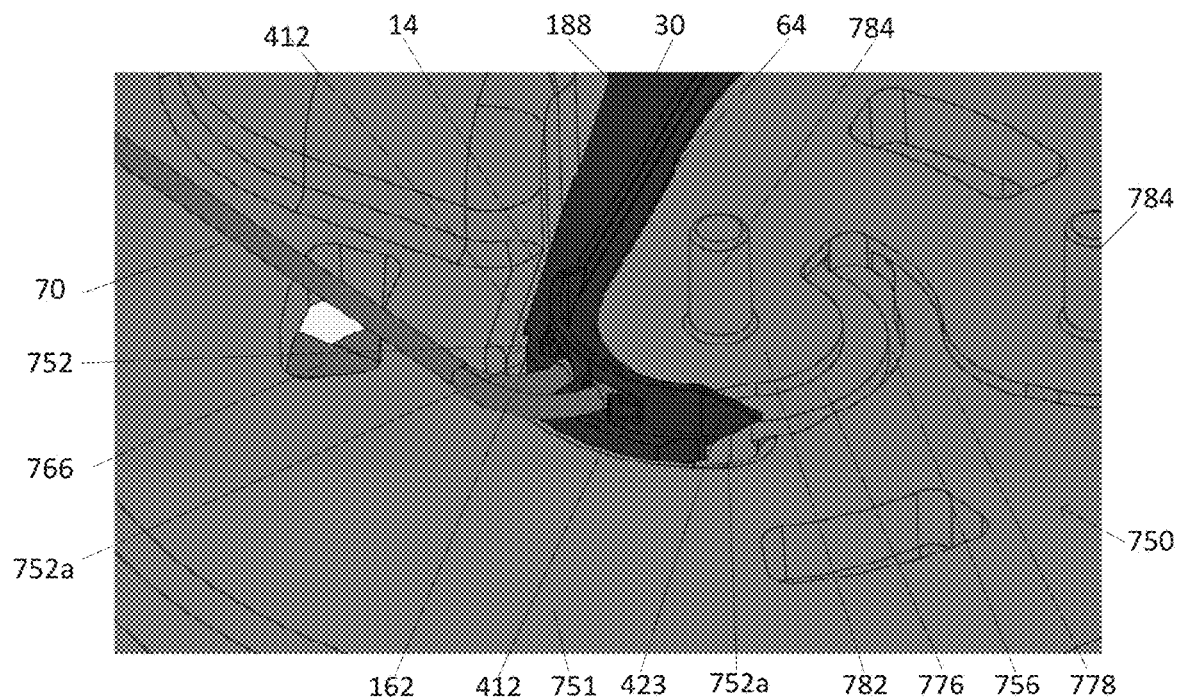
FIG. 17C is a perspective view of FIG. 17B.

FIG. 17C illustrates the arrangement of features shown, for example, that the surface 782 can be a ledge, that the track 776 can be a ledge, that the track 756 can be a channel, that the surface 778 can form a ledge that abuts and forms a wall of the track 756, and that the surface 778 and the surface forming the track 776 can be the same height (e.g., the same height above the bottom of the track 756.

Figure 18:
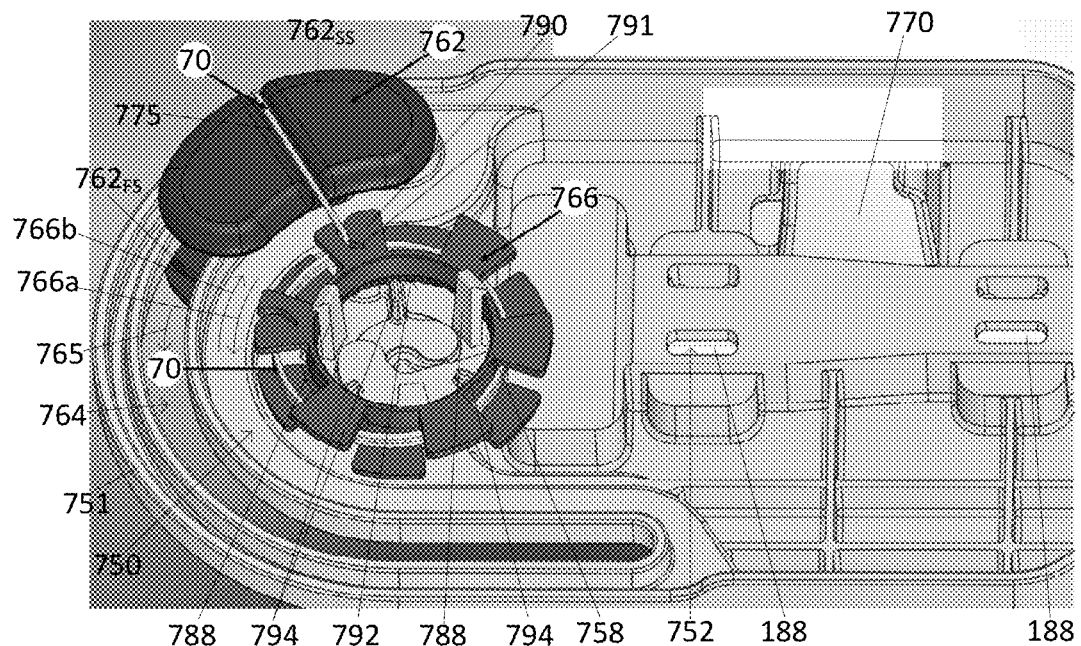
FIG. 18 is a bottom view of a variation of a loader.

FIG. 18 illustrates that the suture holder 766 can be attached to (e.g., removably attached to) the loader 750. The suture holder 766 can be attached to the front side or the back side of the loader 750. For example, FIG. 18 illustrates that the suture holder 766 can be attached to the back side of the loader 750.

FIG. 18 further illustrates that loader 750 can have one or multiple holders 788 that can hold the suture holder 766 and the loader 750 together. For example, FIG. 18 illustrates that the holders 788 can hold the suture holder 766 on the back side of the loader 750. The holders 788 can be, for example, clips, clasps, magnets, or fasteners, clasps, catches, pins, or any combination thereof. For example, FIG. 18 illustrates that the holders 788 can be clips that the suture holder 766 can be snapped into. FIG. 18 illustrates that the loader 750 can be packaged with the suture holder 766 attached to the loader 750, for example, in the arrangement shown with suture 70 on (e.g., wound around) the suture holder 766. The holders 788 can be part of the loader body 751. The holders 788 can be extensions of the loader body 751. The holders 788 can extend from the loader body 751.

FIG. 18 further illustrates that the suture holder 766 can be rotatable for example, in direction 766a, in direction 766b, or in directions 766a and 766b. When the suture holder 766 is attached to the loader 750 (e.g., in the position shown in FIG. 18), the suture holder 766 can be rotatable (e.g., in directions 766a and/or 766b). For example, the suture holder 766 can rotate in direction 766a as the loader control 762 is moved (e.g., from the loader control first position to any subsequent position, for example, to the loader control second position and/or to the loader control third position). The suture 70 can release from the suture holder 766 as the suture holder rotates in direction 766a. As another example, the suture holder 766 can rotate in direction 766a as the loader control 762 but the suture 70 may not begin releasing (e.g., passively releasing) from the suture holder 766 until the loader control 762 is in the loader control second position or beyond. For example, FIG. 18 further illustrates that the suture holder 766 can have a suture grabber 790 that can inhibit or prevent the suture 70 from releasing (e.g., unspooling, unwinding) from the suture holder 766 until the loader control 762 is in the loader control second position or beyond. This can advantageously keep the suture 70 in tension while the shuttle 14 is being loaded into the device 188 via the loader control 762. For example, the suture grabber 790 can have a track 791 that the suture 70 can extend through. The track 791 can be a channel, a groove, or a hole in the suture holder 766. For example, FIG. 18 illustrates that the track 791 can be a groove or a channel. The track 791 can have curve (e.g., the crescent curve shown) so that the suture 70 is inhibited from releasing from the suture grabber 790 until the loader control 762 is in the loader control second position or until the loader control threshold force is reached or exceeded. Once the loader control 762 is in the loader control second position, movement of the loader control 762 further in direction 765, for example, to the loader control third position, can release the suture 70 from the suture grabber 790 by turning the suture holder 766 to such an extent that that the suture 70 can be pulled out of the track 791 as the loader control 762 is moved beyond the loader control second position. Once the suture 70 is pulled out of the track 791, the suture 70 can release (e.g., unwind, unspool) from the suture holder 766.

When the loader control 762 is in any position, the user can pull the suture 70 (e.g., with their hands) to release (e.g., actively release) the suture 70 from the suture holder 766. Passive release from the suture holder 766 can be when movement of the loader control 762 releases the suture 70 from the suture holder 766 and passive release from the suture holder 766 can be when the user removes the suture 70 from the suture holder 766, for example, by pulling the suture 70. For example, when the shuttle 14 is fully loaded into the device 188 (e.g., when the shuttle 14 is in the shuttle second position and the loader control 762 is in any position ranging from the loader control second position to the loader control third position), the user can release the device 188 from the loader 750 and can pull the rest of the suture 70 off of the suture holder 766 (e.g., through the loader control 762), for example, directly with their hands or simply by pulling the device 188 and the loader 750 away from each other.

FIG. 18 further illustrates that the suture holder 766 can have ribs 792 that can engage with rib engagers 794. The loader 750 can have, for example, 1 to 3 or more rib engagers 794. For example, FIG. 18 illustrates that the loader 750 can have three rib engagers 794, spaced 120 degrees apart from each other. The ribs and rib engagers 792, 794 can inhibit or prevent the suture holder 766 from moving in direction 766a and/or in direction 766b before use (e.g., when packaged). The ribs and rib engagers 792, 794 can provide tactile and/or audible feedback to the user that can indicate that the suture holder 766 is rotating in direction 766a during loading. The audible feedback can be, for example, audible clicks that are generated as the suture holder rotates and the ribs 792 rotate past the rib engagers 794.

FIG. 18 further illustrates that the suture holder 766 can be a spool.

FIG. 18 further illustrates that the track 775 on the loader control second side $762_{SS}$ can have the arrangement shown, for example, that it can extend across the outer surface of the loader control second side $762_{SS}$.

As the loader control 762 is moved from the loader control first position to the loader control second position or to the loader control third position, the suture 70 can, for example, passively release (e.g., unspool) from the suture holder 766.

The loader 750 can be packaged with or without suture 70 on (e.g., wound around) the suture holder 766. For example, FIG. 18 illustrates that the loader 750 can be packaged with the suture 70 wound around the suture holder 766. Where the loader 750 is not packaged with the suture 70 attached to the loader 750, the suture 70 can be attached to the suture holder and extended through the loader 762 before use.

Figure 19A:
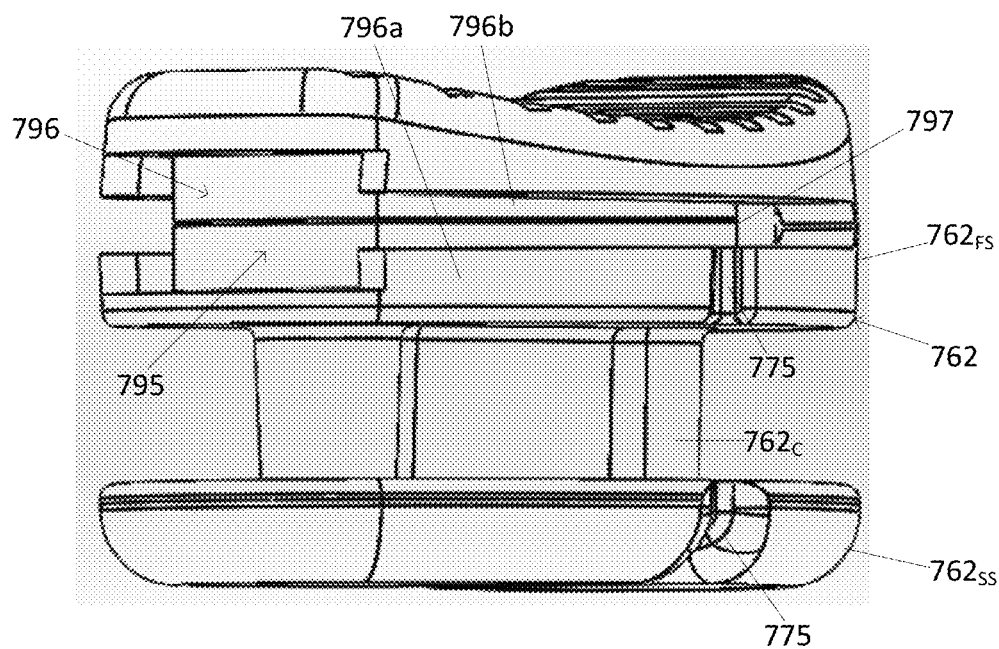
FIG. 19A is a perspective view of a variation of a loader control.

FIG. 19A illustrates that the loader control suture holder can be the loader control suture holder 795. FIG. 19A illustrates that the loader control 762 can have or can be the loader control suture holder 795. The loader control suture holder 795 can be a friction member that inhibits or prevents the suture 70 from slipping through the loader control 762 until the loader control threshold force is reached or exceeded. For example, the loader control suture holder 795 can, for example, have a pad 796 that the suture 70 can pass through. The pad can be, for example, a silicon pad. The loader control suture holder 795 can have a living hinge 797. The living hinge 797 can be, for example, a portion (e.g., a middle portion, a folded portion) of the pad 796. The pad can be, for example, a pad with two sides (e.g., a pad first side 796a and a pad second side 796b) that can be connected by the living hinge 797. As another example, the loader control suture holder 795 can have two pads connected by a living hinge. The two pads and the living hinge can be, for example, a single pad (e.g., pad 796) folded over on itself as shown in FIG. 19A. The fold in the pad 796 can be the living hinge 797. The suture 70 can pass between the two pads of the loader control suture holder, or can pass between the two sides (e.g., the pad first and second sides 796a, 796b) of a single pad of the loader control suture holder 795. When the loader control first side $762_{FS}$ and the loader control second side $762_{SS}$ are pressed together, the pad 796 of the loader control suture holder 795 can clamp the suture 70 in the loader control 762, inhibiting or preventing the suture 70 from slipping through the loader control 762 until the loader control threshold force is reached or exceeded as the loader control 762 is moved from the loader control first position to the loader control second position. The suture 70 can slip through the loader control suture holder 795, for example, as the loader control 762 is moved from a fully loaded position to an overloaded position. For example, the suture 70 can slip through the loader control suture holder 795 as the loader control 762 is moved from the loader control second position to the loader control third position. The threshold force can be, for example, from about 2.00 lbs to about 10.00 lbs, including every 0.01 lb increment within this range (e.g., 2.00 lbs, 3.00 lbs, 6.00 lbs, 10.00 lbs). The threshold force can be higher than the loading force needed for loading the shuttle 14 into the device 188. For example, the loading force can be about 0.30 lbs to about 4.00 lbs, including every 0.01 lb increment within this range (e.g., 0.30 lbs, 0.50 lbs, 2.00 lbs, 4.00 lbs).

FIG. 19A further illustrates that a first half of the loader control first side $762_{FS}$ can be lifted in direction 798 to open the loader control suture holder 795. When the loader control suture holder 795 is opened, the first half of the loader control first side $762_{FS}$ can rotate about the living hinge 797 away from a second half of the loader control first side $762_{FS}$. The loader control suture holder 795 can be opened, for example, to load the loader control 762 with the suture 70, to remove the suture 70 from the loader control 762 (e.g., after the shuttle 14 is fully loaded into the device), or both.

FIG. 19A further illustrates that the loader control 762 can have a loader control connector $762_C$ that can connect the loader control first and second sides $762_{FS}$, $762_{SS}$, and which can extend through the track 764.

Figure 19B:
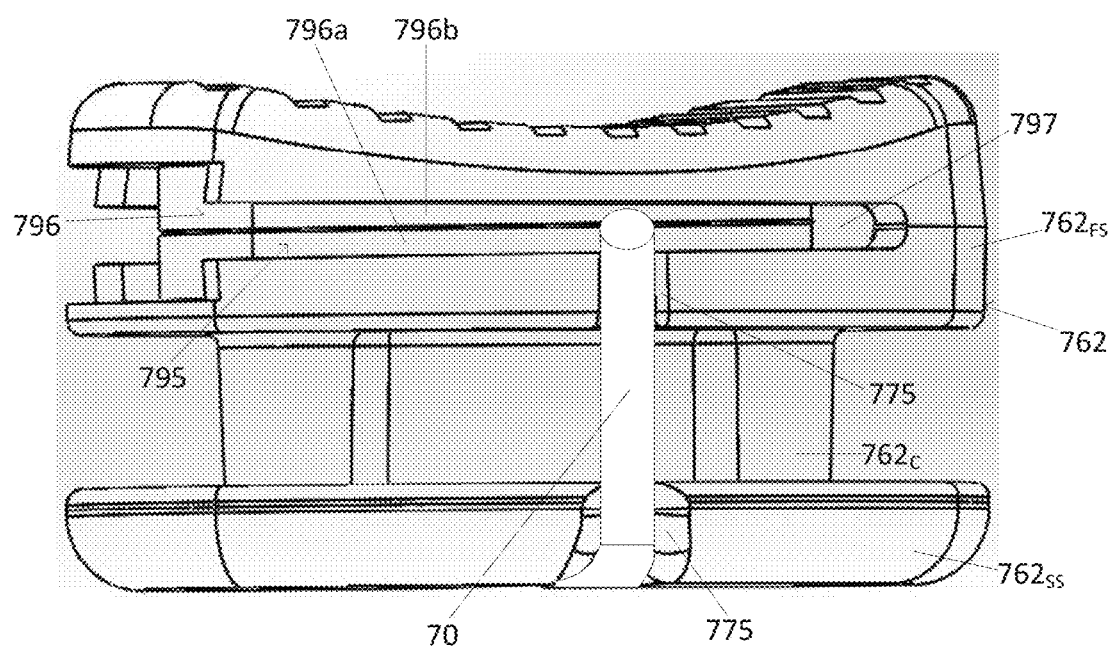
FIG. 19B is a perspective view of a variation of a loader control.

FIG. 19B illustrates that the suture 70 can be extend though the through the loader control suture holder 795. For example, 19B illustrates that the suture 70 can extend transversely through the loader control suture holder 795 between the pad first side 796a and the pad second side 796b.

The loader control suture holder 795 can hold the suture 70 and/or the suture 70 can slip through the loader control suture holder 795 without the suture 70 being damaged.

The shuttle 14 can be loaded into the device 188 (e.g., into the upper jaw 30 or the lower jaw 38) using one hands or two hands. For example, two handed loading, one hand can be squeezing the jaw control 8 to clamp the jaws against the loader 750 (e.g., against the cap 758 and/or against the loader body 751) and the other hand can move the loader control 762, for example, from the loader control first position to the loader control second position or any subsequent loader control position (e.g., to the loader control third position). For one handed loading, the device 188 can be placed in the device space 752 and the loader 750 can be tilted so that gravity can cause the upper and lower jaws 30, 38 to make contact with the cap 758 and/or with the loader body 751 so that the shuttle 14 can be loaded into the device 188. While the loader 750 is tilted, one or both hands can move the loader control 762, for example, from the loader control first position to the loader control second position or any subsequent loader control position (e.g., to the loader control third position).

The loader 750 can be a single-use loader or a multiple-use loader. Where the loader 750 is a single-use loader, the loader 750 can be disposed of after the shuttle 14 is loaded into the device 188. Where the loader 750 is a multiple-use loader, a new shuttle 14 can be inserted into the loader 750 (e.g., into the tracks 758 and/or 760), new suture 70 can be attached to the shuttle 14 and extended through the loader control 762 (e.g., through the loader control suture holder 795), and/or the new suture 70 can be wound around the suture holder 766.

The device 188 can be a multiple-use device, such that one or multiple shuttles 14 can be loaded and removed from the device 188. For example, where the shuttle has a lifespan of 2 to 10 passes through tissue, the shuttle 14 can be removed from the device 188 once the lifespan of the shuttle 14 expires or after the shuttle 14 no longer adequately moves or cuts through tissue (e.g., whichever is earlier) and a new shuttle 14 can be loaded into the device 188 using the same loader 750 (e.g., if the loader is multiple-use) or a different loader 750 (e.g., if the loader is single-use).

The handle of the device 188 in FIGS. 14B-15B, 16, and 17A is not shown for illustrative purposes only.

When the shuttle 14 is in the shuttle first position (e.g., a shuttle non-loaded position), the shuttle 14 can have a shuttle first radius of curvature. When the shuttle 14 is in the shuttle second position (e.g., a shuttle loaded position), the shuttle 14 can have a shuttle second radius of curvature. The shuttle first and second radius of curvatures can be the same as or different from each other. For example, when different from each other, the shuttle first radius of curvature can be less then or greater than the shuttle second radius of curvature. For example, FIG. 14A illustrates that when the shuttle 14 is in the shuttle first position, the shuttle 14 can have the shuttle first radius of curvature, and FIGS. 16 and 17A illustrate that when the shuttle 14 is in the shuttle second position, the shuttle 14 can have the shuttle second radius of curvature. FIGS. 16 and 17A further illustrate that the shuttle second radius of curvature can be less than the shuttle first radius of curvature. For example, the shuttle second radius of curvature can be, for example, about 0.010 in. to about 0.075 in. less than the shuttle first radius of curvature, including every 0.001 in. increment within this range (e.g., 0.010 in., 0.015 in., 0.075 in.). The shuttle 14 can be a spring. For example, when the shuttle 14 has the shuttle second radius of curvature, the shuttle 14 can be biased to have the shuttle first radius of curvature. For example, when the shuttle 14 has the shuttle second radius of curvature and is in the upper jaw 30 or the lower jaw 38, the shuttle 14 can be biased to push the male stops 412 outward (e.g., radially outward) into the female stops 416 when the shuttle 14 is moved (e.g., translated) into the upper jaw 30 or into the lower jaw 38 from the loader 750 (e.g., via the loader control 762). As another example, the shuttle 14 can have the same radius of curvature (e.g., the shuttle first radius of curvature) before and after being loaded into the device 188. For example, the shuttle 14 can have the same radius of curvature (e.g., the shuttle first radius of curvature) when the shuttle 14 is in the shuttle first position and when the shuttle 14 is in the shuttle second position. The loader control 762 can move the male stops 412 into engagement with the female stops 416, for example, by moving the loader in direction 765 (e.g., from the loader control first position to the loader control second position). As another example, the loader control 762 can move the male stops 412 out of engagement with the female stops 416, for example, by moving the loader in a direction opposite to direction 765 (e.g., from the control second position to the loader control first position), for example, if an adjustment is desired (e.g., realign the shuttle 14 or the device 188 in or on the loader 750).

The loader 750 can be used to load a suture and/or a shuttle into a suture device (e.g., a device 188). The loader 750 can have a suture (e.g., the suture 70) and/or a shuttle (e.g., the shuttle 14) that can be moved (e.g., via a loader control 762) from a non-loaded configuration (e.g., FIG. 14A) to a loaded configuration (e.g., FIGS. 16 and/or FIG. 17A) without damaging the suture or the shuttle, or with causing minimal damage to the suture or the shuttle such that the suture or the shuttle can still be used after the minimal damage is caused during the loading the loading process.

Any of the devices (e.g., devices 188) disclosed, illustrated, and/or contemplated herein can be removably attachable to the loader 750, for example, to load the shuttle 14 into the device.

Any systems, devices, features, and/or methods disclosed, illustrated, and/or contemplated in U.S. application Ser. No. 14/255,945 filed Apr. 17, 2014 (published as US 2014/

0316443), in International Application No. PCT/US2019/025203 filed Apr. 1, 2019 (published as WO 2019/191768), and/or in U.S. Application No. 16/733,740 filed Jan. 3, 2020 each of which is herein incorporated by reference in its entirety for all purposes—can be used with the loader 750 for any purpose (e.g., to load any of the systems, devices, and/or features in any of these applications with a suture and/or with a shuttle) and/or can be combined with any of the systems, devices, features, and/or methods disclosed, illustrated, and/or contemplated herein for any purpose.

It is apparent to one skilled in the art that various changes and modifications can be made to this disclosure, and equivalents employed, without departing from the spirit and scope of the disclosure. Elements shown with any variation are exemplary for the specific variation and can be used on other variations within this disclosure. Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the disclosure, and variations of aspects of the disclosure can be combined and modified with each other in any combination. Any phrase involving an "A and/or B" construction or similar construction can mean (1) A alone, (2) B alone, (3) A and B together. Any range disclosed can include any subrange of the range disclosed, for example, a range of 1-10 units can include 2-10 units, 8-10 units, or any other subrange.

We claim:

1. A suture device loader comprising:
   a body having a device space;
   a loader control; and
   a shuttle moveable from a shuttle first position to a shuttle second position,
   wherein the shuttle is moveable from the shuttle first position to the shuttle second position via the loader control,
   wherein when the shuttle is in the shuttle first position, a suture device is positionable in the device space,
   wherein when the suture device is positioned in the device space, the shuttle is moveable from the shuttle first position to the shuttle second position,
   wherein when the shuttle is in the shuttle first position, the shuttle is outside the suture device, and
   wherein when the shuttle is in the shuttle second position, the shuttle is inside the suture device.

2. The suture device loader of claim 1, wherein the loader control is moveable from a loader control first position to a loader control second position, wherein when the loader control is in the loader control first position, the shuttle is in the shuttle first position, and wherein when the loader control is in the loader control second position, the shuttle is in the shuttle second position.

3. The suture device loader of claim 2, wherein the body has a loader control track, and wherein the loader control is translatable along the loader control track from the loader control first position to the loader control second position.

4. The suture device loader of claim 2, wherein the shuttle is pullable or pushable into the suture device via the loader control.

5. The suture device loader of claim 2, wherein when the shuttle is in the shuttle first position, the shuttle has a shuttle first radius of curvature, and wherein when the shuttle is in the shuttle second position, the shuttle has a shuttle second radius of curvature different from the shuttle first radius of curvature.

6. The suture device loader of claim 5, wherein the shuttle second radius of curvature is less than the shuttle first radius of curvature.

7. The suture device loader of claim 2, wherein the body has a shuttle track and a suture track, wherein the shuttle is moveable in the shuttle track, and wherein a suture is moveable in the suture track.

8. The suture device loader of claim 7, wherein the suture track has a suture track first side and a suture track second side, wherein the suture track first side is on a first side of the shuttle track, wherein the suture track second side is on a second side of the shuttle track, and wherein when the shuttle is in the shuttle first position, the suture extends over the suture track first side and extends over the suture track second side.

9. The suture device loader of claim 2, further comprising a suture, wherein the shuttle is connected to the loader control via the suture.

10. The suture device loader of claim 9, wherein the suture is under less tension when the loader control is in the loader control first position than when the loader control is in the loader control second position.

11. The suture device loader of claim 9, wherein the suture is under more tension when the shuttle is inside the suture device than when the shuttle is in the shuttle first position.

12. A suture device loader comprising:
    a body having a device space; and
    a suture moveable from a suture first position to a suture second position,
    wherein when the suture is in the suture first position, a suture device is positionable in the device space,
    wherein when the suture device is positioned in the device space, the suture is moveable from the suture first position to the suture second position, and
    wherein more of the suture is in the suture device when the suture is in the suture second position than when the suture is in the suture first position.

13. The suture device loader of claim 12, wherein none of the suture is in the suture device when the suture is in the suture first position.

14. The suture device loader of claim 12, further comprising a loader control, wherein the suture is moveable from the suture first position to the suture second position via the loader control.

15. The suture device loader of claim 14, wherein the loader control is moveable from a loader control first position to a loader control second position, wherein when the loader control is in the loader control first position, the suture is in the suture first position, and wherein when the loader control is in the loader control second position, the suture is in the suture second position.

16. The suture device loader of claim 15, wherein the suture is pullable or pushable into the suture device via the loader control.

17. The suture device loader of claim 15, wherein the suture is under less tension when the suture is in the suture first position than when the suture is in the suture second position.

18. The suture device loader of claim 15, further comprising a shuttle, wherein the suture has a suture first portion and a suture second portion, wherein the suture first portion is connected to the shuttle, wherein the suture second portion is connected to the loader control, wherein when the suture device is positioned in the device space, the shuttle is moveable from a shuttle first position to a shuttle second position, wherein when the suture is in the suture first position, the shuttle is in the shuttle first position, wherein when the suture is in the suture second position, the shuttle is in the shuttle second position, and wherein more of the shuttle is in the suture device loader when the shuttle is in the shuttle first position than when the shuttle is in the shuttle second position.

19. A method of loading a suture device, comprising:
removably attaching the suture device to a loader, wherein the loader has a loader control, a suture, and a shuttle; and
loading, via the loader control, the shuttle and the suture into the suture device,
wherein loading comprises moving, via the loader control, the shuttle and the suture from a non-loaded configuration to a loaded configuration by moving the loader control from a loader control first position to a loader control second position, wherein when the loader control is in the loader control first position, the shuttle and the suture are in the non-loaded configuration, and wherein when the loader control is in the loader control second position, the shuttle and the suture are in the loaded configuration.

* * * * *